United States Patent [19]
Snell et al.

[11] Patent Number: 5,724,985
[45] Date of Patent: Mar. 10, 1998

[54] USER INTERFACE FOR AN IMPLANTABLE MEDICAL DEVICE USING AN INTEGRATED DIGITIZER DISPLAY SCREEN

[75] Inventors: Jeffery D. Snell, Oak Park; Thomas G. Levin, Northridge, both of Calif.

[73] Assignee: Pacesetter, Inc., Sylmar, Calif.

[21] Appl. No.: 510,367

[22] Filed: Aug. 2, 1995

[51] Int. Cl.⁶ .................................................. A61N 1/00
[52] U.S. Cl. ................................. 128/697; 607/30
[58] Field of Search ................................. 128/710, 696, 128/697; 364/413.06; 607/30

[56] References Cited

U.S. PATENT DOCUMENTS

| | | |
|---|---|---|
| 4,098,267 | 7/1978 | Stein et al. |
| 4,142,533 | 3/1979 | Brownlee et al. |
| 4,476,869 | 10/1984 | Bihn |
| 4,527,567 | 7/1985 | Fischler et al. |
| 4,596,255 | 6/1986 | Snell et al. |
| 4,791,936 | 12/1988 | Snell et al. |
| 4,809,697 | 3/1989 | Causey, III et al. |
| 4,860,218 | 8/1989 | Sleator |
| 4,875,483 | 10/1989 | Vollmann et al. |
| 4,944,298 | 7/1990 | Sholder |
| 4,958,632 | 9/1990 | Duggan |
| 5,012,411 | 4/1991 | Policastro et al. ............. 364/413.06 |
| 5,339,824 | 8/1994 | Engira .................................. 128/710 |
| 5,447,164 | 9/1995 | Shaya et al. ....................... 128/710 |
| 5,469,858 | 11/1995 | Osborne ............................. 128/710 |

OTHER PUBLICATIONS

GO Corporation, "Background Information: GO Corp.'s Penpoint ™ Operating System for Mobile, Pen–Based Computers," (No date).

GO Corporation, *Using Penpoint (Penpoint Operating System)*, Version 1.0, pp. 9–17, 89–104, 117–133, 201–221 (1990–1992).

*Primary Examiner*—Scott Getzow

[57] ABSTRACT

An apparatus and a method for an improved user interface for communicating with implantable medical devices are described. An integrated digitizer display screen and a digitizer pen serve as the primary input devices to a tablet computer adapted to receive real-time and stored medical data. The pen is used to select programming options by tapping portions of the digitizer based on visual images on the display. Additionally, the pen may be used to manipulate the medical data through the use of gestures, or be used to enter free form annotations concerning the medical data. An additional aspect of the user interface is the use of a questionnaire card to input information into the tablet computer by tapping the pen on the marked answers on the questionnaire card.

50 Claims, 29 Drawing Sheets

FIG. 6

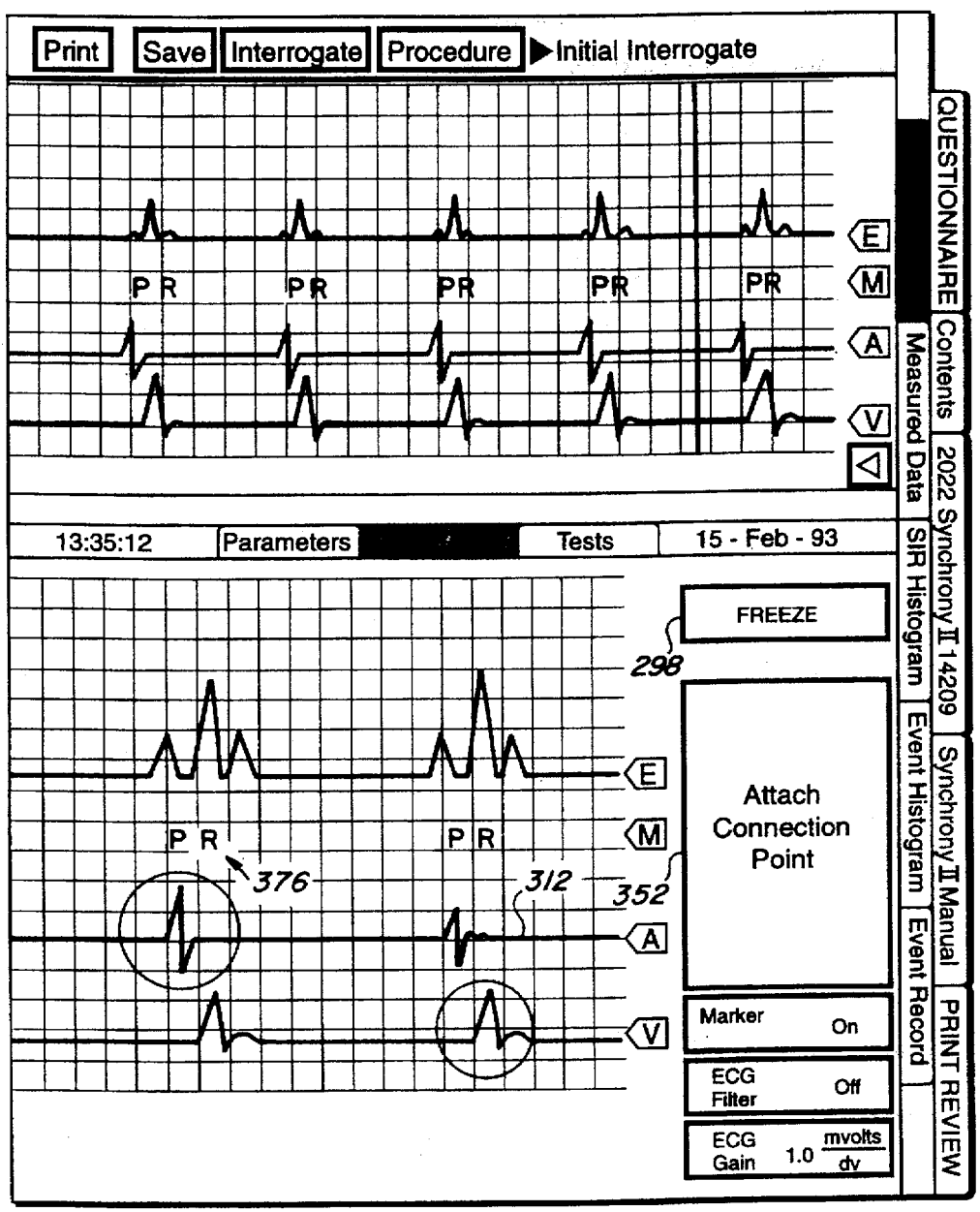
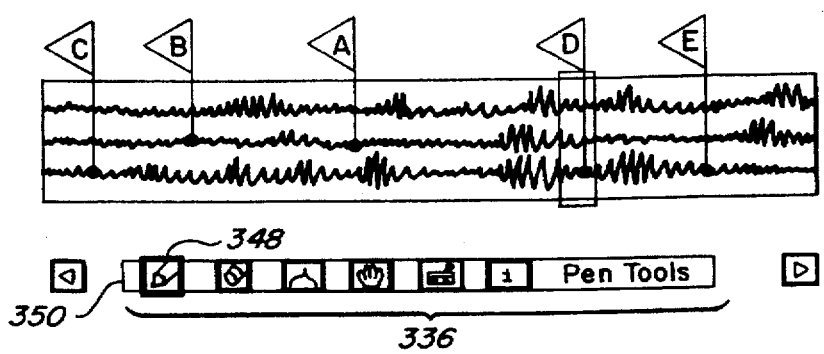
FIG. 13

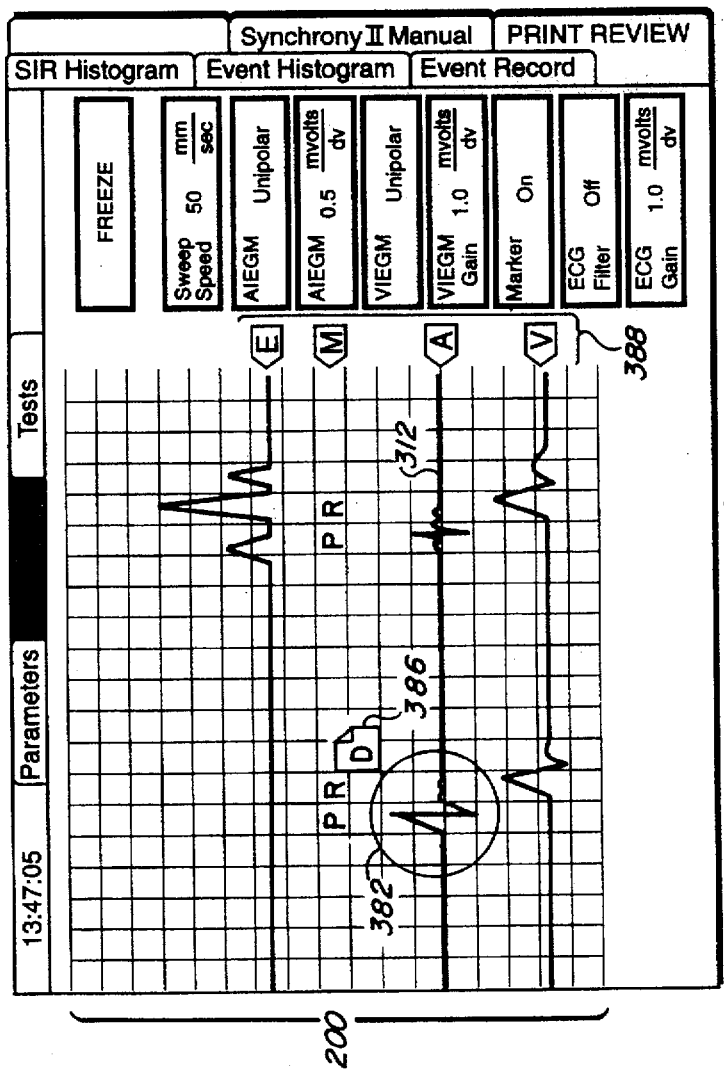
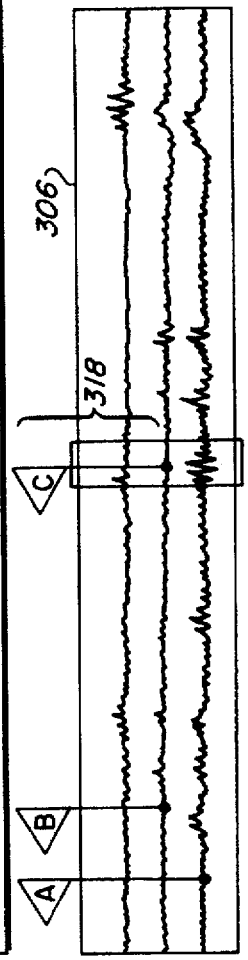
FIG-21

MODEL: 2002L  SERIAL: 0616    REQUESTED ON: Feb 17 1993  1:38pm
PATIENT: Jonathan Doe         DOCTOR: Dr. Marry Wright

| PROCEDURE: Initial Interrogate | | 2:1 Block Rate at 133 ppm |
|---|---|---|
| MODE: DDDR/MAGNET: OFF | RATE: 70 ppm | MAX TRACK RATE: 110 ppm |
| SENSOR: On | MAX SENSOR RATE: 110 ppm | A-V DELAY: 175 msec |
| V REFRACTORY: 250 msec | A REFRACTORY: 275 msec | VENT. SAFETY OPTION: Enable |
| PVC OPTIONS: Normal DDD | RATE RESPONSIVE AV DELAY: Enable | |

ECG // IEGM PARAMETERS

| Surface ECG: | ON (LEAD I) | A IEGM: | UNIPOLAR |
|---|---|---|---|
| Surface ECG Gain: | 1.0 mv/dv | A IEGM GAIN: | 0.5 mv/dv |
| Surface ECG Filter: | ON | V IEGM: | UNIPOLAR |
| Sweep Speed: | 50 mm/sec | V IEGM GAIN: | 1.0 mv/dv |

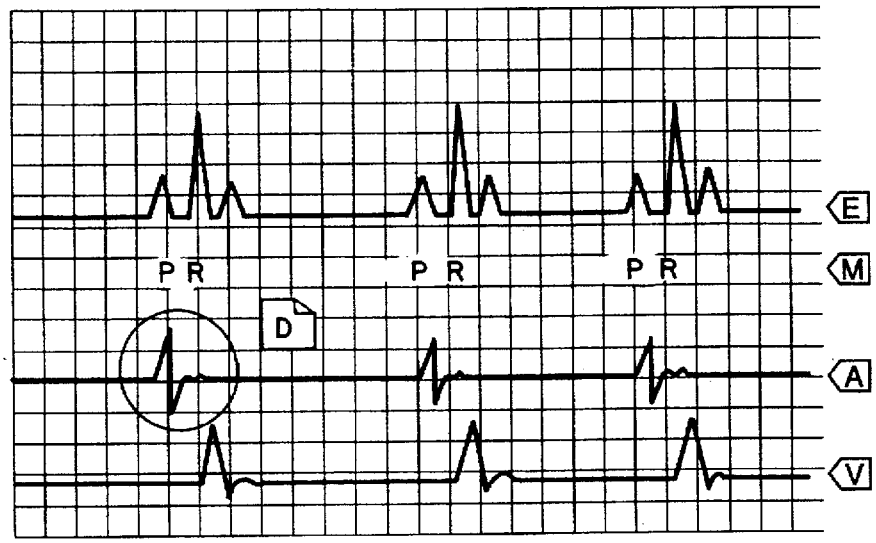

2002L-0616    17-FEB-93
Request Time:  13:38:43

*One A/EGM pulse had an unusually high voltage differential. ($\Delta \approx 1\ 1/2\ mv$)*

FIG. 24

MODEL: 2002L   SERIAL:0616    REQUESTED ON: Feb 17, 1993 1:48 pm  *412*
PATIENT: Jonathan Doe          DOCTOR: Dr. Marry Wright PROCEDURE                      PAGE: 1 of 22 pages
START TIME: FEB 17, 1993       1:46:15 pm DURATION 2 minutes  *414*

| | | |
|---|---|---|
| MODE: | DDDR | ECG FILTER:      OFF |
| RATE: | 70 ppm | ECG CONFIGURATION LEAD 1 |
| AV DELAY: | 175 msec | *418* |
| MAX TRACK RATE: | 110 ppm | |
| VENT PULSE POLARITY: | UNIPOLAR | |
|   PULSE WIDTH: | 0.6 msec | |
|   PULSE AMPLITUDE: | 4.5 volts | |
|   SENSE POLARITY: | UNIPOLAR TIP | |
|   SENSITIVITY: | 2.0 mvolts | |
|   REFRACTORY: | 250 msec | |
| ATRIAL PULSE POLARITY: | UNIPOLAR | |
|   PULSE WIDTH: | 0.6 msec | *416*  *410* |
|   PULSE AMPLITUDE: | 4.0 volts | |
|   SENSE POLARITY: | UNIPOLAR TIP | |
|   SENSITIVITY: | 1.0 mvolts | |
|   REFRACTORY: | 275 msec | |
| BLANKING PERIOD: | 38 msec | |
| VENT SAFETY OPTION: | ENABLE | |
| PVC OPTIONS: | NORMAL DDD | |
| PMT OPTIONS: | 10 BEATS > 110 | |
| RATE RESPONSE AV DELAY: | ENABLE | |
| SENSOR: | ON | |
|   THRESHOLD: | 5.0 | |
|   MEASURED AVERAGE: | 3.5 | |
|   SLOPE: | 8 (normal) | |
|   MAX SENSOR RATE: | 110 ppm | |
|   REACTION TIME: | FAST | |
|   RECOVERY TIME: | MEDIUM | |

FIG. 25

PRINT QUEUE MENU

| | MODEL-SERIAL PROCEDURE | DATE TIME | PRINTER | TYPE REPORT |
|---|---|---|---|---|
| 1) | 2008L-07222-17-FEB-93 V- capture threshold | 09:35:43 am | (John B. Goode) INTERNAL | FULL |
| DEL | V- capture threshold | 09:35:58 am | LASER | SUMMARY |
| 3) | A- capture threshold | 09:53:12 am | LASER | SUMMARY |
| 4) | V- sensitivity test | 10:01:07 am | LASER | SUMMARY |
| 5) | SIR Histogram | 10:01:42 am | LASER | SUMMARY |
| 6) | Measured Data | 10:02:19 am | LASER | SUMMARY |
| 1) | 2005T-00144- Initial Interrogate | 17-FEB-93 10:24:34 am | (MARY P. PAULLETE) LASER | SUMMARY |
| 1) | 2005T-00109- Initial Interrogate | 17-FEB-93 10:55:31 am | (no match on ##) LASER | SUMMARY |
| 1) | 2002L-0616- Initial Interrogate | 17-FEB-93 1:48:15 pm | (JONATHAN DOE) LASER | FULL |

492   436   438   440

(442) PREVIEW    (490) DELETE    (496) CLOSE

*FIG. 27*

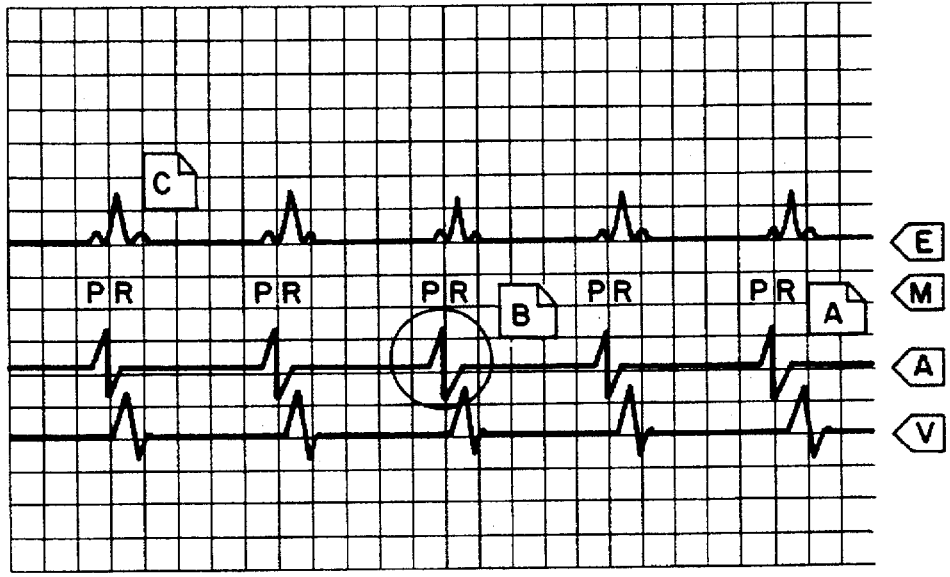
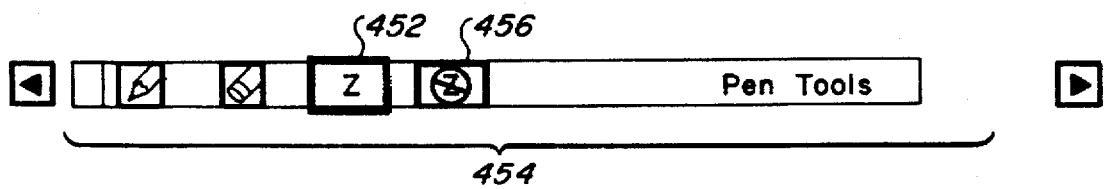
FIG. 29

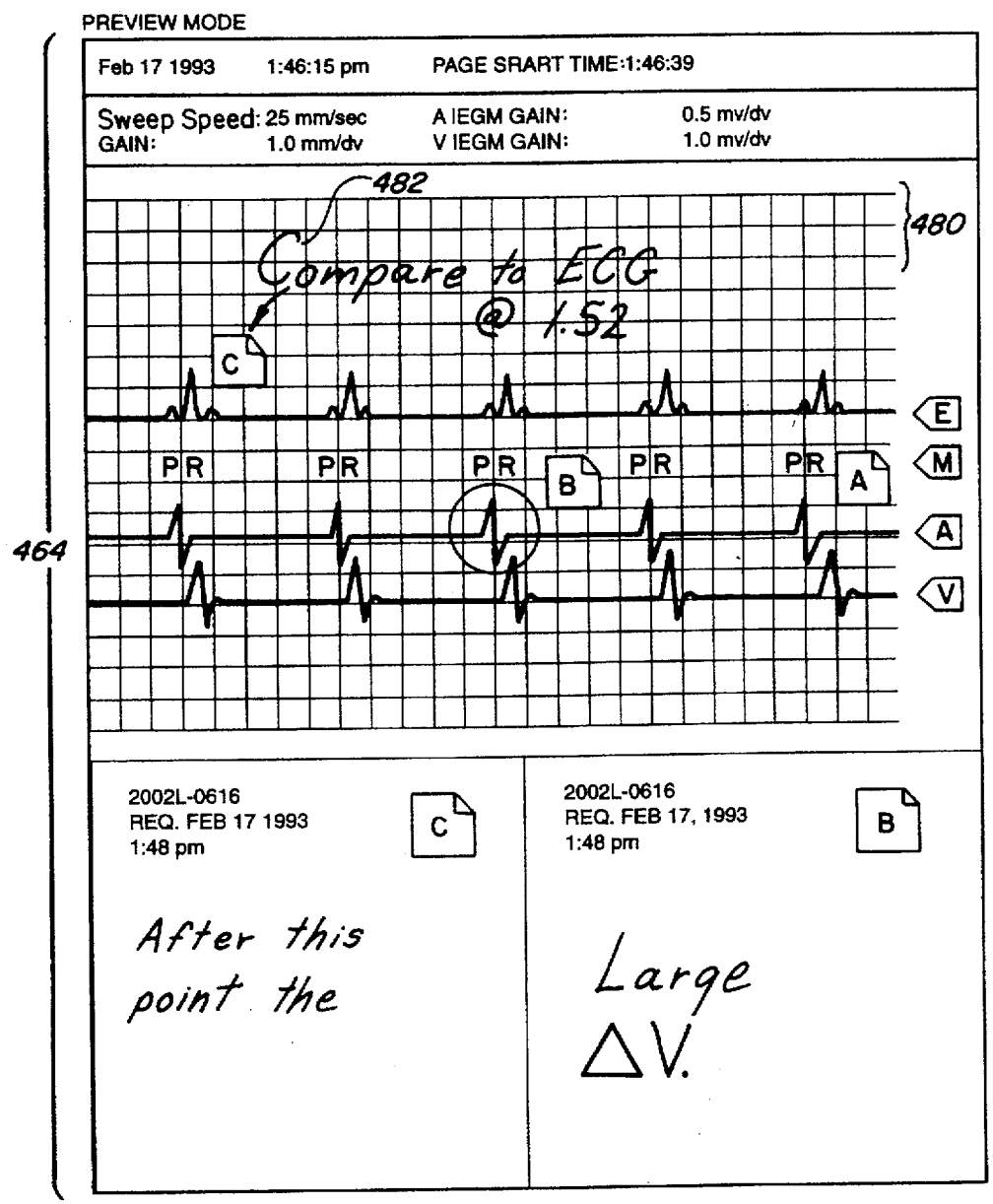
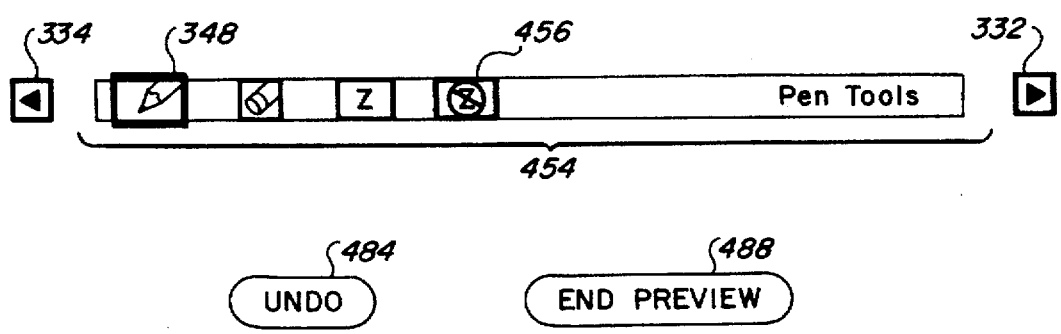
FIG. 31

SAVE CATALOG MENU

| MODEL | SERIAL | DATE | TIME | PATIENT NAME |
|---|---|---|---|---|
| 1) 2008L - | 14460 - | 15-FEB-93 | 01:47:53pm | (Earl E. Byrd) |
| 2) 2008L - | 07222 - | 17-FEB-93 | 09:42:41am | (John B. Goode) |
| 3) 2008L - | 07222 - | 17-FEB-93 | 09:48:31am | (John B. Goode) |
| 4) 2005T - | 00144 - | 17-FEB-93 | 10:39:34am | (Mary P. Paullette) |
| 5) 2005T - | 00109 - | 17-FEB-93 | 10:56:06am | (no match on ##) |

( REVIEW )  ( DELETE )  ( CLOSE )

*FIG. 32*

QUESTIONNAIRE SELECTION MENU

510 {
Initial Visit
Quarterly Check-up
Annual Check-up
Diagnostic Questionnaire
Special Questionnaire 1
Special Questionnaire 2
}

( INPUT )  ( REVIEW RESPONSE )  ( CLOSE )

*FIG. 34*

| MODEL | SERIAL | |
|---|---|---|
| 0XX0 ABC | X0000 | 528 BACK |
| 1111 DEF | 11111 | 526 NEXT |
| X222 GHI | 22XXX | 530 CLEAR |
| 3333 JKX | 33333 | 524 |
| 4444 MNO | 44444 | 532 CLOSE |
| 5555 PQR | 55555 | |
| 6666 STU | 66666 | |
| 7777 VWX | 7X777 | |
| 888X XYZ | 88888 | |
| 9999 | 99999 | |

I feel fatigue when...

|  | Always | Sometimes | Never | N/A | Don't Know |
|---|---|---|---|---|---|
| 1...I wake up | | X | | | |
| 2...I climb stairs | X | | | | |
| 3...I walk on level ground | | X | | | |
| 4...I eat | | X | | | |
| 5...I watch TV | | | X | | |
| 6...I exercise | | | | X | |
| 7...I drive the car | | | | X | |
| 8...I do house work | | | | | X |
| 9...I do yard work | X | | | | |

10. On a scale of 0 to 100 with 100 being the best you have ever felt.

I feel 0 |————————————X————————|100  } 522

2008L-07222

1 = Sometimes
2 = Always

3 = Always
4 = Sometimes
5 = Never
6 = N/A
7 = N/A
8 = Don't know
9 = Always

USER INTERFACE FOR AN IMPLANTABLE MEDICAL DEVICE USING AN INTEGRATED DIGITIZER DISPLAY SCREEN

BACKGROUND OF THE INVENTION

This invention relates to implantable medical devices and particularly to implantable cardiac stimulating devices, including implantable cardiac pacemakers and implantable cardiac defibrillators, as well as implantable cardioverters and cardioverter/defibrillators. More particularly, this invention relates to an improved user interface for an analyzer-programmer computer that is used to monitor and alter the performance of such implantable medical devices.

Implantable cardiac stimulating devices which provide therapy in response to a variety of pathological cardiac arrhythmias are known. For example, an implantable cardiac stimulating device may be capable of detecting a pathological cardiac arrhythmia, and responding to the detected arrhythmia by providing therapeutic electrical stimulation. Implantable cardiac stimulating devices may be capable of providing "tiered therapy," in which the type of electrical stimulation supplied by the device is determined in accordance with the severity of the arrhythmia, with more aggressive therapy being applied in response to more severe arrhythmias.

Effective delivery of therapy from an implantable cardiac stimulating device depends upon the accurate detection of potentially malignant cardiac arrhythmias. Thus, any implantable medical device capable of providing electrical stimulation therapy in response to cardiac arrhythmias must also be capable of detecting the presence of such arrhythmias, and if capable of providing tiered therapy, characterizing the severity of such arrhythmias, before applying the appropriate form of electrical stimulation.

The propagation of the coordinated series of muscle cell contractions that constitute a heartbeat involves a complex combination of electrical and chemical activity involving discrete regions of the heart. These separate but related activities must be coordinated and synchronized. The implantable cardiac stimulating device must be capable of discerning significant deviations from the normal pattern of synchronized activity in the heart. For many types of therapy, the implantable cardiac stimulating device must also be capable of applying the therapeutic electrical stimulation to the heart at the appropriate time in the sequence of activities within the heart rhythm. Therapeutic electrical stimulation that is not properly timed may be ineffective if many of the heart cells are in a refractory period and thus highly resistant or incapable of responding to stimulation. Alternatively, an ill-timed stimulation could cause the contraction of heart muscle fiber out of sequence and in opposition to the coordinated mechanical pumping action of the heart.

Many implantable cardiac stimulating devices serve the patient for years. During these years of service, important changes occur. These include changes in characteristics of the patient's health problem, changes in the characteristics of the tissue adjacent to the implantable cardiac stimulating device, changes in the characteristics of the implantable cardiac stimulating device such as remaining strength of the implanted battery, and changes in medical knowledge about cardiac arrhythmias and the preferred therapies for such arrhythmias.

With every beat of the patient's heart, the implantable cardiac stimulating device makes decisions as to whether electrical stimulation is necessary and what type of electrical stimulation to apply. This decision requires analysis of medical data gathered in real-time and compared against standards contained in a computer program executed by a processor within the implantable cardiac stimulating device.

The computer program carries out orders given by the patient's physician. These orders are tailored by the physician for a particular patient based upon the physician's training and experience. Thus, the computer program is not an unalterable set of instructions burned into the implantable cardiac stimulating device at the time of manufacture. Note the term physician is used in this application to include veterinarian and the term patient includes both humans and animal patients.

Typically, a specialized computer called an analyzer-programmer communicates telemetrically with the implantable cardiac stimulating device and allows a physician to analyze the situation and personally reset the programming parameters of the implantable cardiac stimulating device, or allows another medical specialist to do so at the request of the physician. The physician must be able to customize the programming parameters as part of the procedure to implant the implantable cardiac stimulating device. After the device is implanted, the physician must be able to monitor the performance of the patient's heart, the implantable cardiac device's recognition and characterization of the sinus rhythm, the implantable cardiac device's choice and timing of therapeutic electrical stimulation, and the reaction of the patient's heart to the therapy.

To accomplish such programming and monitoring, the implantable cardiac stimulating device is capable of receiving and transmitting information from its implanted location to a telemetry head placed on or near the surface of the patient's body. The process of evaluating the performance of the implanted cardiac stimulating device typically involves the comparison of atrial intracardiac electrograms (AIEGMs) and ventricular intracardiac electrograms (VIEGMs) telemetered out to the analyzer-programmer from the implantable cardiac stimulating device. The AIEGM and VIEGM are sources of information for use by the implantable cardiac stimulating device in monitoring the heart.

U.S. Pat. No. 4,596,255 ("the '255 patent") describes the use of a marker data channel to chronicle the series of events recognized by the implantable cardiac stimulating device. These events include characterizations of the sensed data from the patient's heart and from application of therapeutic electrical stimulations by the implantable cardiac stimulating device. The implantable cardiac stimulating device is also capable of storing medical data and later transmitting this stored medical data via the telemetry link for display and analysis in the programmer. The implantable cardiac stimulating device could also provide the programmer with a complete list of the current device program parameters. In addition to the information from the implantable cardiac stimulating device, the physician would often wish to view an electrocardiogram (ECG) which is a measurement of the electrical activity of the heart as measured by a series of leads attached to the skin of the patient. This ECG is often called a surface ECG to clearly distinguish it from the IEGM measurements taken internally.

The synchronized display of telemetered marker data channel information with surface ECG readings is described in the '255 patent. The synchronized display of marker data channel, surface ECG and IEGM data is described in U.S. Pat. No. 4,809,697 ("the '697 patent").

The '697 patent further discloses analyzer-programmer enhancements that facilitate communications with implantable medical devices and make analysis of the operation of the implantable medical device easier to understand and perform.

The '697 patent describes an analyzer-programmer implemented on a computer with a touchscreen. The touchscreen is described as a touch-sensitive key pad that fits over the CRT display thereby allowing the system to be entirely "menu driven." The user navigates from one screen to another and effects changes by touching identified regions of the display. Touching the "display," which is an output device, has no impact on the computer program within the analyzer-programmer. However, the act of touching the display causes the transparent touchscreen to send coordinates of the finger contact. These coordinates are input to the computer program in the analyzer-programmer. Essentially, there is a discrete trigger region or button on the touchscreen and corresponding image on the display to indicate the purpose and location of each button.

An advantage of the user interface of the '697 patent is a menu driven system that allows physician or medical specialists to use the system without learning a long list of obscure commands. Simplicity of use is important for an analyzer-programmer. Because the analyzer-programmer should be an aid to the physician or medical specialist, the user interface should not be burdensome to learn and use.

Ease-of-use of an analyzer-programmer is very important for several reasons.

1) The physician or medical specialist may use the analyzer-programmer only a few hours a week or a month.

2) The physician or medical specialist must use the analyzer-programmer while working with a patient and simultaneously analyzing the heart and implanted medical device.

3) The physician or medical specialist may need to use the analyzer-programmer to intervene in an emergency or other high stress situation.

4) The physician or medical specialist cannot be expected to spend extensive time in training classes or practicing using the analyzer-programmer.

Although the analyzer-programmer described in the '697 patent was an advance, the touchscreen used by that analyzer-programmer has a number of limitations. One limitation is the minimum size of a button. The touchscreen must accommodate the relatively broad area of a fingertip and thus needs to be several times the size of a finger tip.

The large button sizes precludes large numbers of buttons on a single menu. If the button size could be reduced, then menus could offer more choices on a given menu. More choices per menu allows fewer menu levels and consequently fewer steps to accomplish a given task. Additionally, smaller buttons allow presentation of all possible values for a given parameter rather than requiring the physician or medical specialist to execute a series of increments and decrements to select a given parameter value.

Light pens could be used as an input device rather than touch screens. Light pens allow smaller input buttons, but light pens have their own disadvantages. One disadvantage is fatigue experienced by the physician or medical specialist from holding the light pen in the awkward position necessary for the light pen to function. The awkward position is a consequence of the operation of a light pen. Light pens take advantage of the way a CRT (cathode ray tube) operates. In a CRT, electrons are continuously applied one after another to each successive location on the CRT. Light pens must be positioned substantially perpendicular to the CRT screen in order to capture an electron fired through the display screen. The location of the light pen on the CRT screen is calculated by a comparison of the time of capture of an electron by the light pen and the times of delivery of electrons to each location on the CRT.

The second disadvantage of a light pen is the reliance on a CRT. The size, weight, and power requirements of a CRT screen make CRTs impractical for use in a hand-held analyzer-programmer. A third disadvantage of light pens is the difficulty in using a light pen to input free-form text, symbols, or diagrams.

A keyboard is another possible input device, but keyboards have disadvantages as well. Keyboards are inconvenient for physicians or medical specialists who cannot type. Keyboards are inconvenient for even those who can type, if the physician or medical specialist is frequently moving his or her hands off of the home keys of the keyboard. Although keyboards can be incorporated into laptop computers, mobility is limited because it is awkward to use a keyboard while standing or walking. With special software and training, a physician or medical specialist could use a keyboard to do such tasks as enter Greek letters which are common in scientific writing, enclose text in a box, or create crude drawings by moving the cursor with the keyboard. However, the keyboard does not allow for free-form entry of symbols on diagrams.

Another problem with keyboards is the difficulty in using the keyboard to position the cursor on the display screen. Other input devices such as a mouse or roller ball can be used in conjunction with the keyboard to overcome the difficulty in moving the cursor, but using a combination of devices makes the system less mobile. Some physicians and medical specialists may find cumbersome the movement of the hand from the home keys to the mouse or roller ball and back to the home keys. Even with the addition of the mouse or roller ball, it is not possible to enter free-form text, symbols, and diagrams.

Physicians and medical specialists perform some medical analyses by printing a copy of medical data and then writing on the printed copy while analyzing the medical data. The written record from the analysis along with annotations of the underlying medical data are sometimes saved with the patient's records. Some instruments have internal printers, thus making it possible for the physician or medical specialist to analyze or annotate a printed copy of medical data during the examination. If the printed record is a long scroll of paper or a multipage report, the physician or medical specialist can add a paper clip or other type of marker to the printed record. Such markers help the physician or medical specialist return to portions of the data that are of particular interest.

There are, however, a number of potential disadvantages to marking paper printouts of medical data as a method of recording the analytical steps taken by a physician or medical specialist. Pieces of paper with important analyses may not be adequately labeled with the name of the patient, the name of the physician or medical specialist, the time, the date, and the name of the procedural step. Lacking such identification, the pieces of paper may not be filed at all, be filed in the wrong patient's folder, or be filed out of sequence.

In addition to identifying the paper for filing, the context needs to be preserved. The context is the situation under which the medical data was collected, which is necessary to understand some types of medical data. The information necessary to establish context includes the settings of the implantable medical device, the settings of the test equipment, and the medical test being performed. Thus, preserving context can require recording a significant amount of information. Recording context is important because annotations that had meaning in context may be ambiguous or misleading when reviewed years later without benefit of that context. However, requiring the physician or medical specialist to record the information necessary to preserve the context is both cumbersome and a possible source of a transcription error.

A separate disadvantage exists for annotations written on the only copy of medical test results. Although annotations are useful to highlight data and to record reasoning, extensive annotations and extraneous marks from analyses may be viewed as distracting clutter by a subsequent physician or medical specialist wishing to review the medical data, or wishing to write new annotations on the data.

Another disadvantage of printing and then annotating the printed copy of medical data is immobility. A system that requires printing of data before annotation is only as mobile as the printer. Other problems associated with printing before annotating include waiting for printout to be printed and keeping a multipage printout organized while annotating a portion of it. One final problem with having to print the data before annotating is that pagination of the multipage printout occurs before the annotations are added. Consequently, unless each page of printout contains extensive space for comments, there is typically insufficient space to extensively annotate a page of special interest.

An input device that overcomes many of the limitations of other input devices is a digitizer pen which is a pen-shaped input device for a digitizer. The digitizer pen can be used to place annotation text, symbols, and diagrams on a digitizer for input to a analyzer-programmer computer. The input can be modified by adding or erasing information. The pen-shape of the digitizer pen allows the physician or medical specialist to use existing fine motor skills and thereby reduces both the time needed to learn to use the digitizer pen and the fatigue from using an input device. The digitizer pen working in conjunction with an analyzer-programmer computer could combine many of the advantages of annotating a paper copy of medical records with a computer's ability to manipulate and store electronic data. Such a combination could surpass the capabilities of analyzer-programmer computers based on prior input devices for many of the actions involved with analyzing and programming implantable cardiac stimulating devices.

SUMMARY OF THE INVENTION

The present invention provides an improved apparatus and method for viewing, manipulating, and annotating both real-time and stored medical data. The present invention combines the desirable attributes of pencil and paper with the desirable attributes of various computer input devices.

The present invention combines a tablet computer and a digitizer pen with other hardware and a user interface to take advantage of the desirable attributes of a pen-based system. The present invention provides a tablet computer that is preferably adapted to receive, display, manipulate, store, and request printing of medical data. The tablet computer is adapted to communicate with implantable medical devices such as implantable cardiac pacemakers, implantable cardiac defibrillators, implantable cardioverters, or implantable cardioverter/defibrillators. The tablet computer preferably receives several channels of medical data from an implantable medical device, some which may be real-time data and some which may be recorded data.

The tablet computer can also be used to communicate commands to the implantable medical device, including changes to the computer programs used by the implantable medical devices. The user interface for an analyzer-programmer tablet computer of the present invention assists the physician (and any medical specialist aiding the physician) in monitoring and adjusting the implantable medical device. The work typically includes one or more cycles of collecting medical data, analyzing the medical data, adjusting the settings of the implantable medical device, sending the adjusted settings to the implantable medical device, and collecting medical data after the adjusted settings are sent and implemented.

The tablet computer is preferably also adapted to receive medical data from an ECG machine. The ECG forms another channel of medical data that can be displayed with the channels from the implantable medical device.

Periodically the tablet computer can be inserted into a base station. While inserted into the base station, the tablet computer can send previously queued print requests to one of the printers attached to the base station. While attached to the base station, the tablet computer can exchange data files with other computers connected to the base station.

The tablet computer is preferably designed to be used while unattached to the base station. With the exception of a few emergency keys on the tablet computer, input to the tablet computer preferably comes from a digitizer pen which is a pen-shaped device that is recognized by a tablet computer digitizer. In the preferred embodiment, the tablet computer digitizer is covered by a tablet computer display such that the two components appear as one integrated component known as a digitizer display screen. The integrated digitizer display screen allows the person using the tablet computer to tap or write on the display and have this input received by the digitizer behind the display.

A user interface and methods of using the tablet computer are provided by the present disclosure. The digitizer pen is used to alter programming parameters of the implantable medical device by tapping on images of buttons that appear on the display screen over discrete regions of the digitizer.

The user interface allows the physician or medical specialist to use the tablet computer to manipulate digitized scrolls of analog data. The digitized scrolls preferably contain one or two minutes of medical measurements, while the display screen can only show several seconds of data at the preferred level of magnification. The user interface provides a variety of tools that allow a physician or medical specialist to move within the lengthy scroll of data. A related feature of the user interface is the compressed buffer overview which shows an image of the entire scroll of data, to help the physician or medical specialist locate certain segments of the data scroll.

The user interface supports several methods of adding handwritten annotations as overlays to the medical data and the various reports. The annotations are kept separate from the medical data or the reports so that the annotation can be deleted without harming the underlying data or report.

The annotations can preferably be written over the displayed medical data or attached to the segment of medical data as a footnote. Medical data can preferably be stored for future display and annotation. A variety of reports can preferably be requested. Where appropriate, reports will contain all of the annotations that were added to the medical data. A separate feature preferably allows the image of the queued report to be annotated. Thus a physician or medical specialist can preferably add handwritten comments to a report before the report is sent to a printer.

These annotation features preferably make it possible for the physician or medical specialist to include all comments, diagrams, and highlighting symbols in the electronic version of the patients records, thus allowing the physician or medical specialist to be highly mobile while providing a method to collect and store annotations accurately and in context.

The annotation features preferably work with the compressed buffer overview to leave marker flags on the compressed buffer overview. The user interface facilitates the physician's or medical specialist's return to the segments of data that are annotated by supporting commands that allow the physician or medical specialist to "jump" to the next annotation marker flag.

Another aspect of the user interface is the preferable use of a questionnaire card to capture patient responses to a list of questions. The completed questionnaire card is placed over the surface of the digitizer display. The patient answers are then transferred to the tablet computer by tapping the pen on the marked responses.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 6 is a screen display on the digitizer display screen having the ECG machine controls window open in the upper window with an ECG machine controls pop-up window open for selection of a new sweep speed;

FIG. 13 is a screen display on the digitizer display screen after the inadvertent attachment of the connection point to marker data channel information;

FIG. 21 is a portion of a screen display on the digitizer display screen containing a frozen data scroll with an ink annotation and a footnote marker;

FIG. 24 is a summary report for a segment of a frozen data scroll with a footnote annotation;

FIG. 25 is a first page of a full report containing a print header, a parameter header, and a full set of device program parameters for an implantable medical device;

FIG. 27 is a screen display on the digitizer display screen used to manage the queued print requests;

FIG. 29 is a screen display on a digitizer display screen for preview of a page of a full report of a data scroll;

FIG. 31 is a screen display on the digitizer display screen containing a page image of a page from a full report;

FIG. 32 is a screen display on the display digitizer screen used to manage previously saved sets of screen displays and medical data;

FIG. 34 is a screen display on the digitizer display screen used to select a series of input screen displays that correspond to a particular series of questionnaire cards;

FIG. 35 is a screen display on a digitizer display screen partially covered by a questionnaire card and displaying the answers received by the tablet computer;

DERAILED DESCRIPTION OF THE PREFERRED EMBODIMENT

The present invention uses a modified tablet computer and a user interface for entering and manipulating information in a computer which accepts input from a pen. The preferred embodiment uses this pen as the primary input device for the tablet computer. Although the invention disclosed is useful in a variety of applications, the preferred embodiment is adapted to a tablet computer that is used to view, manipulate, and annotate medical data. More specifically, the medical data is information useful in monitoring the functioning of a heart and of an implantable medical device such as a pacemaker or defibrillator. The preferred embodiment of the present invention is described in the context of a highly portable tablet computer used by physicians or medical specialists to monitor the performance of the patient's heart and interrogate the implantable medical device. The physician or medical specialist can also use this specialized tablet computer to modify the instructions and settings of some implantable medical devices which are programmable. Although the description presumes that the implantable medical device is indeed implanted in a patient, the tablet computer can be used to interrogate and load program information into an implantable medical device before the device is implanted in a patient. The tablet computer can also be used to analyze stored data or the tablet computer could be connected to an appropriate simulator or test device for testing implantable medical devices.

The present invention allows the physician or medical specialist to record annotations on the various types of medical data for printing or storing in a memory device. The terms "annotate," "annotation" and "write," as used herein and in the claims which follow, include all marks that can be made with a pencil on a piece of paper. In addition to alphanumeric characters in all languages, these terms include, for example, arrows, circles, stars, other symbols, drawings, and graphs. "Write," "annotate," and "annotation" apply to marks made during analysis, as well as marks made to highlight or comment upon data. Unless otherwise specified, the term "pen" is used herein and in the claims which follow to indicate an input device to a digitizer associated with a display screen. The actual device used as the "pen" will vary depending on the type of digitizer associated with a display screen. The pen can of the type that emits radio frequency or ultrasonic signals. The pen can be a passive stylus if the digitizer is a pressure sensitive digitizer. Although not the preferred embodiment, the pen can even be of the type that is connected to the digitizer by one or more conductive wires.

Figure 1:
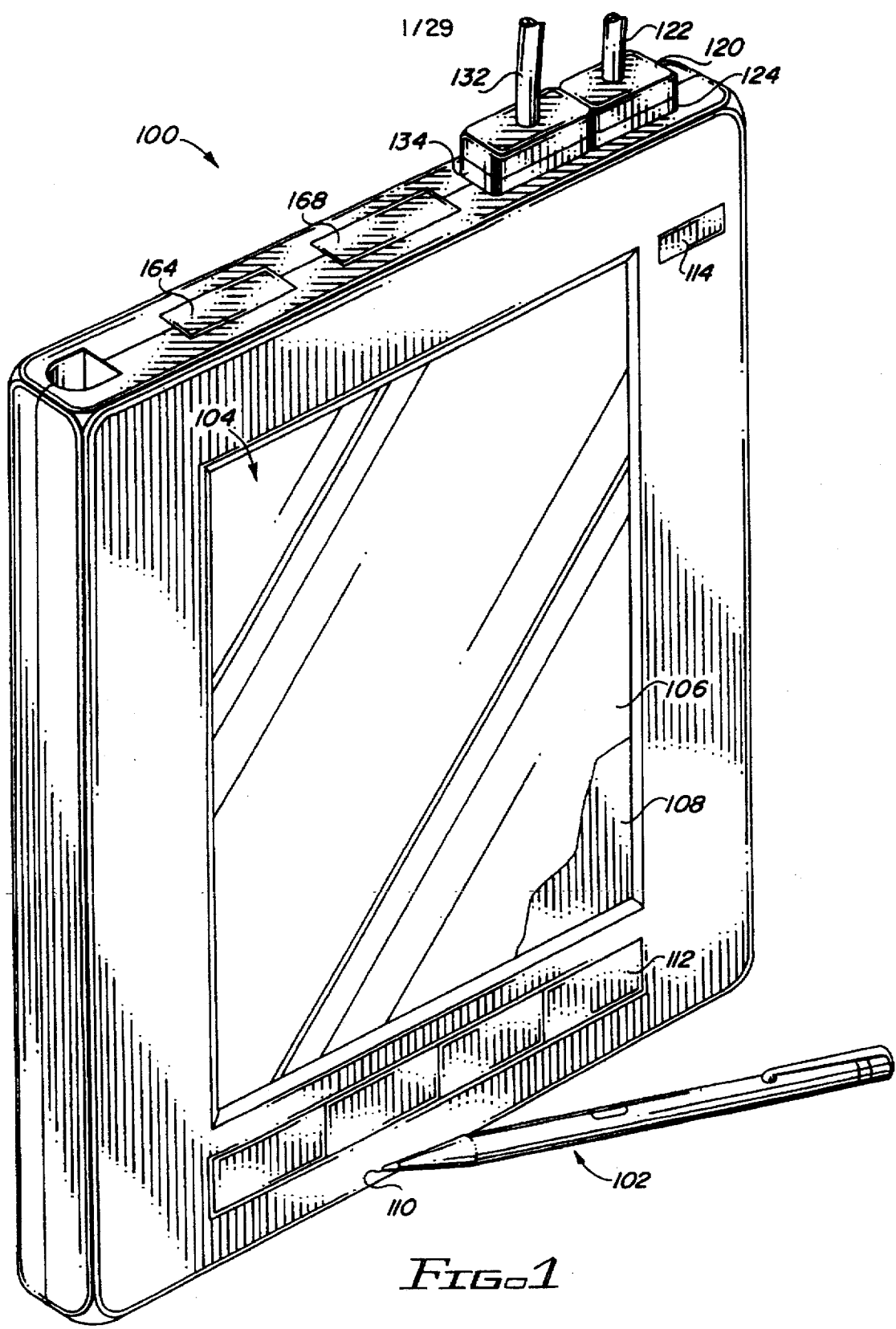
FIG. 1 is a perspective view of a preferred embodiment of a tablet computer according to the invention.

Referring to FIG. 1, a tablet computer 100, and a pen 102 for inputting information are shown along with components of the tablet computer. The pen 102 can be used to write, draw, or select among presented choices. The pen 102 is effective on a digitizer display screen 104. The digitizer display screen 104 comprises the majority of the front face of the tablet computer 100. The digitizer display screen 104 is comprised of a display 106 and a digitizer 108 which overlap one another. In the preferred embodiment the digitizer 108 is underneath the display 106 but the concepts of this invention would be unchanged if the display 106 were covered by a transparent digitizer 108. The term "underneath" and the phrase "on the surface over" shall be used to describe the corresponding positions of the digitizer 108 and the display 106, respectively. The terms "above" and "below" will be used to describe position in the plane of the display 106 or the digitizer 108.

In the preferred embodiment, the pen 102 can be one of the commercially available pens that alter a radio frequency signal transmitted by the digitizer 108. This altered signal is sensed by the digitizer 108 when the pen 102 is within the sensing range of the digitizer 108. The sensing range is approximately one-quarter inch. Contact of a pen tip 110 with any surface causes a very slight movement of the pen tip 110 back into the body of the pen 102. This depression of the pen tip 110 triggers a switch (not shown) within the pen 102 and changes the way the pen 102 alters the transmitted signal. Typically, the depressed tip signal is used for input and the other pen signal is used as a feedback signal to help the physician or medical specialist place the pen 102. The tablet computer 100 responds to the pen input by causing an image to be displayed on the display 106.

Rather than altering signals from the digitizer 108, the pen 102 could produce two different signals that are received by the digitizer 108. These signals could be ultrasound, radio frequencies or other types of signals. The preferred embodiment uses the different signals from the pen 102, proximity and contact. However, if the pen 102 is not capable of sending a signal to the digitizer 108 unless the pen 102 is in contact with the digitizer display screen 104, then the features of this invention that rely on such proximity signals cannot be implemented. These features can either be omitted or implemented by making minor modifications to the screen displays and sequence of operations in keeping with the teachings of this invention and skills known in the art. For example, if the digitizer 108 is a pressure sensitive digitizer, and the pen 102 is a passive stylus, then the only signal from the pen 102 to the digitizer 108 comes from contact. Thus the tablet computer 100 cannot provide feedback on the display 106 when the pen 102 is in proximity but not in contact with the digitizer display screen 104.

In a particular preferred embodiment of the invention, emergency keys 112 are provided on the tablet computer 100. The emergency keys 112 provide the physician or medical specialist with several important functions for controlling the tablet computer 100 during an emergency. One of the emergency keys 112 may request that the tablet computer 100 send a particular command to the implantable medical device (described below in connection with FIG. 2), or may request action by the tablet computer 100 itself such as a reset of the tablet computer 100 or a request of the tablet computer 100 to display a screen display with information and options that are useful when managing an emergency. The emergency keys 112 allow the physician or medical specialist to intervene quickly even if the pen 102 is misplaced. The emergency keys 112 allow action without the delay inherent in entering the sequence of commands that would otherwise be required to request the tablet computer 100 to display the screen display with the emergency functions.

The tablet computer 100 is powered by a battery (described below in connection with FIG. 2). The tablet computer 100 is turned on and off with an on/off switch 114.

Figure 2:
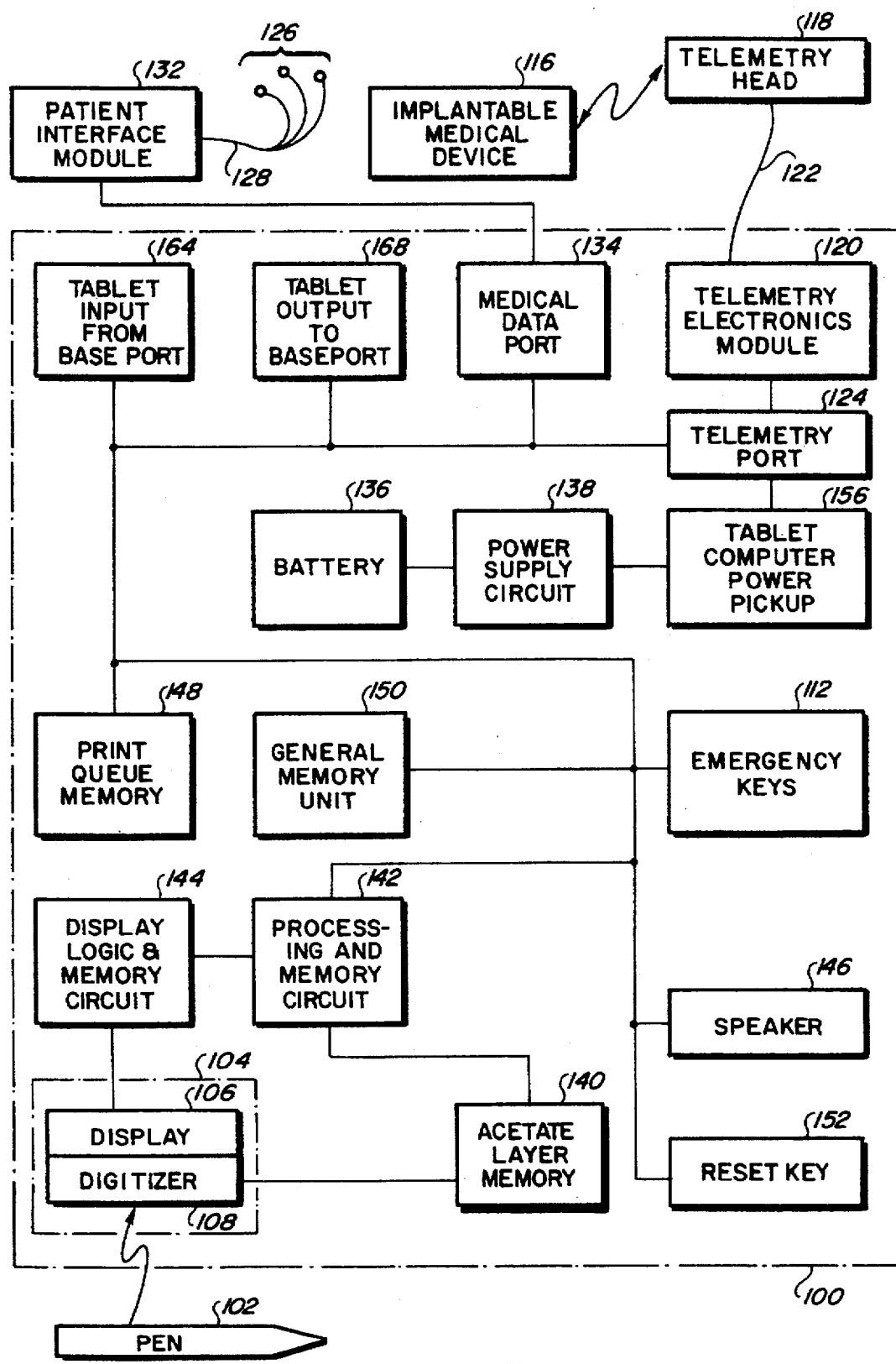
FIG. 2 is a block diagram of the tablet computer of FIG. 1 showing functional elements and showing the sources of input.

Referring now to FIG. 2, an implantable medical device 116 can sense cardiac activity and provide therapeutic electric stimulation through electrical leads (not shown). The information received by the implantable medical device 116 include IEGM waveforms from the atrial and ventricular regions of the heart, and marker data channel information generated within the implantable medical device 116. Marker data channel information contains a record of discrete acts of the implantable medical device 116 such as the application of a therapeutic electric pulse, and also the recognition by the implantable medical device 116 of certain heart activities as sensed by the implantable medical device 116.

The AIEGM measurement information, VIEGM measurement information, marker data channel information, and the time of each measurement and each marker data channel marker can be stored in a limited amount of memory (not shown) within the implantable medical device 116. The current (real-time) or stored medical data in the implantable medical device can be transmitted through the tissue and skin of the patient to a telemetry head 118.

The term "real-time" does not necessarily mean instantaneous. The term is in contrast with "batch processed" information. "Real-time" refers to a system that controls an ongoing process and delivers the output not later than the time that it is needed for effective control. Thus, the cardiac data is real-time data (or current data) even if the various processing steps introduce a delay between a cardiac event and the display of the cardiac information.

The telemetry head 118 is attached to a telemetry electronics module 120 by a telemetry cable 122 which is preferably approximately six feet long. The telemetry electronics module 120 is plugged into a telemetry port 124. (Note that the connection of the telemetry cable 122 into the telemetry electronics module 120 and the telemetry port 124 is also shown in FIG. 1.) The telemetry electronics module 120 performs conversions of the telemetry data such as a conversion from analog data to digital data if the implantable medical device 116 does not itself perform the analog-to-digital conversion. The preferred embodiment uses the same cable and port for telemetry data transmitted in either direction between the tablet computer 100 and the implantable medical device 116. A system (not shown) with an output port on the tablet computer 100 and a cable dedicated to output along one communication path to the telemetry head 118 and having a separate input port on the tablet computer 100 with a separate cable dedicated to input from a separate communication path to the telemetry head 118 could also use the teachings of this invention.

Another channel of medical data can be collected from surface ECG leads 126. The surface ECG leads 126 are placed on the skin of the patient (not shown). A surface ECG cable 128 has a number of strands that preferably can be attached and detached to the surface ECG leads 126. The surface ECG leads 126 are connected via the surface ECG cable 128 to a patient interface module 130 which performs conversion of the surface ECG waveform into digital format and performs other processing of the waveform data. The patient interface module 130 is connected to the tablet computer 100 by a medical data port cable 132 at a medical data port 134. (Note that the connection of the medical data port cable 132 to the medical data port 134 is also shown in FIG. 1.)

In the preferred embodiment, the surface ECG cable 128 is approximately 30 inches long and the medical data port cable 132 is approximately six feet long. Thus, in the preferred embodiment, the patient interface module 130 is placed near the patient or carried by the patient thereby increasing the mobility of the tablet computer 100. During surgery, the physician or medical specialist may use cables of greater length for the telemetry cable 122 and the medical data port cable 132 to position the physician or medical specialist and the tablet computer 100 in a convenient location away from the actual surgery.

The tablet computer 100 is provided with energy during mobile operation by a battery 136 connected to a power supply circuit 138. The digitizer display screen 104 is shown in FIG. 2 in its constituent parts: the digitizer 108 and the display 106. The input from the pen 102 is received by the digitizer 108 and placed in an acetate layer memory 140 where the input is processed in processing and memory circuit 142.

The term acetate layer memory is used to describe a section of memory that stores information that is displayed as an overlay over some other information. Acetate layer memory is so called because the overlay information seems to be stored on a transparent layer of acetate and that can be selectively overlaid over the other information. Thus, the term is descriptive of the function of the memory rather than the type of memory. The processing and memory circuit 142 interprets the input, and then deletes the input from the acetate layer memory 140 and moves a copy of certain input into a display logic and memory circuit 144. The display logic and memory circuit 144 controls the display 106.

A speaker 146 is used within the tablet computer 100 to provide audio alarms in response to detected problems concerning the patient's heart, the monitoring equipment, the input from the physician or medical specialist, or other problems. The speaker 146 can also be used to confirm receipt of input.

The tablet computer 100 contains a print queue memory 148 which stores requests to create printout until the tablet computer 100 is connected directly or indirectly to a printer (described below in connection with FIG. 3). The print queue memory 148 is nonvolatile memory and in the preferred embodiment is a memory card.

In addition to the acetate layer memory 140, the memory in the processing and memory circuit 142, the memory in the display logic and memory circuit 144, and the non-volatile memory in the print queue memory 148 the tablet computer 100 has a general memory unit 150. The general memory unit 150 is preferably used to store patient data and reference material available to the physician or medical specialist such as a dictionary, phone directory, medical reference text, or reference manuals on implantable medical controllers The preferred embodiment uses a conventional hard drive for the general memory unit 150. Alternative choices for the general memory unit include a non-volatile memory card or a read and write optical memory. Another alternative (not shown) is to use a read only memory device to store the reference material. This read only memory would be on a cartridge, optical disk or other easily replaced device so that periodic updates could be made to the reference material.

In addition to the emergency keys 112, a reset key 152 is preferably provided to re-initialize the tablet computer 100. In alternative embodiments, the reset key could be one of the emergency keys 112.

Figure 3:
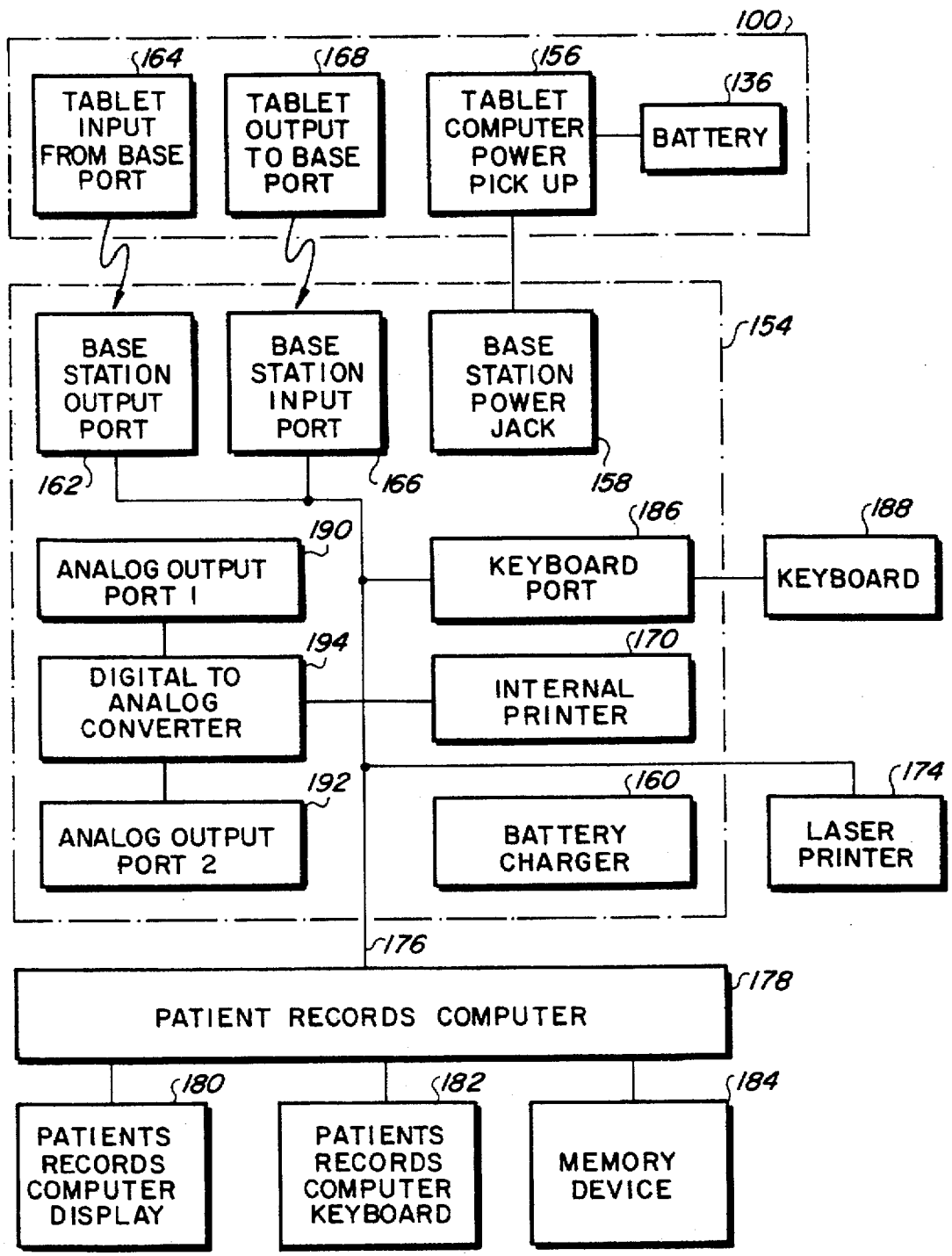
FIG. 3 is a block diagram of the tablet computer of FIGS. 1 and 2, showing the tablet computer connected to a base station, the base station being further connected to a patient records computer and to peripheral devices.

Referring now to FIG. 3, the tablet computer 100 is periodically inserted into a base station 154. A tablet computer power pickup 156 mates with a base station power jack 158 during the insertion of the tablet computer 100 into the base station 154 to provide a source of power to the tablet computer 100 which is sufficient to both operate the tablet computer 100 and to charge the battery 136 in the tablet computer 100. A battery charger 160 is contained in the base station 154 for charging batteries 136 for use in the tablet computer 100. The base station 154 is equipped with conventional power supply circuitry (not shown) connected to line voltage by a line voltage plug (not shown).

The base station 154 and tablet computer 100 have connections that allow the tablet computer 100 to communicate with the base station 154 when inserted in the base station 154. The preferred embodiment uses LEDs (light emitting diodes) for an infrared serial communication link between the tablet computer 100 and the base station 154. Specifically, a base station output port 162 is placed adjacent to a tablet input from base port 164 and a base station input port 166 is placed adjacent to a tablet output to base port 168. These ports are preferably small windows for transmitting the infrared signals. As shown in FIG. 3, small gaps exists between the communication ports (162 to 164 and 166 to 168) as distinguished from the physical contact established between the base station power jack 158 and the tablet computer power pickup 156.

Although conventional physical cable connections could be used, the infrared serial connection is preferred over conventional physical cable connections for two reasons. The first reason is that the infrared connections are not subject to physical wear and tear from the repeated insertion and removal of the tablet computer 100 into the base station 154. The second reason to use infrared connections instead of conventional physical connections is electrical isolation of the tablet computer 100 from other equipment. Electrical isolation is a keen concern in the design of medical equipment because of concerns for patient safety.

The teachings of the present invention can be applied if the tablet computer 100 uses other communication interfaces such as a radio frequency link, a spread spectrum radio frequency link, or a cellular communication link. These alternative forms of communication have an advantage over both infrared and conventional physical connections—the advantage of range. The extended range allows the tablet computer 100 to receive and transmit information with the base station 154 even when not inserted into the base station 154.

Another use of radio frequency communication, spread spectrum radio frequency communication, or cellular communication is the replacement of the surface ECG cable 128 (FIG. 2) or the medical data port cable 134 (FIG. 2) or both cables. This substitution of a wireless communication technology would increase the mobility of the tablet computer 100. Another example of such a substitution of wireless communication for a cable is described in commonly-assigned, copending U.S. patent application Ser. No. 08/510,449, filed concurrently herewith, of Snell and Konopka, titled "SYSTEM AND METHOD FOR AMBULATORY MONITORING AND PROGRAMMING OF AN IMPLANTABLE MEDICAL DEVICE." The invention describes a system for placing the telemetry electronics module 120 with the telemetry head 118 and using a wireless communication link in place of the telemetry cable 122. Thus the communication path would be telemetry head 118 to telemetry electronics module (instead of element 120) though a cable (not shown), then to the telemetry port 124 through a wireless connection and hardware required for the wireless connection. Increased mobility of the system and of the patient relative to the system is valuable, especially in light of the physical activity of a patient during follow up visits to the physician or medical specialist. During such follow-up visits, the patient may climb stairs, perform calisthenics, exercise on a treadmill, or engage in other physical activity.

Returning to the preferred embodiment, an internal printer 170 is integral to the base station 154. The internal printer 170 is preferably a thermal printer. In the preferred embodiment, a laser printer 172 is connected to the base station 154 by a laser printer connection cable 174. The present invention can be extended to include support for other printers (not shown) such as ink jet printers or dot matrix printers with resolutions sufficient to reproduce the medical data.

The base station 154 is at least periodically connected by a base to host cable 176 to a patient's records computer 178. The patient's records computer 178 is connected to a patient's records computer display 180, a patient's records computer keyboard 182, and a memory device 184. The memory device 184 stores medical data records and other information that is relevant to the use of the tablet computer 100.

Other optional connections on the base station 154 include a keyboard port 186 for connecting a keyboard 188 to be used by field service engineers in customizing the tablet computer 100. Although not the preferred embodiment, the keyboard 188 could be used to enter patient data into a tablet computer 100 while the tablet computer 100 is inserted in the base station 154. Another optional attachment is a bar code reader (not shown) which could be connected to the keyboard port 186 to allow bar codes to be scanned. As an example of bar code reader use, some hospitals may position the base station 154 along with the bar code reader into the operating room to read a patient identification bar code number along with the bar code representation of each piece of equipment or material used during the implantation of the implantable medical device 116 (FIG. 2).

Analog output ports 190 and 192 are provided so that other devices can be connected to the base station 154. The medical data provided to the tablet computer 100 through the medical data port 134 (FIG. 2) and the telemetry port 124 (FIG. 2) can be passed through the tablet output to base port 168 to the base station input port 166 and converted into analog form in a digital-to-analog converter 194 before passing out of one of the analog output ports 190 or 192 to peripheral devices such as paper chart recorders (not shown), large video monitors (not shown) for use in teaching, or calibration equipment (not shown).

The base station 154 may become less important as hospitals and other medical facilities incorporate wireless communication ports into the walls. With ready availability of wireless communication ports, the tablet computer 100 could be equipped with appropriate communication ports to use wireless communication to send information to a network printer (not shown) without passing the information through the base station 154. Similarly, the widespread use of wireless communication ports within hospitals and other medical facilities will make it practical for the tablet computer 100 to read or write to network memory devices (not shown) without passing the information through the base station 154. As wireless communication becomes more common, a great range of peripherals could be accessed without use of the base station 154. Eventually, wireless communication will make it feasible for two or more tablet computers 100 to be connected together so that physicians or medical specialists could share medical data and annotations in real time. Such advances would have many benefits and may require minor adjustments to the process for using the tablet computer 100. However, the de-emphasis or even the total replacement of the base station 154 as the path to peripheral devices does not fundamentally alter the use of the teachings of the present invention.

Figure 4:
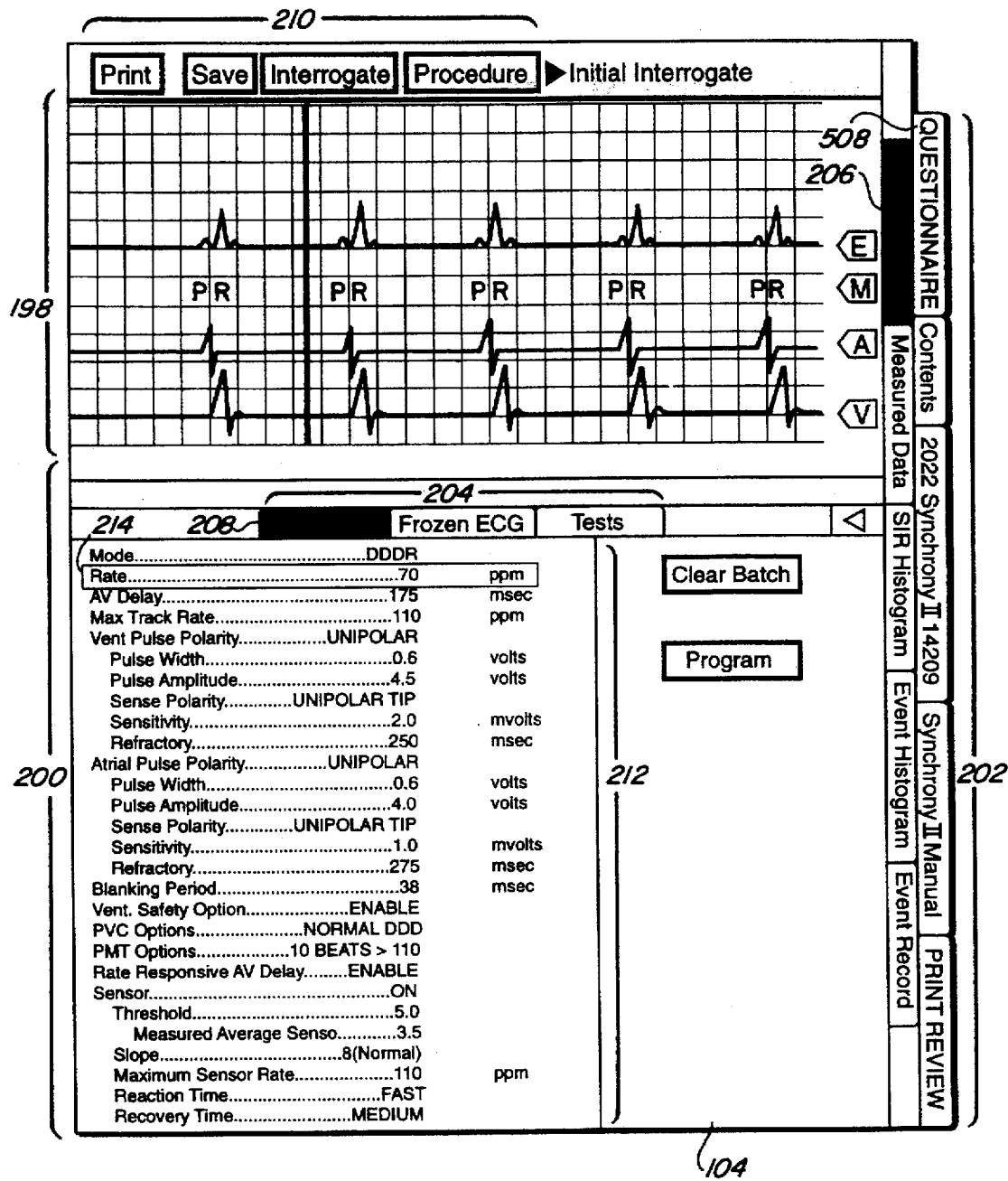
FIG. 4 is a sample screen display on the digitizer display screen of a tablet computer according to the invention.

Turning now to FIG. 4, a view of the digitizer display screen 104 is shown. The tablet computer 100 (FIG. 1) responds when the pen 102 (FIG. 1) taps one of the regions on the digitizer display screen 104 that is a current trigger for action by the tablet computer 100 (FIG. 1). The size, location, and number of regions that act as triggers are controlled by the tablet computer 100 (FIG. 1) and change during the use of the tablet computer 100 (FIG. 1). These regions are called buttons. The digitizer display screen 104 appears to be one component to the physician or medical specialist, but as described in connection with FIGS. 1-2 is actually two distinct components. The buttons exist on the digitizer 108 (FIG. 1) in the display digitizer screen 104, and unlike the input keys on a keyboard, the buttons are invisible to the physician or medical specialist. The tablet computer 100 (FIG. 1) can cause the display 106 (FIG. 1) to provide an image directly overlying the button. The image could be a box with text to indicate to effect of tapping on that button. The combination of input regions and buttons on the digitizer 108 (FIG. 1) and the corresponding image on the display 106 (FIG. 1) containing windows of data and images overlying buttons form a screen display. The remainder of the description will refer to the digitizer display screen 104 or the screen display which is implemented on the digitizer display screen 104 rather than the individual components unless otherwise required for clarity.

In FIG. 4 the screen display has an upper window 198 and a lower window 200. The screen display in FIG. 4 contains vertical tabs 202 and horizontal tabs 204. The physician or medical specialist uses the vertical and horizontal tabs 202 and 204 to move from one screen display to another screen display. Tapping one of the vertical tabs 202 triggers the button on the digitizer display screen 104 underneath the displayed image of the tab. This tapping will cause the tablet computer 100 (FIG. 1) to jump to the first screen display in a series of related screen displays. Vertical tabs 202 are preferably made to resemble tabs on a three-ring binder (not shown). Vertical tabs 202 like tabs on a binder facilitate movement to the selected section.

Individual windows may have horizontal tabs 204. In FIG. 4, the lower window 200 has horizontal tabs 204 to change the lower window 200 without affecting the rest of the screen display. A highlighted vertical tab 206 and a highlighted horizontal tab 208 remind the physician or medical specialist of the context of the current screen display. In this case, the highlighted vertical tab 206 displays the tab labeled "ECG Machine" and the highlighted horizontal tab 208 displays the tab labeled "Parameters."

In this screen display, a series of buttons 210 are above the upper window 198 on the digitizer display screen 104. The series of buttons 210 contain choices such as print or save that are used in a large number of screen displays. The buttons choices are updated by the tablet computer 100 (FIG. 1) to reflect currently valid choices.

The series of buttons 210 can be called explicit buttons. Explicit buttons can be contrasted with implicit buttons such as those found underneath a series of programming parameters 212 in the lower window 200. Tapping the pen 102 (FIG. 1) on one of the programming parameters 212 activates an implicit button to cause a pop-up window (described in connection with FIG. 5) to appear in the lower window 200. The use of implicit buttons allows the screen display to have a great number of buttons without excessive visual clutter. In the preferred embodiment, which uses a type of pen 102 (FIG. 1) that provides a proximity signal to the digitizer 108, a rectangle 214 is displayed as a visual aid for the physician or medical specialist. The rectangle 214 appears when the pen 102 (FIG. 1) is within sensing range of the digitizer display screen 104. The rectangle 214 moves from one implicit button to the next as the pen 102 (FIG. 1) moves. In this case, the rectangle 214 moves up and down the screen display as the pen 102 (FIG. 1) moves up and down the surface of the digitizer display screen 104. The use of the rectangle 214 or other method of highlighting (not shown) allows the physician or medical specialist to accurately select a particular implicit button from among many densely packed implicit buttons.

Figure 5:
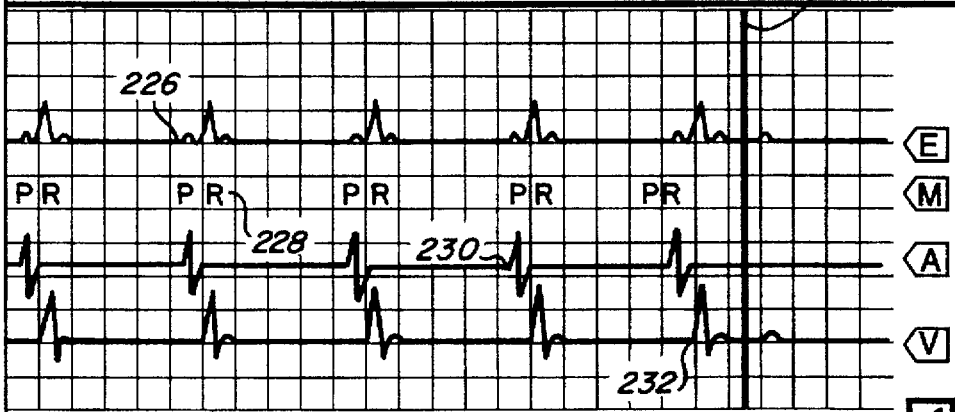
FIG. 5 is a screen display on the digitizer display screen that shows the changes to the display of FIG. 4 caused by the selection of the maximum sensor rate parameter for modification, thus opening a pop-up window with the possible values for maximum sensor rate.

FIG. 5 shows the screen display after the selection of programming parameter "Maximum Sensor Rate" has caused arrowheads 216 to highlight the selected parameter and a pop-up window 218 to appear in the lower window 200. The "Maximum Sensor Rate" can be changed by selecting one of a series of pop-up window choice buttons 220.

The pop-up window 218 is exited without making changes to the computer program for the implantable medical device 116 (FIG. 2) by selecting a close button 222 in the pop-up window 218. Tapping a close and program button 224 within the pop-up window 218 implements the selected changes to a batch file (not shown) which contains the parameter setting changes to be sent to the implantable medical device 116 (FIG. 2). Selection of either the close button 222 or the close and program button 224 will cause the pop-up window 218 to be removed from the screen display. In the preferred mode, changes made to the computer program for the implantable medical device 116 (FIG. 2) are stored within the tablet computer 100 (FIG. 1) until the physician or medical specialist sends all of the changes via the telemetry head 118 (FIG. 2). This is known as batch programming.

When the telemetry head 118 (FIG. 2) is sufficiently close to the implantable medical device 116 (FIG. 2) to establish a telemetry link, the current medical data sensed by the implantable medical device 116 (FIG. 2) can be passed via the telemetry link as described above. In the preferred embodiment, the current measurements of medical data are displayed in the upper window 198 of most screen displays.

Normally, four channels of information will be simultaneously displayed. The four channels are a surface ECG channel 226, a marker data channel 228, an atrial IEGM (AIEGM) channel 230, and a ventricular IEGM (VIEGM) channel 232. The current medical data will be motionless until updated by a left to right sweep of a sweep bar 234.

While current medical data is being displayed in the upper window 198, tapping the pen 102 (FIG. 1) on a window modification button 236 in the upper window 198 reduces the horizontal size of the upper window 198 and opens an ECG machine controls window (described in connection with FIG. 6).

Figure 6:
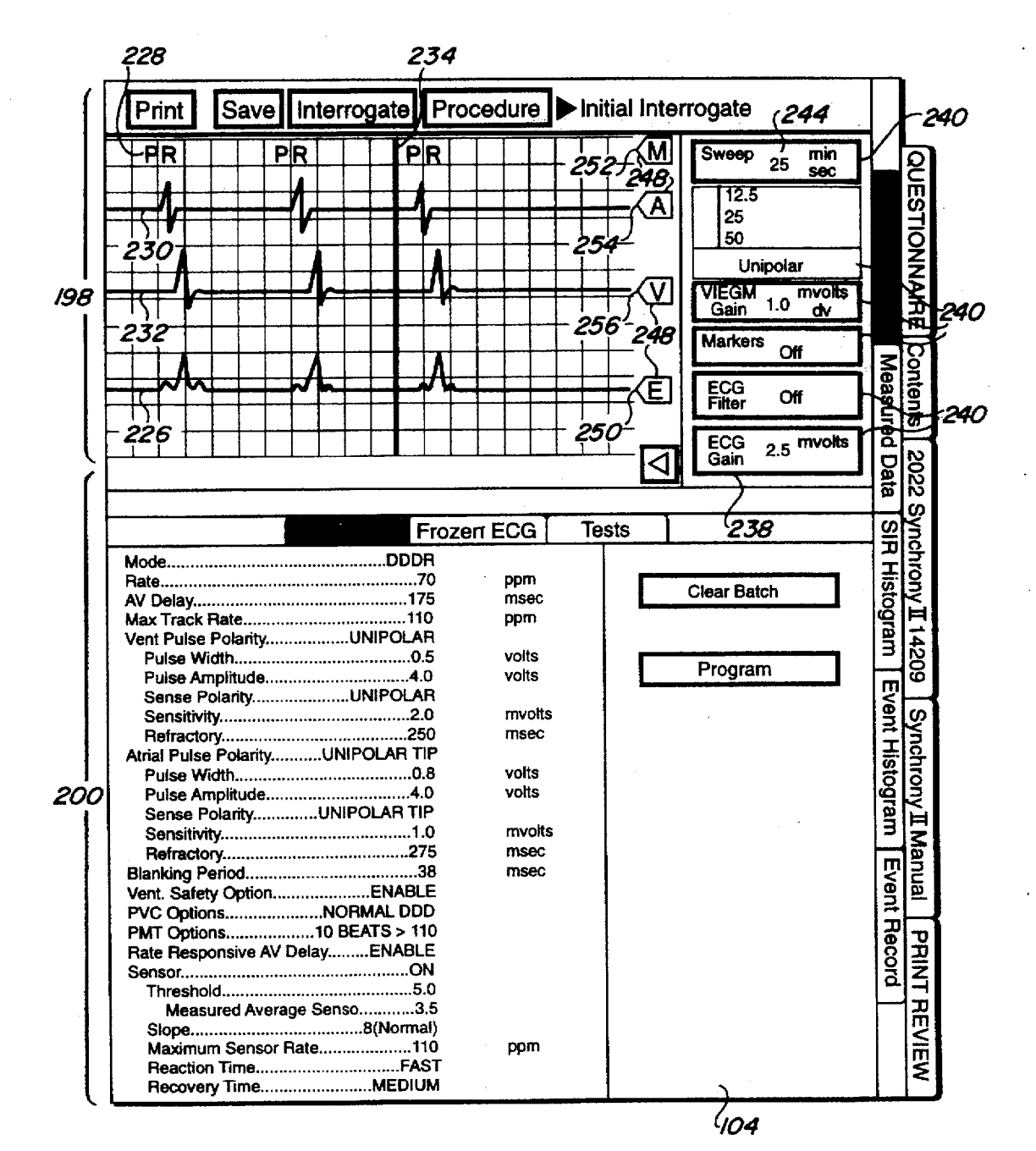

Turning now to FIG. 6 and comparing with FIG. 5, the lower window 200 is displayed with the pop-up window 218 closed. The upper window 198 in FIG. 6 has an ECG machine controls window 238 open. Tapping the pen 102 (FIG. 1) on one of a series of ECG machine controls buttons 240 will open an ECG machine controls pop-up window 242. In this case, one of the series of ECG machine control buttons 240, specifically a sweep speed button 244, was selected. The ECG machine controls pop-up window 242 is placed over a portion of the ECG machine controls window 238 but does not obscure the selected sweep speed button 244. Tapping one of a series of sweep speed choice buttons 246 in the ECG machine control pop-up window 242 alters the horizontal speed of the sweep bar 234 for the upper window 198. Changing sweep speed also changes the time scale in the upper window 198. For example, changing the sweep speed from 25 mm/sec to 50 mm/sec would double the horizontal spacing for the surface ECG channel 226, the AIEGM channel 230, and VIEGM channel 232. The marker data channel 228 would also be modified to remain synchronized with the waveforms but the appearance of the individual letters which serve as markers would not change. Tapping the pen 102 (FIG. 1) on the sweep speed button 244 will close the ECG machine controls pop-up window 242. Other attributes of the displayed channels can be modified such as the individual vertical scales (gains) of the waveforms. The process for altering these parameters follows the same steps as changing the sweep speed.

The vertical position of each channel can be varied by use of a channel position icon 248, specifically a surface ECG channel position icon 250, a marker data channel position icon 252, an AIEGM channel position icon 254, and a VIEGM channel position icon 256. The channel of medical data 226, 228, 230, or 232 is moved by tapping the pen 102 (FIG. 1) on the associated channel position icon 250, 252, 254, or 256 and then dragging the pen 102 (FIG. 1) vertically across the surface of the digitizer display screen 104. Removing the pen causes the channel of medical data 226, 228, 230, or 232 to relocate to the new vertical position. A comparison of FIG. 5 and FIG. 6 illustrates the capacity to display the channels of medical data in any arbitrary order and spacing. The channels of medical data in FIG. 5 are arranged: VIEGM channel 232, AIEGM channel 230, marker data channel 228, and surface ECG channel 226 from bottom to top of the upper window 198. In contrast FIG. 6 has the channels of medical data arranged: surface ECG channel 226, VIEGM channel 232, AIEGM channel 230, and then marker data channel 228 at the top of the upper window 198.

In addition to the display of current medical measurements, the tablet computer 100 (FIG. 1) can be used to examine stored medical measurements. Many of the files of stored measurements have data collected over a period of one or more minutes. At a typical sweep speed of 25 mm/sec, the tablet computer 100 (FIG. 1) only displays a few seconds of medical data at a time. Working with a file of stored data that is considerably longer than the viewing area on the display presents challenges similar to working with a long paper scroll of information.

Figure 7:
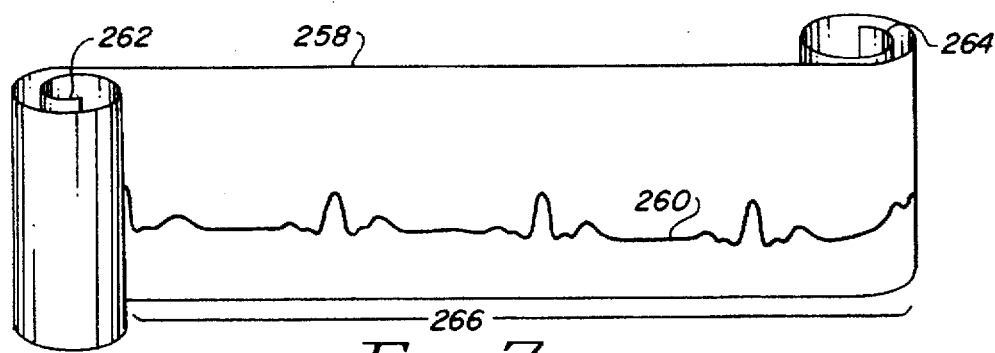
FIG. 7 is a conceptual illustration of a paper data scroll containing surface ECG measurements that vary with time.

FIG. 7 shows a paper data scroll 258 containing a written copy of a recorded surface ECG 260. The paper data scroll 258 has a first end 262 with the beginning of the data, a second end 264 with the termination of the data, and a segment 266 of the paper data scroll where the recorded surface ECG 260 is visible. The portion of the paper data scroll 258 that is in the segment 266 where the data is visible can be changed by rolling one end and unrolling the other end. Like the paper data scroll 258, an electrically stored file of data (described in connection with FIG. 8) has a beginning, an end, and a portion that is being displayed. Unlike the paper data scroll 258, the electronically stored file of data is a memory image that is processed for display and thus the appearance of the data can be altered by changing such parameters as the horizontal and vertical scales which are called sweep speed (horizontal) and gain (vertical). The paper data scroll 258 is presented to introduce concepts relevant to manipulating data files such as those manipulated with the tablet computer 100 (FIG. 1).

Figure 8:
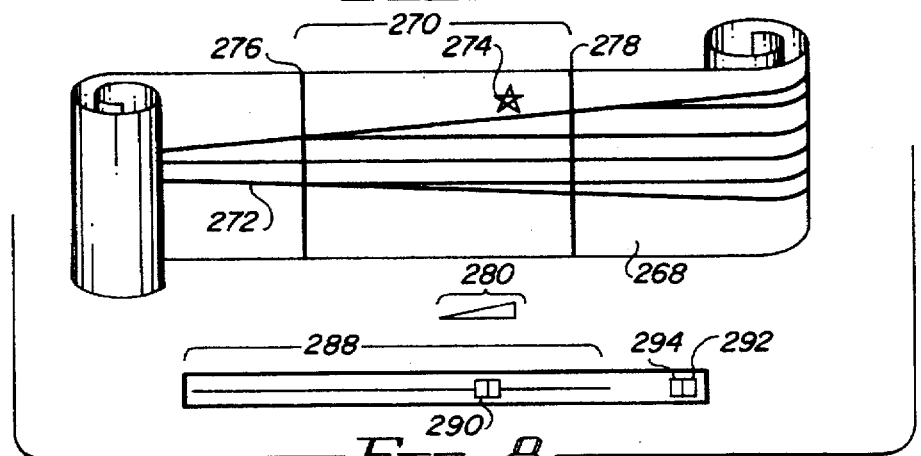
FIG. 8 is a conceptual illustration of a data scroll at a first position relative to a pair of borders that mark the segment of the data scroll being displayed in a screen display window at a given sweep speed along with a symbol for a single flick gesture and a scroll control icon at a first position on a scroll control bar.
Figure 9:
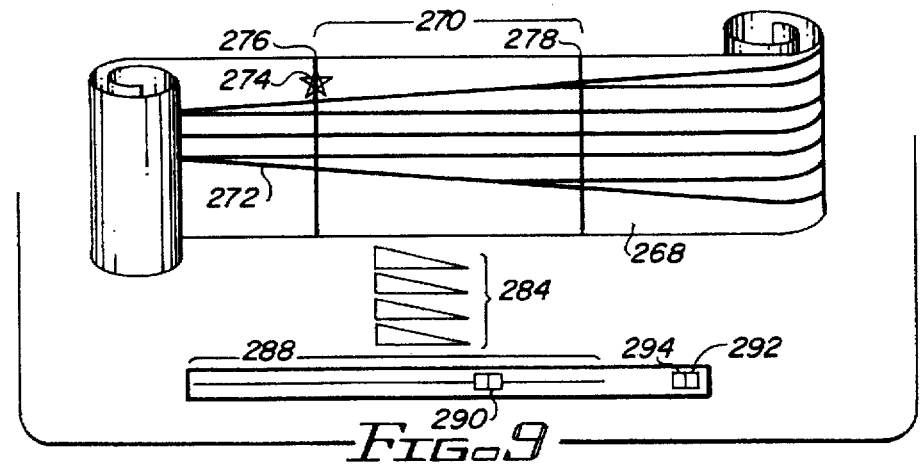
FIG. 9 is the data scroll from FIG. 8 moved to a second position, a symbol for a quadruple flick gesture, and a scroll control icon at the second position.
Figure 10:
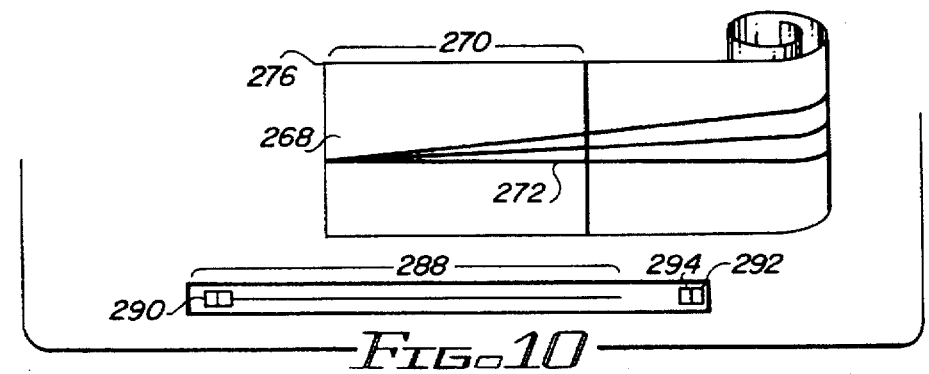
FIG. 10 is the data scroll of FIG. 9 moved to a third position and a scroll control icon at one extreme end of the scroll control bar.

Turning now to FIG. 8, the actual stored data is not on a paper data scroll 258 (FIG. 7) but is in an electronic data file called an electronic data scroll 268. The name reflecting the similarities to the paper data scroll 258 (FIG. 7). To better illustrate the movement of the electronic data, the electronic data scroll 268 is shown in FIGS. 8–10 using the image of a paper data scroll 258 (FIG. 7). The electronic data scroll 268 includes an array of values representing amplitude measurements of an analog waveform over time. Each successive measurement is taken at a small time increment after the preceding one. The gap in the time between data points is established by the sampling rate of the device (not shown) that provided the digital signal to the tablet computer 100 (FIG. 1). The tablet computer 100 (FIG. 1) smooths the discrete points of digital information into a curve that appears continuous to the physician or medical specialist. In the preferred embodiment, the information representing each of the four channels of medical information (surface ECG channel 226 (FIG. 5), AIEGM channel 230 (FIG. 5), VIEGM channel 232 (FIG. 5), and marker data channel 228 (FIG. 5)) is kept within one electronic data scroll 268. The tablet computer 100 (FIG. 1) synchronizes the display of different channels of data while adjusting for any differences in sampling rates among channels 226, 288, 230, and 232 (all in FIG. 5).

One of the challenges in developing a pen-based user interface for manipulating medical data is providing appropriate commands to allow the physician or medical specialist to move selected portions of the data scroll 268 into a visible segment 270 of the data scroll 268 that is visible on a window of a screen display. One set of such commands relies on the capacity of the tablet computer 100 (FIG. 1) to recognize gestures. Gestures provide an alternative to tapping buttons or tapping and dragging icons (described in connection with FIG. 4). The present invention uses gestures for a variety of functions. One such use is the "cross out" gesture which is used to simultaneously select and delete an item from a list. Typical uses of the cross out gesture could include eliminating a medical procedure from a suggested list of medical procedures provided to the physician or medical specialist, or deleting a pending request to print from the print queue.

The tablet computer 100 (FIG. 1) can be modified to accept other gestures to allow the physician or medical specialist to jump directly to certain specific screen displays without using the buttons and tabs to request the tablet computer 100 (FIG. 1) to display the specific screen display. Examples include making a gesture in the shape of an "H" to jump to patient History, making a gesture in the shape of a "B" to jump to implantable medical device Battery information, or making a gesture in the shape of a "C" to jump to a screen display showing Current program settings of the implantable medical device. The gesture does not have to be a character of the alphabet. Making a gesture in the shape of an "R" and a "T" overlaid one upon the other (R) could be a gesture to cause a jump to a screen display with current (real-time) medical data. Gestures could be symbols known in math, science, or proofreading; or the gesture could be a completely novel symbol.

If the tablet computer 100 (FIG. 1) is allowing text input from the pen 102 (FIG. 1) and some of the valid gestures could be confused with text input, then a separate gestures-only input pad (not shown) can be provided within the screen display to allow unambiguous input of gestures.

Although gestures are a powerful set of tools, the preferred embodiment does not require the physician or medical specialist to know any gestures in order to use the tablet computer 100 (FIG. 1). Gestures are provided as an alternative way for the physician or medical specialist familiar with the gestures to quickly manipulate the screen displays.

FIGS. 8–10 illustrate the use of gestures to manipulate the visible segment 270 of the electronic data scroll 268. (As previously explained, the electronic data scroll 268 is illustrated in these figures using images like the paper data scroll 258 (FIG. 7) rather than a memory array to better illustrate the manipulations.)

Starting in FIG. 8, the electronic data scroll 268 in a first position with data comprising a long thin triangle 272 with a point of the triangle at the beginning of the electronic data scroll 268 and a flat base of the long thin triangle 272 at the other end of the electronic data scroll 268 is shown along with an annotation 274. The long thin triangle 272 is not medical data, but serves as an example that highlights the movement of the electronic data scroll 268. The visible segment 270 of the electronic data scroll 268 appears in a window of a screen display at a given sweep speed (horizontal scale) and is bracketed by a left side border 276 and a right side border 278. Below the electronic data scroll 268 in the first position, a single flick gesture symbol 280 is shown with the broad end of the single flick gesture symbol 280 directly below the center of the annotation 272. In this example, the narrow end of the single flick gesture symbol 280 is to the left of the broad end. This single flick gesture symbol 280 is a symbol representing a gesture, not a gesture itself. The single flick gesture symbol 280 indicates, first, that the pen 102 (FIG. 1) was placed on the screen display window (typically the lower window 200 (FIG. 4)) where the electronic data scroll 268 was being displayed; second, that the horizontal position of the initial contact of pen 102 (FIG. 1) was in a vertical line with the center of the annotation 274; third, that the pen 102 (FIG. 1) was dragged to the left; and fourth, that the flick gesture was not immediately repeated.

The response to this single flick gesture is the electronic data scroll 268 in a second position as shown in FIG. 9. The portion of the long thin triangle 272 with the same horizontal position as the initial contact of the pen 102 (FIG. 1) at the beginning of the single flick gesture represented by the single flick gesture symbol 280 (FIG. 8) has been moved to the left side border 276. The right half of the annotation 274 would be visible in the window of the screen display. Displaying a portion of the annotation 274 when the annotation 274 straddles a right side border 278 or left side border 276 facilitates locating the portions of the electronic data scroll 268 that are annotated. If the system did not display annotations that were only partially within the visible segment 270 of the electronic data scroll 268, and the physician or medical specialist advanced through the electronic data scroll 268 by increments equal to one visible segment 270 of the electronic data scroll 268, the physician or medical specialist might not see some annotations at all. For example, if the annotation 274 straddled the right side border 278 and was suppressed because the annotation 274 straddles the right side border 278, the annotation 274 would be suppressed again when the electronic data scroll 268 was moved an amount equal to one full visible segment 270 and thus placing the annotation 274 straddled on the left side border 276.

The single flick gesture moves the electronic data scroll 268 to the right if the pen 102 (FIG. 1) is flicked to the right. Because the single flick gesture is responsive to the horizontal position of the pen tip 110 (FIG. 1) at the start of the gesture, the single flick gesture can move the electronic data scroll 268 with great precision in a single command.

A double flick is two successive flicks (not shown) and will move the electronic data scroll 268 one full visible segment 270 in the direction of the flicking motion. For example, a double flick to the right would cause the annotation 274 in the electronic data scroll 268 in the second position to straddle the right side border 278. The response to the double flick gesture is independent of the initial horizontal position of the pen tip 110 (FIG. 1) in the first flick. The double flick gesture provides the physician or medical specialist with the ability to move through the electronic data scroll 268 as if the data were affixed upon the pages of a book.

A quadruple flick gesture symbol 284 in FIG. 9 represents four successive flicks. The quadruple flick gesture moves the visible segment 270 to the extreme end of the electronic data scroll 268. Four quick repetitions of the flick motions to the right move the visible segment 270 of the electronic data scroll 268 to the extreme left end of the electronic data scroll 268, as shown by the electronic data scroll 268 in a third position in FIG. 10. Four quick flick motions to the left (symbol for gesture not shown) move the visible segment 270 of the electronic data scroll 268 to the extreme right end of the electronic data scroll 268 (data scroll after movement not shown).

In keeping with the design goal to use gestures as an alternative method and not the exclusive method to accomplish a given task, movement through the electronic data scroll 268 can be accomplished without the flick gestures. Another method employs a scroll control bar 288 and a scroll control icon 290 as shown in FIGS. 8–10. The scroll control bar 288 has a left end that indicates the beginning of the scroll and a right end indicating the termination of scroll. The position of the scroll control icon 290 shows the relative position of the visible segment 270 of the electronic data scroll 268 to the length of the electronic data scroll 268. The scroll control icon 290 can be dragged by the pen 102 (FIG. 1) to another position on the scroll control bar 288 in the same way that the channel position icons 248 (FIG. 6) could be dragged in the vertical direction. The window of the screen display will display the new visible segment 270 of the electronic data scroll 268 when the pen tip 110 (FIG. 1) lifts from the scroll control icon 290. For example, dragging the scroll control icon 290 to an extreme end of the scroll control bar 288 is equivalent to the quadruple flick gesture.

A "page forward" button 292 and a "page back" button 294 each move the electronic data scroll 268 one full visible segment 270 as can be done with the double flick gesture. The number of visible segments 270 of data in the electronic data scroll 268 depends on both the duration of the electronic data scroll 268 and the amount of time displayed in each visible segment 270. A screen display with a window (198 or 200 in FIG. 4) that is 150 millimeters wide and using a 25 millimeter per second sweep speed displays six seconds of data. Note that for frozen (stored) data, sweep speed merely controls the horizontal scale of the stored data. A preferred length of frozen data scroll is two minutes, resulting in twenty visible segments 270 of electronic data scroll 268 to display the entire electronic data scroll 268 at 25 mm/sec sweep speed. Note the relatively small change in horizontal position between the scroll control icon 290 in FIG. 8 and the scroll control icon 290 in FIG. 9 thus illustrating that the scroll control bar 288 and scroll control icon 290 are most useful for large movements of the electronic data scroll 268. The large number of visible segments 270 per electronic data scroll 268 make the precision of the single flick gesture or of the hand tool (discussed below in connection with FIG. 11) important additions to the method of using the scroll control icon 290 on the scroll control bar 288.

Figure 11:
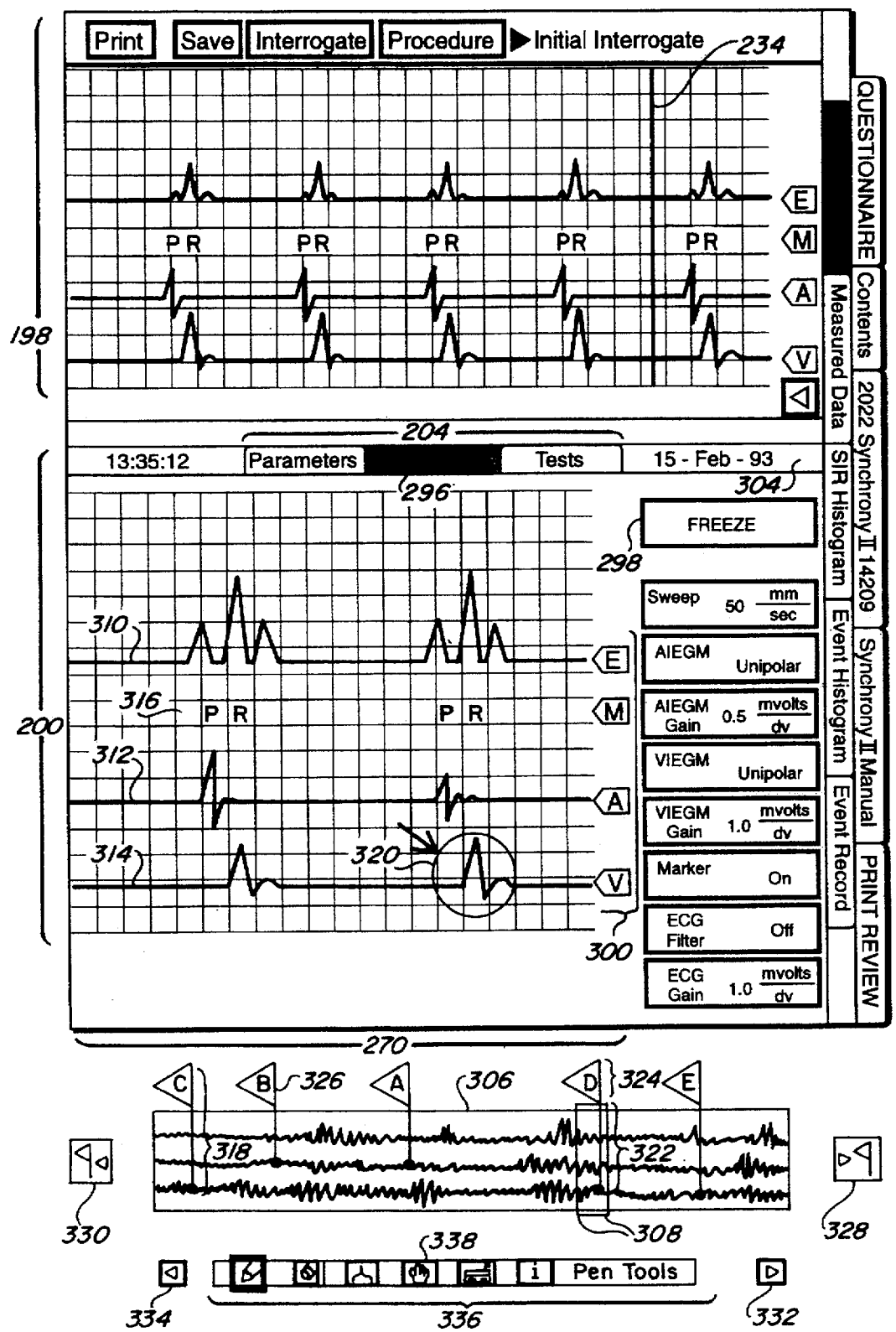
FIG. 11 is a screen display on the digitizer display screen with real-time data in the upper window, frozen data in the lower window, a compressed buffer overview, and a pen tool icon bar.

Turning now to FIG. 11, the upper window 198 is displaying current medical data and is being updated by the sweep bar 234. A portion of the processing and memory circuit 142 (FIG. 2) is called the current buffer. The current buffer stores a wrap-around buffer of the current data, with the data to the immediate left of the sweep bar 234 being the most current data in the current buffer. The preferred embodiment stores two minutes of current data in the current buffer. In FIG. 11, a frozen ECG horizontal tab 296 has been selected and remains in a highlighted condition. The lower window 200 no longer displays the parameters for the implantable medical device 116 (FIG. 2) but now has a set of data channels like the upper window 198. Tapping a freeze button 298 in the lower window 200 copies the current buffer into a temporary storage space in the processing and memory circuit 142 (FIG. 2). The temporary storage space called the frozen ECG scroll can be manipulated in the lower window 200 of this screen display. Note that the frozen ECG scroll contains all four channels of medical data, not just the ECG data. The frozen ECG scroll is replaced with a new copy of the current buffer each time the freeze button 298 is tapped. The frozen ECG scroll is one type of frozen data scroll handled by the tablet computer 100 (FIG. 1).

Frozen ECG machine controls buttons 300 are on the right side of the lower window 200. The operation of these buttons is the same as for the series of ECG machine controls buttons 240 (FIG. 6) in the upper window 198 (as shown in FIG. 6).

An indication of time 302 is provided to the left of the horizontal tabs 204. The indication of time 302 displays the time of measurement of the portion of the frozen data scroll displayed at the left edge of the lower window 200. An indication of date 304 is provided to the right of the horizontal tabs 204 if the frozen data scroll was recorded on a date other than the current date.

Below the lower window 200 is a compressed buffer overview 306 and a indication of position 308. The compressed buffer overview 306 provides miniature renditions of the waveforms in the frozen data scroll. Continuing with the analogy to the paper data scroll 258 (FIG. 7), the compressed buffer overview 306 is analogous to unrolling the entire paper data scroll 258 (FIG. 7) and shrinking the unrolled scroll to fit into the window allocated to the compressed buffer overview 306. The rendition reflects the relative positions and gains of a frozen surface ECG channel 310, a frozen AIEGM channel 312, and a frozen VIEGM channel 314 (all shown in lower window 200). A frozen marker data channel 316 (also shown in lower window 200) is not reproduced in the compressed buffer overview 306.

The compressed buffer overview 306 provides feedback concerning the position of the visible segment 270 relative to the entire frozen data scroll similar to the feedback provided by the scroll control bar 288 (FIG. 8) and scroll control icon 290 (FIG. 8) described previously,. This feedback is provided by the indication of position 308 on the compressed buffer overview 306. The preferred embodiment of the invention uses the compressed buffer overview 306 instead of scroll control bar 288 (FIG. 8) when displaying frozen data scrolls. The scroll control bar 288 (FIG. 8) is used for movement within reference handbooks (described in connection with FIG. 2) and other non-scroll information.

As a further aid in locating portions of the frozen data scroll, a flag 318 is added to the compressed buffer overview 306 whenever an annotation 320 is added to the frozen data scroll. The flag 318 is comprised of a flagstick 322 and a pennant 324. The base of the flagstick 322 points to the position in the compressed buffer overview 306 representative of the location of the annotation 320. The pennant 324 contains a unique symbol 326 to identify the annotation 320. In the preferred embodiment a letter of the alphabet is used, starting with "A" for the first annotation and "B " for the second. The unique symbol 326 preferably does not contain information indicative of the type of annotation. The unique symbols 326 preferably are not reordered or reissued if an annotation is deleted.

A triple flick gesture (not shown) will move the frozen data scroll to the next flag 318. For example, three flicks from left to right in the lower window 200 would move the frozen data scroll so that the annotation (not shown) associated with the next flag to the left would be displayed. For example, the gesture of a triple flick to the right would bring the annotation marked by flag "A" into view.

A flag jump right button 328 is provided to the right of the compressed buffer overview 306 and a flag jump left button 330 is provided to the left of the compressed buffer overview 306. Buttons 328 and 330 serve the same function as the triple flick gesture. The flag jump buttons 328 and 330 are optional features that can be added by the field service engineer. These buttons are not included in the preferred embodiment in an effort to minimize the number of buttons and controls on the screen display. A "page forward" button 332 and a "page back" button 334 are provided on either side of a pen tool icon bar 336 so that memorization of gestures in order to use the tablet computer 100 (FIG. 1) is not required. As described in discussion for FIGS. 8-10, the page forward button 332 advances the frozen data scroll one visible segment 270 at the current sweep speed setting. Conversely, the page back button 334 moves the frozen data scroll one visible segment 270 to the left. Thus the physician or medical specialist can move to the next flag 318 without using the triple flick gesture by using page forward and page back buttons 332 and 334.

An alternative method of using the compressed buffer overview 306 is to tap the pen 102 (FIG. 1) on the flag pennant 324 to move the frozen data scroll so that the selected flag's annotation and the associated segment of frozen data scroll is displayed in the lower window 200.

Another tool for making small horizontal adjustments to the frozen data scroll is provided on the pen tool icon bar 336. Tapping a hand tool icon 338 on the pen tool icon bar 336 turns the pen 102 (FIG. 1) into the hand tool. When the pen 102 (FIG. 1) is functioning as the hand tool, placing the pen 102 (FIG. 1) anywhere on the lower window 200 and then dragging the pen 102 (FIG. 1) horizontally causes the frozen data scroll to move in the horizontal direction with the pen 102 (FIG. 1) as if the pen 102 (FIG. 1) was holding onto the frozen data scroll. The pen 102 (FIG. 1) continues to function as the hand tool until the hand tool icon 338 is tapped again on the pen tool icon bar 336. The various flick gestures and other methods for movement in the frozen data scroll are recognized while using the hand tool feature.

Figure 12:
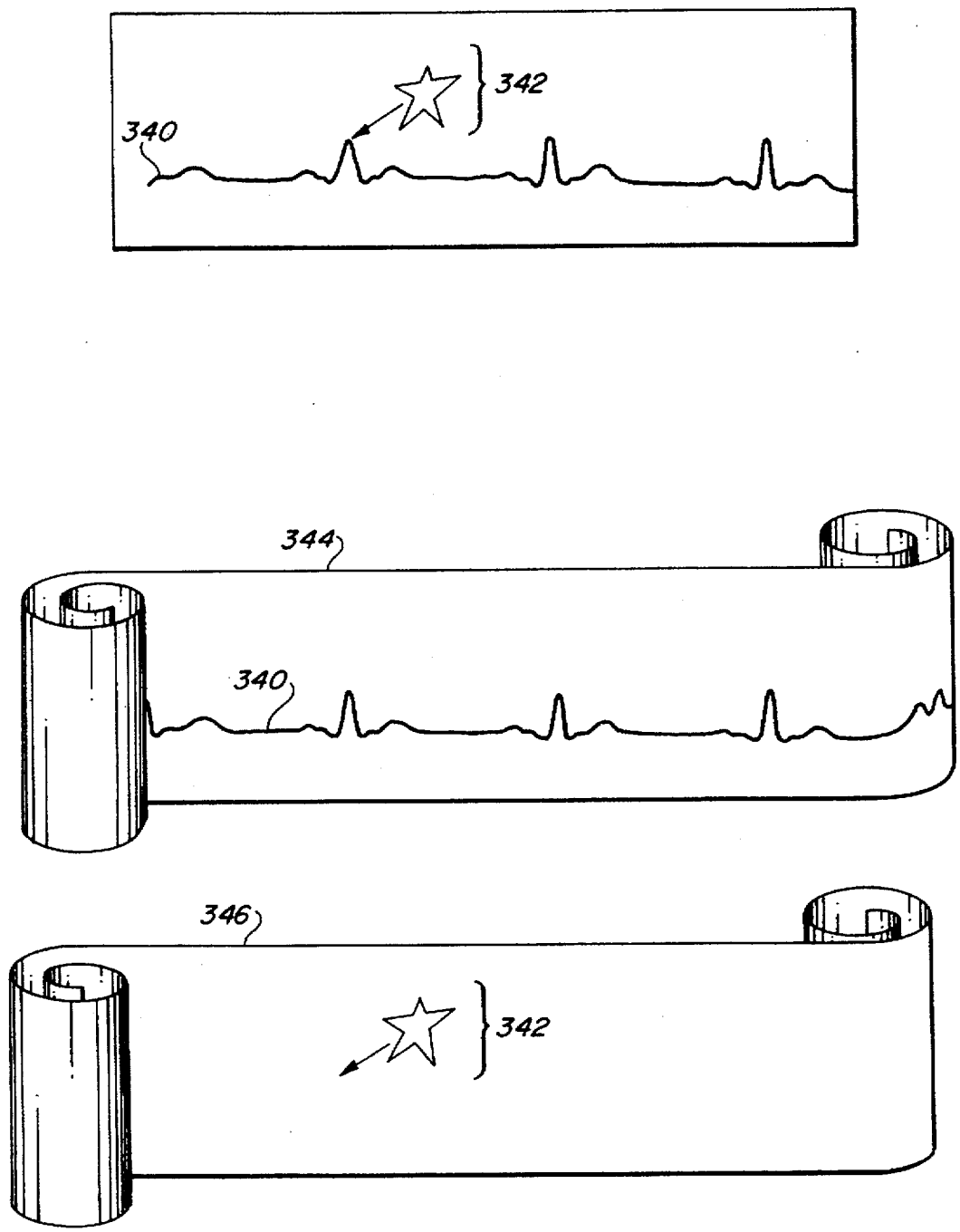
FIG. 12 is an annotated image of surface ECG data from a portion of a screen display on the digitizer display screen, and constituent parts of the annotated image.

Turning now to FIG. 12, the image from a screen display of a surface ECG channel 340 with a simple annotation 342 of an arrow and star appear to the physician or medical specialist as if the simple annotation 342 is stored with the surface ECG channel 340 in the data scroll of medical data. In the preferred embodiment, the medical information is stored in a data scroll 344, (shown for purpose of illustration with an image of a paper data scroll) and the annotations for that data scroll 344 of medical data are stored in an annotation scroll 346 (also shown for purpose of illustration with an image of a paper scroll) which is a separate data file that corresponds to the data scroll 344 of medical data. The two images are combined in the display logic and memory circuit 144 (FIG. 2) to form one image. Note that in the preferred embodiment a grid pattern (such as shown in lower window 200 of FIG. 11) is combined with the other images to aid measurements of time and amplitude.

Referring now to FIG. 13, annotation of the medical data is initiated by tapping the pen 102 (FIG. 1) onto an ink tool icon 348 on the pen tool icon bar 336. After tapping, a dark square 350 highlights the ink tool icon 348 indicating that the pen 102 (FIG. 1) will now function as an ink tool. An ink tool can "write" on portions of the screen display.

The tablet computer 100 (FIG. 1) uses a "connection point" to associate an annotation with a particular segment of a channel of medical information. The connection point allows the annotation to follow the appropriate segment of medical data when the channel of medical data is moved.

When the pen 102 (FIG. 1) taps the ink tool icon 348 to activate the pen 102 (FIG. 1) as the ink tool, the tablet computer 100 (FIG. 1) reminds the physician or medical specialist with a pop-up message 352 to designate a connection point. The tablet computer 100 (FIG. 1) expects that the next input from the pen 102 will designate the connection point, so all input prior to contact with any displayed medical data and the entire stroke that touches the medical data is considered part of the input to designate the connection point. The tablet computer 100 (FIG. 1) will then delete the marks made while designating the connection point from both the screen display and the acetate layer memory 140 (FIG. 2) so that the designating stroke does not become part of the annotation.

In FIG. 13, the physician or medical specialist did not designate a connection point but attempted to annotate by drawing a counterclockwise circle around an AIEGM waveform. The tablet computer 100 (FIG. 1) interprets this circle not as an annotation but as a designation stroke. Unfortunately, the first piece of medical data that was touched by the pen 102 (FIG. 1) was not a segment of the frozen AIEGM channel 312 but one of the markers from the frozen marker data channel 316.

Figure 14:
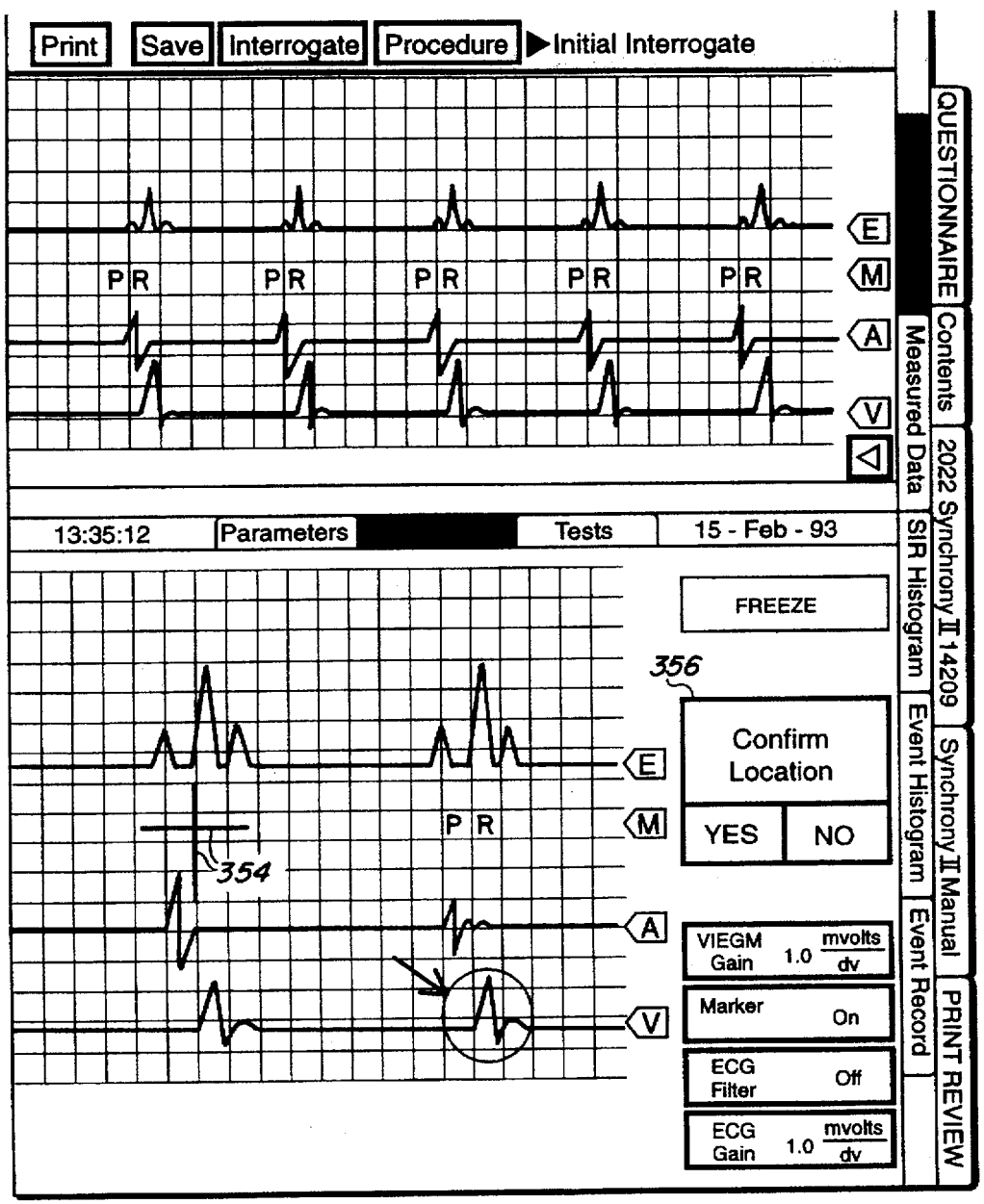
FIG. 14 is a screen display on a digitizer display screen during the confirm cycle after the inadvertent attachment of the connection point to marker data channel information.
Figure 15:
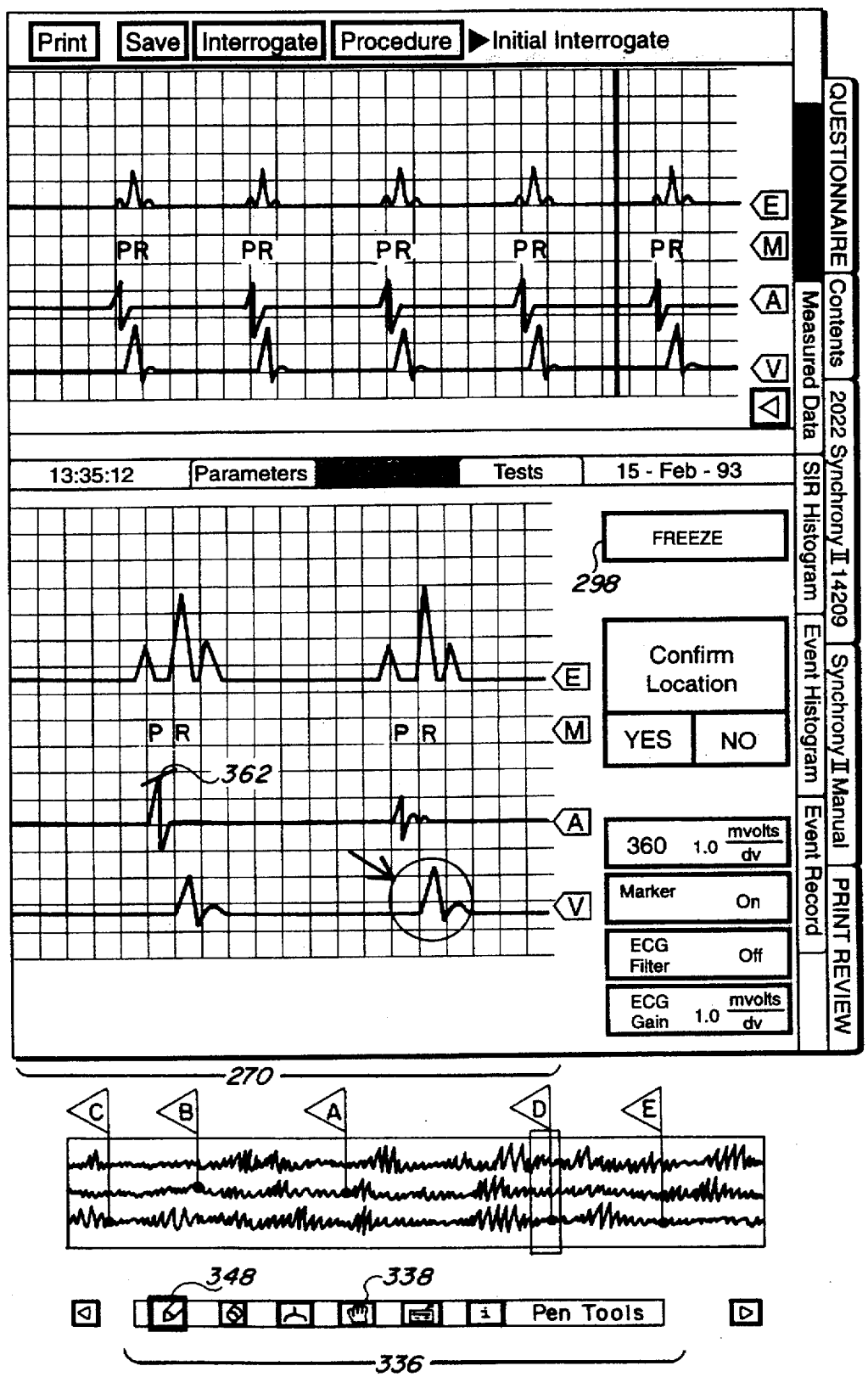
FIG. 15 is a screen display on the digitizer display screen showing attachment of the connection point to the intended section of medical data.

Turning now to FIG. 14, the improperly placed connection point is highlighted by a set of cross hairs 354 centered on the point of first contact between the pen 102 (FIG. 1) and medical data while the tablet computer 100 (FIG. 1) was awaiting designation of a connection point. The physician or medical specialist is now offered a confirmation window 356 to confirm the designation of the connection point. Tapping a confirmation-no button 358 with the pen 102 (FIG. 1) requests another opportunity to designate a connection point. Turning now to FIG. 15, the selection of a connection point on the AIEGM waveform 312 is completed by tapping a confirmation-yes button 360 in the "confirm connection point" step. Note that a line 362 drawn to touch the medical data does not become an annotation, but merely establishes the connection point and is then deleted from the acetate layer memory 140 (FIG. 2). After the connection point is designated and confirmed, the tablet computer 100 (FIG. 1) interprets input from the pen 102 (FIG. 1) as annotation input.

The confirmation cycle can be eliminated to streamline the designation of the connection point. The tablet computer 100 (FIG. 1) may be modified by a field service engineer to no longer provide a confirmation cycle. Removal of the confirmation cycle is appropriate for experienced users who rarely forget to designate the connection point before entering the annotation. However, even experienced users may find the confirmation cycle useful if the screen display is sufficiently crowded with medical data to make accidental contact with other data while designating the connection point a substantial risk.

If the confirmation cycle has been removed, the physician or medical specialist designates the connection point by dragging the pen 102 (FIG. 1) across the medical data that is to serve as the connection point. The tablet computer 100 (FIG. 1) recognizes this pen stroke as designating the connection point and then deletes the designating stroke from the screen display and the acetate layer memory 140 (FIG. 2) so the designating stroke does not become part of the annotation.

Staying with FIG. 15, after designating a connection point, the physician or medical specialist uses the pen 102 (FIG. 1) as the ink tool to annotate the window of the screen display containing the connection point. The physician or medical specialist may also use other pen tool features such as the hand tool, to move the frozen data scroll slightly, or the eraser tool (discussed below). For example, tapping the hand tool icon 338, suspends the action of the ink tool icon 348. The physician or medical specialist can reposition the frozen data scroll and then tap the hand tool icon 338 a second time to turn off the hand tool and turn the pen 102 (FIG. 1) back into the pen tool.

The entry of the annotation is terminated by tapping the ink tool icon 348 on the pen tool icon bar 336 to terminate the ink tool function, or by moving the connection point out of the visible segment 270 of the data scroll, i.e., off of the window in the screen display. The connection point is moved off the window by moving the frozen data scroll a sufficient amount horizontally or by causing the tablet computer 100 (FIG. 1) to jump to another screen display.

In the preferred embodiment, the annotation is terminated and a new connection point for a new annotation is established if the physician or medical specialist touches a segment of medical data from another channel. This feature can be suppressed by the field service engineer if for a particular application the density of medical data in the window causes frequent accidental termination of annotations.

The connection point is deleted and the annotation deleted if the freeze button 298 is used to load a new copy of the current buffer into the frozen ECG scroll. The print and save features, discussed below, provide methods for the physician or medical specialist to preserve annotations before loading a new set of data from the current buffer into the frozen ECG scroll. Alternative embodiments of the invention allow the frozen ECG scroll to add the new material from the current buffer to the front of the frozen ECG scroll. While this alternative method preserves data, it complicates the use of the compressed buffer overview and other tools for manipulation of the data scroll. Another alternative embodiment of the invention automatically saves the data each time the freeze button 298 is used. After the test or session with the patient is completed the physician or medical specialist would then typically delete many of the saved files and keep the files that best describe the test or session. Although this method of first saving, then deleting requires considerably more memory, it more closely approximates the practice of physicians and medical specialists who print many images of the waveforms and then select a small fraction of the printed images for retention with the patient records. The concern about memory limitations within the tablet computer 100 will recede as wireless links mature and thus allow greater use of memory storage outside of the tablet computer 100.

Figure 16:
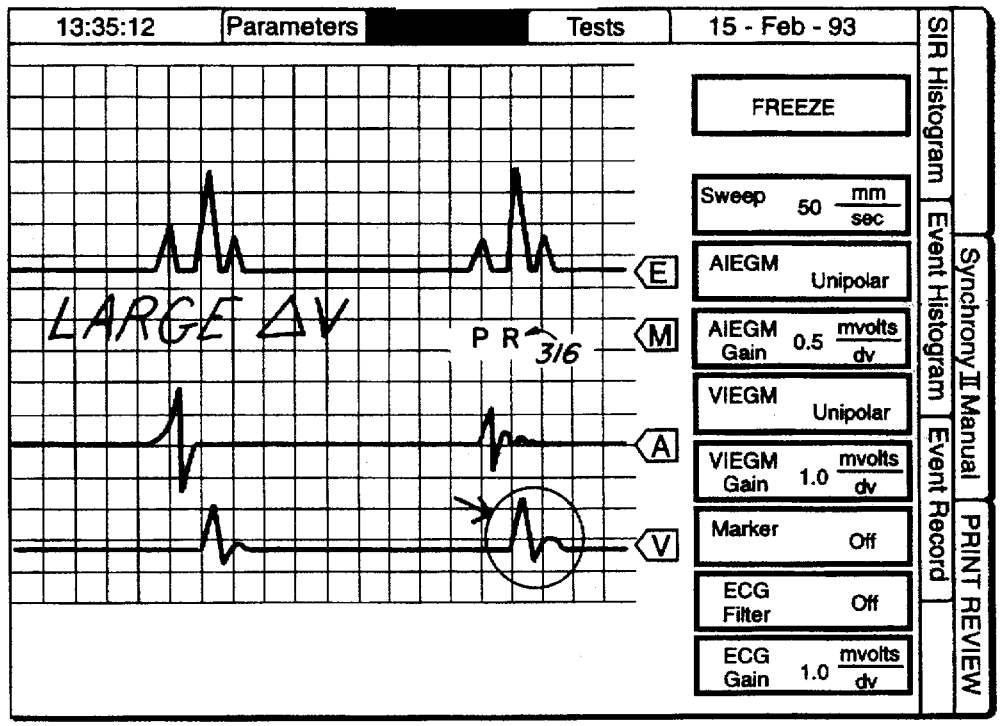
FIG. 16 is a portion of a screen display on a digitizer display screen showing an annotation added to a segment of a frozen data scroll.

Continuing with the annotation example, and turning to FIG. 16, the physician or medical specialist has added an annotation "LARGE ΔV" that partially obscures the frozen marker data channel 316 information.

Figure 17:
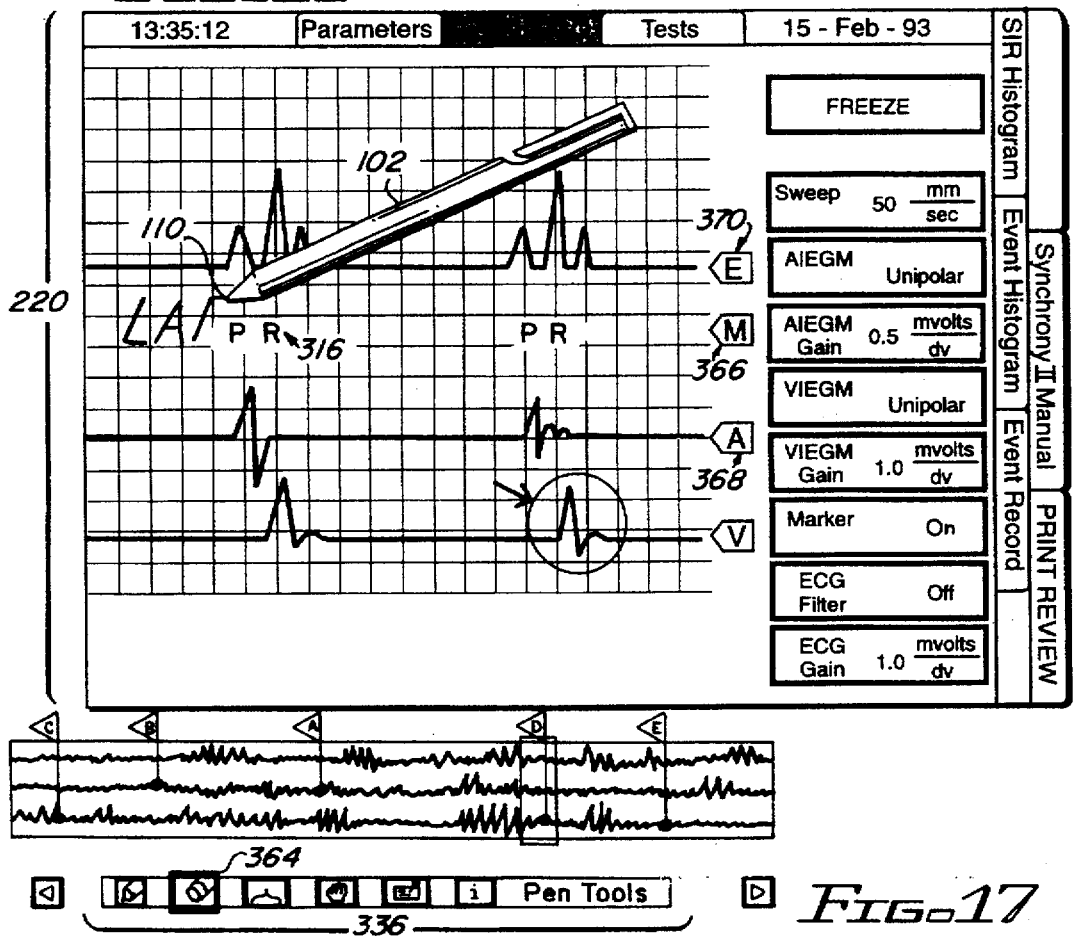
FIG. 17 is a portion of the screen display of FIG. 16 after the annotation has been partially erased by the pen acting as an eraser tool.

Turning now to FIG. 17, tapping on an eraser tool icon 364 on the pen tool icon bar 336 makes the pen tip 110 of the pen 102 an eraser of annotations. Note that the erasure of annotation material does not erase the medical data. Thus, the frozen marker data channel 316 information is undisturbed. Tapping the pen 102 a second time on the eraser tool icon 364 ends the function of the pen 102 as an eraser and resumes the function of the pen 102 as an ink tool.

Note that the physician or medical specialist could have solved the problem of the obscured frozen marker data channel 316 information by dragging a frozen marker data channel position icon 366 to the top of the lower window 200 to reposition the frozen marker data channel 316 or alternatively by dragging a frozen AIEGM channel position icon 368 above the frozen marker data channel position icon 366 and dragging a frozen surface ECG channel position icon 370 below the frozen marker data channel position icon 366, to rearrange the displayed channels of medical data to provide additional room for the annotation.

Figure 18:
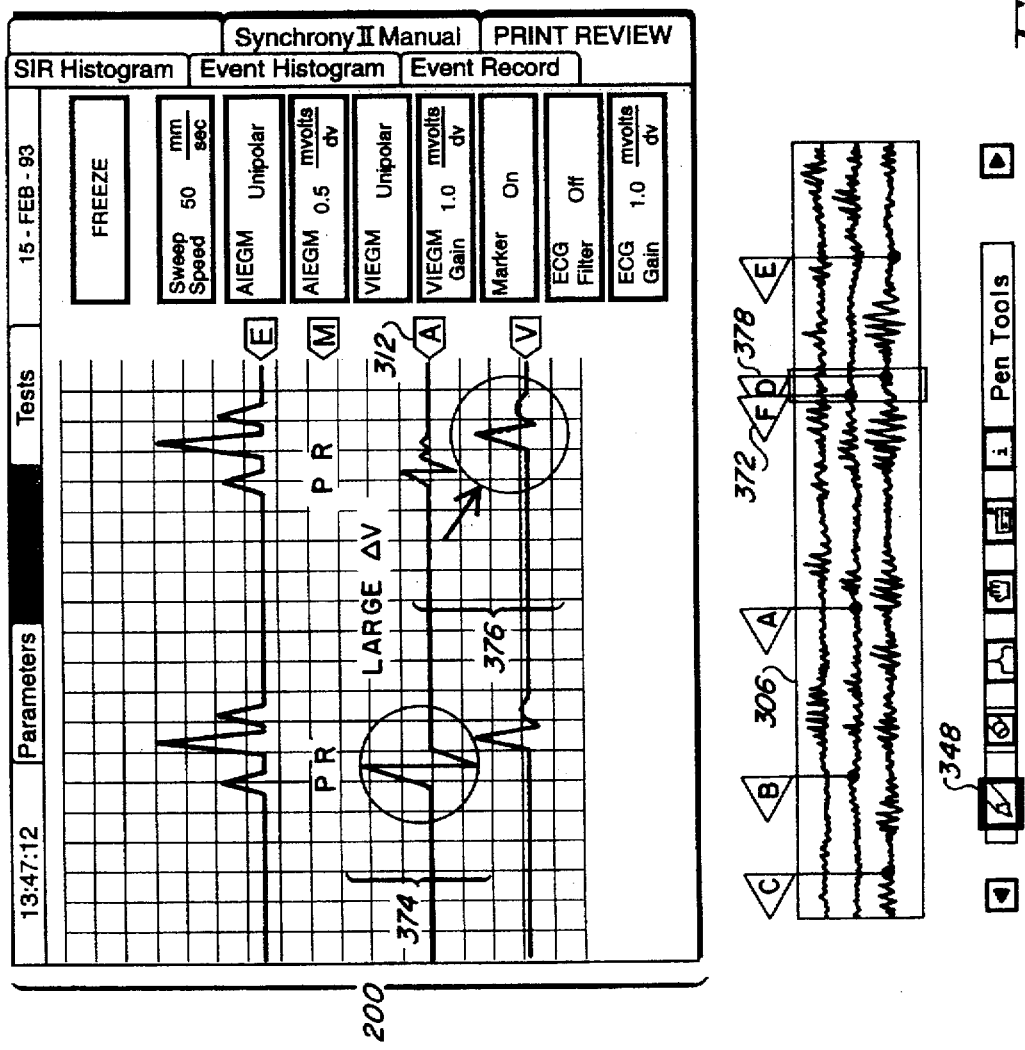
FIG. 18 is a portion of a screen display on the digitizer display screen including an annotated segment of frozen AIEGM data, a compressed buffer overview with flags marking the annotated portions of the frozen data scroll, and a pen tool icon bar.

Turning now to FIG. 18, the annotation step is terminated when the physician or medical specialist is satisfied with the annotation. The annotation step is terminated by tapping the highlighted ink tool icon 348, or by causing the connection point to move off the lower window 200.

Terminating the annotation step causes a new flag 372 to be placed on the compressed buffer overview 306. The base of the flagstick of the new flag 372 is on the portion of the compressed buffer overview 306 corresponding to the connection point. The pennant of the new flag 372 contains the letter "F" since the letters "A" through "E" have been used to uniquely identify other annotations. Note that the proximity of a new annotation 374 marked by the new flag 372 labelled "F" to an old annotation 376 marked by an old flag 378 labelled "D" causes the pennant for the new flag 372 labelled "F" to partially obstruct the pennant for the old flag 378 labelled "D".

Figure 19:
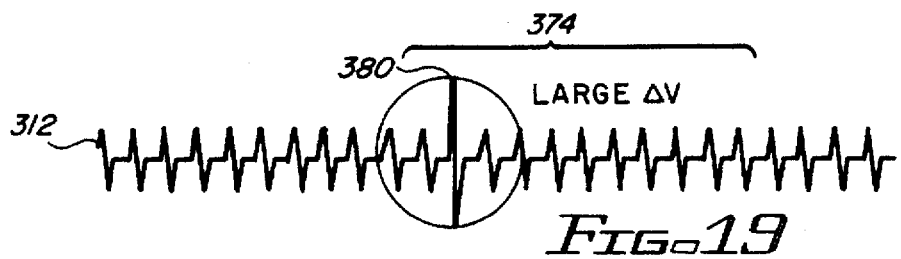
FIG. 19 is a portion of a screen display on the digitizer display screen showing the annotated AIEGM data of FIG. 18, but at a sweep speed that is slower than that used in FIG. 18.
Figure 20:
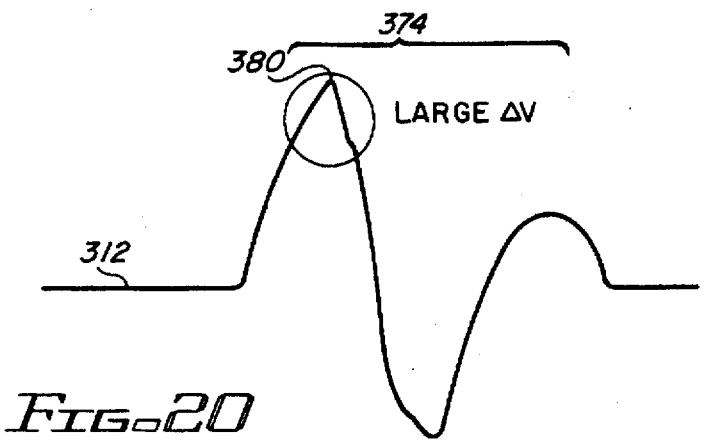
FIG. 20 is a portion of a screen display on the digitizer display screen showing the same annotated section of a AIEGM data as shown in FIGS. 18 and 19, but at an increased vertical gain and a faster sweep speed.

FIG. 19 and 20 show the appearance of the new annotation 374 from FIG. 18 when the frozen AIEGM channel 312 (FIG. 18) is displayed using various horizontal and vertical gains (horizontal gain is also known as sweep speed). In the preferred embodiment, the annotation size and displacement of the annotation from a connection point 380 does not vary with the horizontal and vertical gains used to display the channel of medical data.

The ink annotation is useful to highlight and to add brief comments. More extensive comments are difficult to fit between the multiple channels of medical data. Another type of annotation allows more extensive comments to be keyed to a portion of the medical data. This other type of annotation is called a footnote.

Turning now to FIG. 21, the frozen AIEGM channel 312 has been annotated with a circle annotation 382 around one AIEGM waveform through use of the ink tool in the manner previously described. The flag 318 with a unique identifier "C" was added to the compressed buffer overview 306 to mark the location of the circle annotation 382. After tapping the pen 102 (FIG. 1) on a note pad tool icon 384 on the pen tool icon bar 336, the physician or medical specialist taps on the lower window 200 to designate the footnote marker location. A footnote marker 386 appears in the designated location labeled with the same letter as will be used as the unique symbol for a flag labeled "D" (described in connection with FIG. 23). The footnote marker 386 is shaped like a book page with the upper right corner folded down as if marking an important passage. The footnote marker location is stored as an amplitude and a time value as is done with the medical data represented by the frozen surface ECG channel, frozen AIEGM channel, and frozen VIEGM channel 310, 312, and 314 (all in FIG. 11). The footnote marker 386 will be stored as part of another channel of medical data. Thus, the footnote markers position will not be altered by changes in vertical gain for the frozen surface ECG channel 310, frozen AIEGM channel 312, or frozen VIEGM channel 314 (all in FIG. 11). The footnote marker position will not be altered by changes in the positions of any of a series of frozen channel position icons 388.

Figure 23:
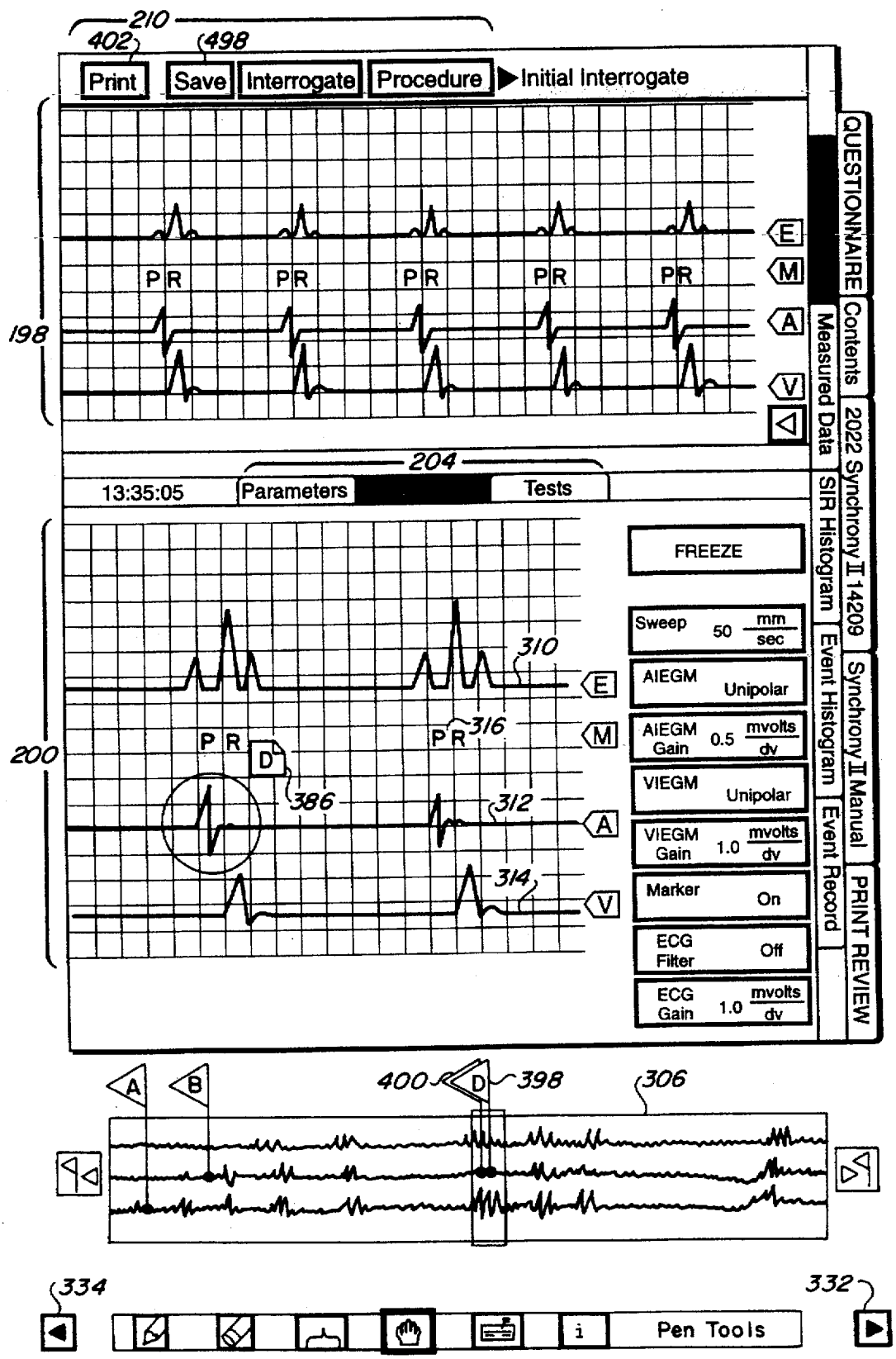
FIG. 23 is a screen display on the digitizer display screen containing an annotated segment of a frozen data scroll and a compressed buffer overview with flags marking the locations of annotations.

If the footnote pertains to one particular channel of medical data and the physician or medical specialist wishes to identify the channel being annotated, an ink annotation such as an arrow or circle annotation 382 can be added to highlight the subject of the footnote. FIG. 23 serves as an example of this combination of ink and footnote annotations for a particular piece of medical information.

Figure 22:
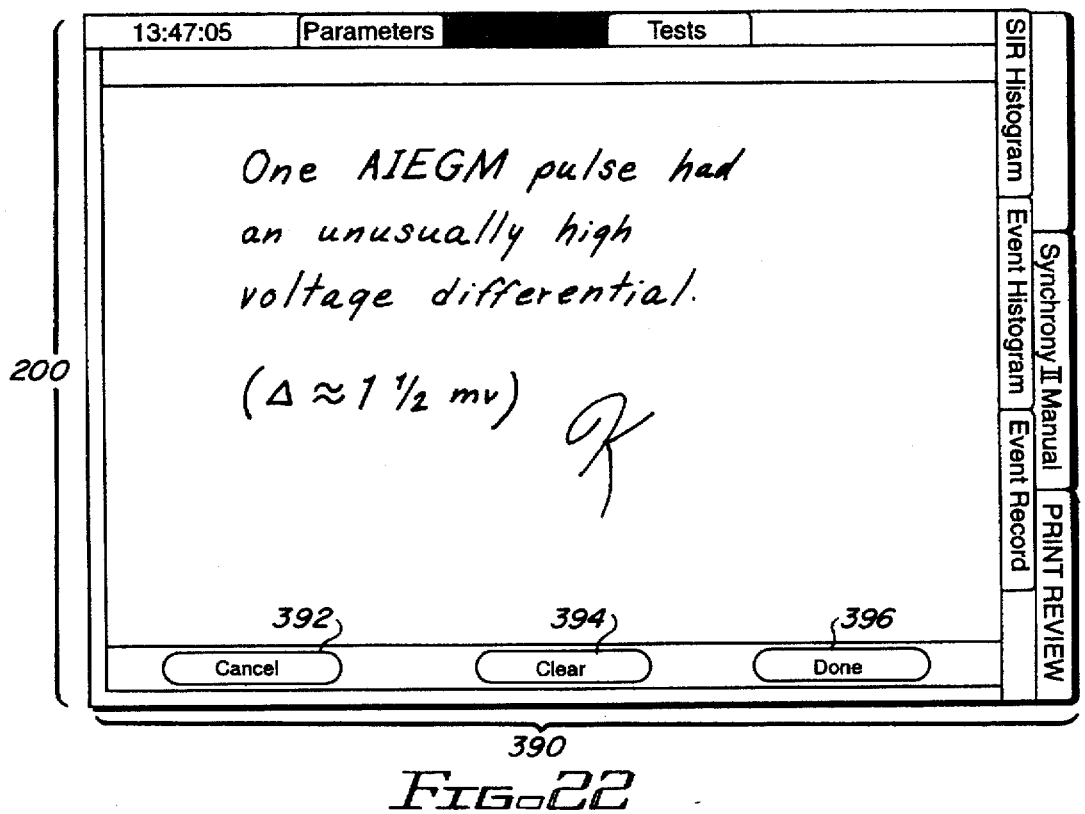
FIG. 22 is a portion of screen display on the digitizer display screen, containing a note pad screen.

After a short delay to display the footnote marker location, the screen display window being annotated is replaced with a note pad 390 shown in FIG. 22. In the preferred mode, the display and annotation of stored or frozen medical data occurs in the lower window 200. Thus FIGS. 21 and 22 are mutually exclusive lower windows 200 with the upper window 198 (FIG. 4) allocated to displaying the current performance of the heart.

In the preferred embodiment, the input to the note pad is not processed except to store the footnote annotation as described below. Special software programs called text recognition engines are known and have been applied to tablet computers. Such engines allow pen input to be recognized as characters and then manipulated as character data. Word processing tools with support of a wide range of pen-based edit command gestures are also known. The use of explicit buttons arranged on the digitizer display screen 104 (FIG. 1) as in the configuration of a standard typewriter keyboard (QWERTY keyboard) is another known input scheme for text. However, the preferred embodiment uses free-form text entry, storing the text as graphic data, to both reduce the number of commands needed to operate the system, and to provide a user interface that readily captures drawings, symbols, and other free-form input such as the initial of the person creating the annotation.

Still referring to the open note pad 390 in FIG. 22, tapping a cancel button 392 will end the note pad input step without saving the footnote annotation. Tapping a clear button 394 removes all electronic ink from the note pad 390 but leaves the note pad 390 open thus providing a new opportunity to compose the note without having to use the eraser tool or having to cancel and restart the note. Tapping a done button 396 will end the note pad input step, save the note pad input, and add another flag (described below in connection with FIG. 23) to the compressed buffer overview 306 (FIG. 21).

The result of tapping the done button 396 appears in FIG. 23 with a flag 398 labeled "D" marking the new footnote substantially covering a flag 400 labeled "C" (mostly covered and not visible) marking the ink tool annotation.

A footnote annotation can be erased by touching the footnote marker 386 with the pen tip 110 (FIG. 1) while the pen 102 (FIG. 1) is an eraser tool. A confirm cycle will prevent accidental erasure of a footnote inadvertently touched while erasing other annotations from the screen. (An example of the use Of a confirm cycle was discussed in connection with FIGS. 14–15).

Deleting the footnote removes the footnote marker 386 from the lower window 200, and removes the flag 398 labelled "D" for that footnote from the compressed buffer overview 306. Print or save requests made after the deletion of the footnote will not include the footnote. However, as discussed below in the sections on the print and save features, deleting a footnote does not delete the footnote from save files created before the deletion or from print requests made before the footnote was deleted.

A footnote may be moved with a press and hold gesture. Pressing the pen 102 (FIG. 1) upon the footnote marker 386 in the lower window 200 for a minimum of one-half second is recognized by the tablet computer 100 (FIG. 1) as the start of a press and hold gesture. Upon recognition, the tablet computer 100 (FIG. 1) places a marquee such as a blinking double line box (not shown) around the selected footnote marker 386.

After the marquee appears, the marquee and the footnote marker 386 it surrounds will "float." Floating means that the selected item will follow the pen 102 (FIG. 1) until the physician or medical specialist presses and holds the pen 102 (FIG. 1) for at least one-half second to affix the selected item to a new location. The marquee disappears when the item has been affixed. To move the selected item to a new location, the physician or medical specialist touches the selected item with the pen 102 (FIG. 1) and drags to pen 102 (FIG. 1) to the new location. The selected item continues to float until affixed, so the movement of the selected item does not need to happen within a single drag movement of the pen 102 (FIG. 1). Consequently, while an item is being floated, the physician or medical specialist may move the scroll using other gestures such as the various flick gestures or other aids such as the page forward button 332 or the page back button 334.

Printed or written patient records remain an important part of medical records. Therefore, the user interface for the tablet computer supports a variety of print options.

Still referring to FIG. 23, a request for a printed copy of the screen display being displayed is made by tapping a print button 402 found in the series of buttons 210 at the top of the screen display. For many screen displays with only one type of printed report, selection of the printed report is complete after tapping the print button 402. For screen displays with several possible types of printed report, tapping the print button 402 causes a pop-up menu (not shown) to appear on the screen display. This pop-up menu lists the possible types of print report. The screen display in FIG. 23 can be printed as one of two types of printed reports. The two types are named a summary report and a full report. Both a summary report request and a full report request prints all ink annotations and all footnote annotations visible at the time of the request for a report. These annotations are included in the printed image even if the ink annotation or footnote annotation is subsequently altered or deleted.

Turning now to FIG. 24, a summary report 404 of the screen display shown in FIG. 23 includes a print header 406 that identifies the printout for filing in the patient's records. The information in the print header 406 includes a model number of the implantable medical device 116 (FIG. 2), a unique serial number for the implantable medical device 116 (FIG. 2), a patient name, a print request date, a print request time, and a physician or medical specialist name. The information contained in the print header 406 can be customized by a field service engineer so that the print header 406 includes information germane to the filing system of a particular hospital or office of the physician or medical specialist rather than forcing the filing systems to conform to the format of FIG. 24. For example, the hospital department number or the hospital's patient identification number could be included in the header information.

Directly below the print header 406 is a parameter header 408. The parameter header 408 provides the future reader of the printed report the information necessary to analyze the summary report 404. Unlike the print header 406, which is independent of the particular screen display that is the basis of the print summary report 404, the contents of the parameter header 408 are dependent on the particular screen display to be printed. A screen display such as that shown in FIG. 23 which combines the frozen marker data channel 316 with the frozen surface ECG channel 310 and the frozen IEGM channels 312 and 314 is very useful for monitoring the performance of an implantable medical device 116 (FIG. 1) such as a pacemaker. But the analysis of the frozen marker data channel 316 against the heart measurement channels 310, 312, and 314 requires knowledge of such parameters as the pacing mode and the key timing parameters. This context information is the type of screen display specific information that would be provided in certain report parameter headings. Turning again to FIG. 24, this parameter header 408 contains the procedure step of the examination (which in this case is "Initial Interrogate"), the pacing mode (which in this case is DDDR), the important timing parameters, and the status of a magnet that is used to communicate to the implantable medical device. Also included in the parameter header 408 are the various gains for the graphed information, the sweep speed, and information about the collection and processing of the surface ECG and the IEGM information. A screen display displaying test data concerning the sensors in an implantable medical device 116 would display a different subset of parameters that explain the context of the test data.

As shown by a comparison of FIG. 24 to FIG. 23, the summary report 404 does not necessarily include all information that is in the screen display. The summary report 404 does not print the current medical data that is displayed in the upper window 198 of most screen displays. The current data is used by the physician or medical specialist to monitor the patient during the examination or other medical procedure. If a notable event occurs, the physician or medical specialist can move the information from the current buffer into the frozen ECG scroll. The frozen ECG scroll can then be examined, annotated, and printed.

In the preferred embodiment, the destination for summary reports 404 would be preset as the laser printer 172 (FIG. 3). Therefore a printer selection step is not required for summary reports 404 in the preferred embodiment.

The summary report is distinguishable from a screen dump (not shown) which merely prints the current display image without the additions and omissions of a summary report. Lacking both a print header and a parameter header, such a screen dump printout could be either misfiled or misinterpreted at some later date. The command to screen dump is imbedded in the tablet computer 100 (FIG. 1) and is enabled for users who need to create training manuals or otherwise need to document the appearance of the display screen rather than document patient medical data.

Short summary reports that focus on particular portions of a data scroll, or quickly summarize the underlying medical data are the most common type of print request. The user interface also supports longer printouts. These longer reports are called full reports. The most typical full report is the printing of the entire frozen ECG scroll or other stored scroll of data. This full report request automatically prints all channels of frozen medical data that appear on the display screen. All ink annotations and all footnotes are reproduced as they existed at the time of the request for a full report. A grid pattern is printed to facilitate measurements of voltage amplitudes and time intervals.

Turning now to FIG. 25, a first page 410 of the full report contains a print header 412. The print header 412 contains the same information as the print header 406 (FIG. 25) in the summary report 404 (FIG. 25). A parameter header 414 contains the procedure, the number of pages in this report, the start time and duration of the scroll. The parameter header 414 does not contain information about the device program settings of the implantable medical device 116 (FIG. 2) because a complete set of program settings 416 is printed directly below the parameter header 414. Additionally, a set of surface ECG parameters 418 is printed with the complete set of program settings 416.

Figure 26:
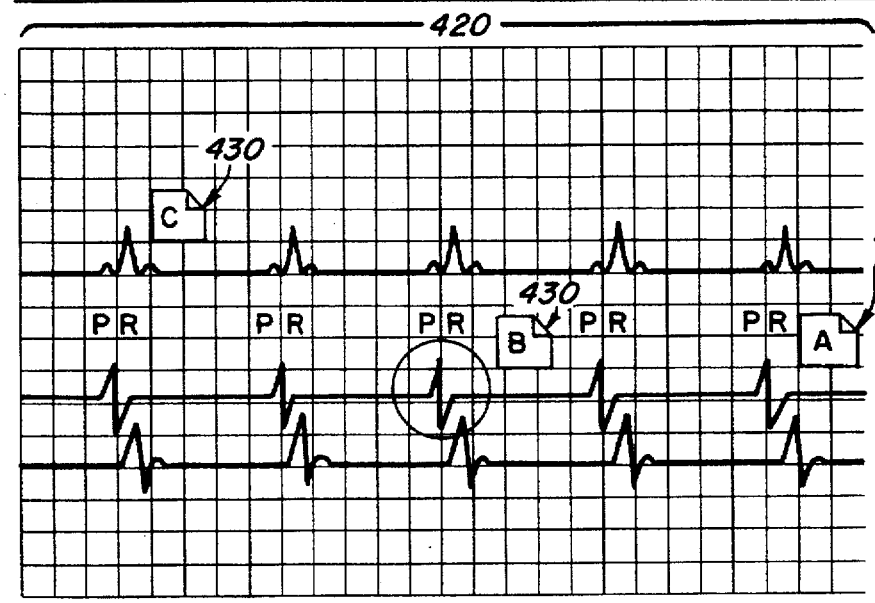
FIG. 26 is a subsequent page of a full report containing the print header, the parameter header, a segment of data scroll, and two footnotes related to that segment of a data scroll.

Turning now to FIG. 26, most subsequent pages of the full report have a printed segment 420 of the data scroll. Each subsequent page has the print header 412 containing the same information as found on the front page of the full report. The parameter header 414 appears below the print header 412. This parameter header 414 contains the procedure, page number, start time of the data scroll, and start time of the page. The frozen data scroll start date and start time may differ considerably from the report request date and report request time. The request date and request time are necessary to file the papers in the folder in the order that records the analytical steps of the physician or medical specialist. The start date and start time of the data scroll are necessary to match recorded data from other sources such as a strip chart.

The vertical scales are provided by the surface ECG gain, AIEGM gain, and VIEGM gain. The term gain was introduced in the text associated with FIGS. 6 and 7. The gains can be changed through tapping the appropriate frozen ECG control buttons 300 (FIG. 11) in the manner described in the text associated with FIG. 6 in connection with changing the sweep speed. The time scale is provided by the sweep speed. When monitoring real-time data on the tablet computer 100 (FIG. 1), sweep speed serves as both the time scale and the speed of the sweep bar 234 (FIG. 5). There is, of course, no update or sweep bar 234 (FIG. 5) for a static printout. However, to maintain consistency between screen displays, sweep speed is used on all screen displays and printouts to designate the time scale. A set of static channel position icons 422 appear on each printed segment 420 of the data scroll to identify the channels of medical data. The set of static channel position icons 422 are not true icons but serve as channel labels in a format consistent with the screen displays.

In the preferred embodiment (not shown), the grid pattern consists of a major line every centimeter, a minor line every half centimeter, and a tick mark every millimeter. A simplified grid pattern of major lines without minor lines or ticks has been shown for ease of illustration. When using the preferred grid pattern, the gains would typically be in millivolts per centimeter, instead of millivolts per division. Using millivolts per centimeter and printing the output to scale allows amplitudes to be measured with a ruler.

On the laser-printed printout, two footnotes 424 are printed directly below the printed segment 420 of the data scroll that the footnotes 424 describe. Each footnote 424 has a footnote header 426 with the model number and serial number of the implantable medical device 116 (FIG. 1). The footnote header 426 also contains the date and start time of the printed segment 420 of the data scroll. Finally, the footnote header 426 includes a footnote header marker 428. The footnote header marker 428 is used to match the footnotes 424 to the corresponding footnote markers 430 on the printed segment 420 of the data scroll.

The footnotes 424 are printed in the order of the time value for each footnote marker 430. Thus, the footnote 424 labelled "C" is printed to the left of the footnote 424 labelled "B". If the printed segment 420 of the data scroll has three or more associated footnotes 424 then the first two footnotes 424 will print with the printed segment 420 of the data scroll. All additional footnotes 424 will be printed, two per page, on subsequent pages of the report with the appropriate print header 412 and parameter header 414, but without the printed segment 420 of the data scroll. For example, footnote A (not shown) is the third footnote from the printed segment 420 of the data scroll in FIG. 26, as indicated by the footnote marker 430 labeled "A" on the right side of the printed segment 420 of the data scroll. Footnote A will be printed on page seven of this full report (not shown except for miniature version in FIG. 28).

If two successive printed segments 420 of the data scroll are both free of footnotes 424, then the second printed segment 420 of the data scroll is printed below the first printed segment 420 of the data scroll to reduce the amount of paper used (printing of two printed segments 420 on one page not shown).

In an alternative embodiment, the scroll print request prints a limited number of printed segments 420 of the data scroll. The actual number of printed segments 420 would be set by a field service engineer. The subset of the data scroll would be centered around the segment of frozen data scroll being displayed at time of the full report print request. For example, if the segment width was set to print nine printed segments 420 of the data scroll, then four printed segments 420 of the data scroll would be allocated to printing material to the left of the segment of frozen data scroll being displayed and four printed segments 420 of the data scroll would be allocated to printing data to the right of the segment of data scroll being displayed at time of the print request.

However, if the segment of the data scroll being displayed is too close to either end of the data scroll to print the allotted amount, the full report would be re-centered to print the full number of printed segments 420 of the data scroll. For example, requesting a full report of nine printed segments 420 of the data scroll from screen display showing the segment within two segments of the right end of the data scroll effectively requests printing the rightmost nine printed segments 420 of the data scroll.

In a third embodiment, when the physician or medical specialist requests the full report associated with the particular display screen, the physician or medical specialist can select the entire frozen data scroll or choose one of several specified time durations. The tablet computer 100 (FIG. 1) converts the selected time duration to the number of printed segments 420 of the data scroll and then centers the full report as described above.

Another option for full reports allows the physician or medical specialist to choose the internal printer 170 (FIG. 3) as the print destination. The internal printer 170 (FIG. 3) is a conventional thermal printer that prints on strips of paper rather than sheets of paper. In the preferred embodiment, two strips from the internal printer 170 (FIG. 3) are used for information printed on one page by the laser printer 172 (FIG. 3). The advantage of the internal printer 170 (FIG. 3) is that the internal printer 170 (FIG. 3) is built into the base station 154 (FIG. 3) and some base stations 154 (FIG. 3) may not have an attached laser printer 172 (FIG. 3). However, not all reports lend themselves to being split for printing on two strips of paper.

Continuing with FIG. 26, if the laser print page of the full report can be reformatted into strips, the page is split into two strips, a full report upper strip 432 and a full report lower strip 434. These two strips 432 and 434 are printed on the internal printer 170 (FIG. 3). Optionally, users may mount the full report upper strip 432 and the full report lower strip 434 one above the other so that the end result resembles the output from the laser printer 172 (FIG. 3). The substance of the report is unchanged but depending on the amount of print header information and parameter header information that is necessary to describe the full report, some slight variations in format may exist between output for the laser printer 172 (FIG. 3) and the internal printer 170 (FIG. 3). The variations include differences in the spacing and positioning of printed matter to compensate for the division of the laser printout into two strips 432 and 434. The preferred embodiment does not allow the physician or medical specialist to print reports on the internal printer 170 (FIG. 3) that do not lend themselves to division into strips.

The footnote headers 426 allow the full report lower strips 434 to be matched with the corresponding full report upper strips 432. The parameter header 414 is not provided within the footnotes 424 on the lower strip 434 because the physician or medical specialist will read the footnote 424 in the context of the upper strip 432 which has the parameter header 414.

In the preferred embodiment, the tablet computer 100 (FIG. 1) is not attached directly or indirectly to a printer while the physician or medical specialist works with a patient. All print requests are stored in the print queue memory 148 (FIG. 2) of the tablet computer 100 (FIG. 1). The information necessary to create the print output is also stored in the print queue memory 148 (FIG. 2). This information includes copies of the relevant annotations as of the time of the print request, the sweep speed and gain settings, the relative positions of the channel position icons, and the information required for the print header 412 or 406 (FIG. 24) and the parameter header 414 or 408 (FIG. 24). To minimize memory requirements, the actual rendered image of the printout is not created until the tablet computer 100 (FIG. 3) is inserted into the base station 154 (FIG. 3).

Turning now to FIG. 27, the pending print requests are managed via the print queue menu as shown in FIG. 27. The physician or medical specialist can access the print queue menu by tapping a print review tab which is one the vertical tabs 202 (FIG. 4). The individual print requests are identified by print request names 436. The print request names 436 are each a combination of implantable medical device model number, implantable medical device serial number, date of print request, procedure during which the request was made, and time that the request was made. The procedures appearing in print request names 436 in FIG. 27 are V_capture threshold, V_sensitivity test, SIR Histogram, Measured Data, and Initial Interrogate. The name of the patient is provided to aid the physician or medical specialist in locating a particular print request since the print queue memory may hold print requests from several patients. The patient name is not necessary as part of the print request name since the combination of model number and serial number uniquely identifies the patent. As illustrated by the third patient on the print queue of FIG. 27, the patient's name may be unknown to the computer if the patient is new to a medical clinic. Implantable medical devices 116 (FIG. 2) may contain this information in the future but now provide only the model and serial number and not the patient name. Two additional attributes of the print request are provided. The first attribute is a printer destination 438.

The printer destination can be switched for those print reports that can be split into strips for printing on the internal printer 170 (FIG. 3). To switch printer destination 438, the physician or medical specialist uses the pen 102 (FIG. 1) to tap on the printer destination 438 for a particular print request. If the printout could be printed at the other destination, the print destination 438 will switch. For example, a single tap on the word "internal" in FIG. 27 will switch the printer destination for print request "2008L-07222-13-FEB-93 V_Capture_threshold-09:35:43."

The second print request attribute is a print report type 440. The print report type 440 cannot be altered but is displayed to aid locating a particular file. As discussed in the text associated with FIGS. 23–24, some screen displays can be printed as either a short report known as a summary report or as a full report. If the screen display can be printed only one way, the print report type 440 is simply "report."

The preview feature on the print screen allows the physician or medical specialist to view the print report request. Preview mode displays the report as it will be printed, but slightly smaller so that the pen icon bar (described below) and buttons (described below) relating to the preview mode can occupy a portion of the screen display.

Continuing with FIG. 27, the steps for previewing and annotating a page of a print request are as follows. In the first step, a preview button 442 at the bottom of the print queue menu is tapped. The regions of the digitizer display screen 104 (FIG. 1) below the displayed print request names 436 are now changed into implicit buttons.

In the next step, the pen 102 (FIG. 1) is moved towards the print request name 436 to be previewed. In the preferred embodiment, which uses a type of pen 102 (FIG. 1) that provides a proximity signal to the digitizer 108, a rectangle (not shown) is displayed as a visual aid for the physician or medical specialist. The rectangle appears when the pen 102 (FIG. 1) is within the sensing range of the digitizer display screen 104 (FIG. 1). Movement of the pen 102 (FIG. 1) moves the rectangle from one implicit button to the next.

Tapping the pen 102 (FIG. 1) on a queued print request name 436 selects the queued print request for preview. If the queued print request is a full report then the first image displayed is an overview fiche screen display of the entire full report as shown in FIG. 28.

Figure 28:
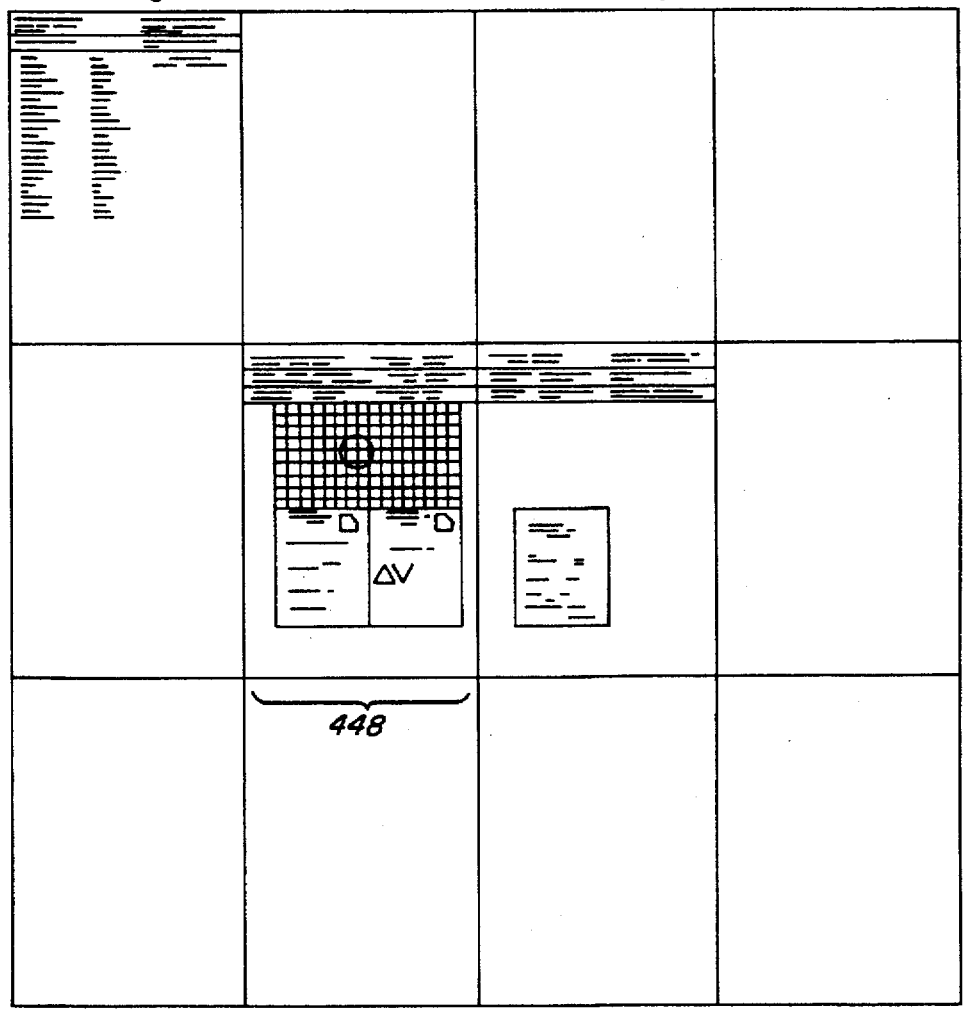
FIG. 28 contains selected portions of a screen display on the digitizer display screen containing the first of two overview fiches for a full report.

Turning now to FIG. 28, an overview of the full report that contains twenty-two pages would be split between two screen displays each containing an overview fiche 444. Images of pages one through twelve are produced on the overview fiche 444 on the first screen display. (To focus attention on the pages discussed in the specification only pages one, six and seven of the first twelve pages have been reproduced in FIG. 28.) The remaining pages of printout are produced on the overview fiche 444 on the second screen display (not shown). The second screen display is accessed by tapping a next fiche button 446 shown at the bottom of FIG. 28. Splitting the pages of printed output into multiple overview fiche 444 produces page images with sufficient detail to make a selection.

Tapping on a fiche image 448 of a printed page in the second column and second row of the array of page images selects a preview screen display as shown in FIG. 29.

Turning now to FIG. 29, page six of the twenty-two page print request was presented as FIG. 26 and is now shown as a page image portion 450 of the preview screen display. If the physician or medical specialist wishes to annotate the page image 450, the next step is tapping a zoom icon 452 on a pen tool icon bar 454. Note that the choice of icons on the pen tool icon bar 454 is not the same set of icons offered on previous screen displays. The zoom icon 452 symbol is a large "Z". An unzoom icon 456 uses the symbol of the same large "Z" covered with the circle and slash that is commonly used to represent "not". In an alternate embodiment (not shown), the zoom icon symbol is a magnifying glass enlarging one of three very small characters. The corresponding unzoom icon (not shown) has the same three very small characters from the alternative icon for zoom but without the magnifying glass or magnified letters. Another set of zoom and unzoom icons (not shown) use a the image of a magnifying glass with a "+" in the center of the magnifying glass for zoom and a "−" in the center of the magnifying glass for unzoom. Icons with very small letters or symbols have not been selected for use in the figures for ease of illustration.

Tapping on the zoom icon 452 allows the physician or medical specialist to enlarge a portion of the page image 450 through use of one of two gestures. The first gesture uses a tap of the pen 102 (FIG. 1).

Tapping the pen 102 (FIG. 1) on the page image 450 displays a new enlarged image (not shown) of the page image 450. The new enlarged page image (not shown) is centered on the point of pen tap contact. In the preferred embodiment, the magnification level is preset and alterations are made by a field service engineer. Subsequent tapping of the enlarged page image (not shown) causes the enlarged page image (not shown) to re-center on the new point of pen contact. In the preferred embodiment, subsequent tapping does not result in subsequent magnification. Excessive magnification would encourage the physician or medical specialist to add annotations that would be too small to read or reproduce when the annotations are printed proportional to the size of printout without magnification.

Figure 30:
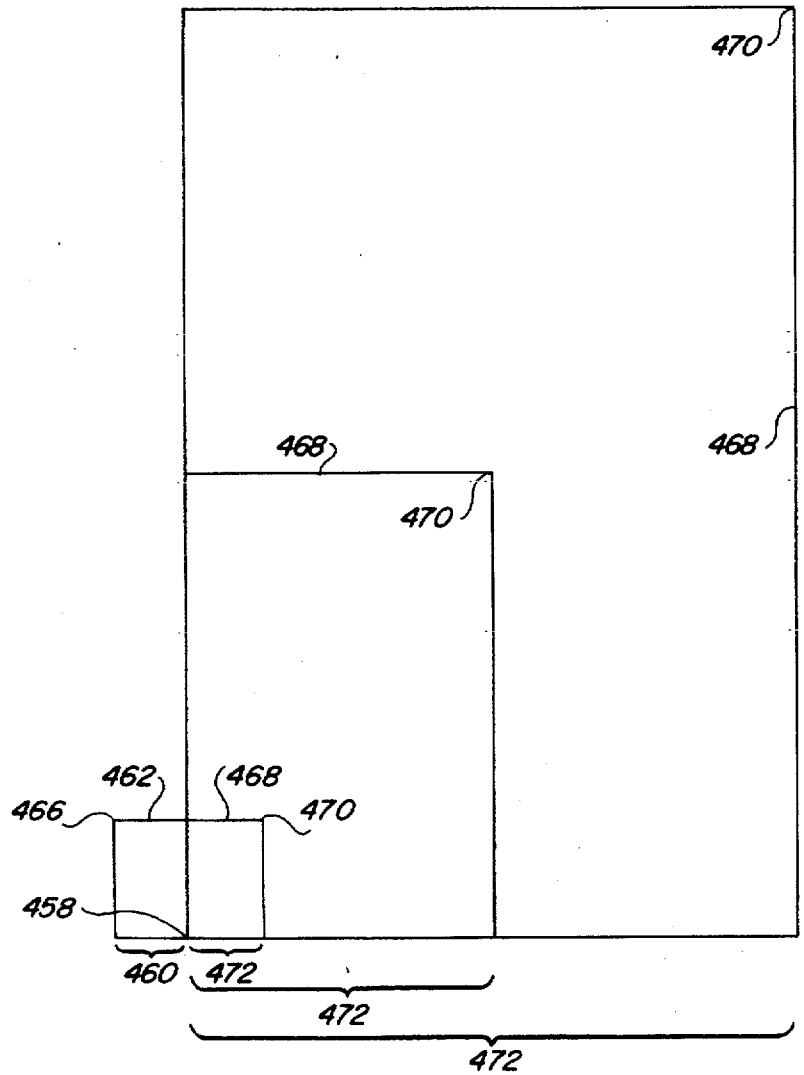
FIG. 30 is a series of four rectangles displayed to aid selection of the region of the page image to be magnified during a press and drag gesture.

The second method of selecting the region of the page image to magnify is a press and drag motion with the pen 102 (FIG. 1). Turning now to FIG. 30, the point of contact with the digitizer display screen 104 (FIG. 1) becomes the first corner 458. The tablet computer 100 (FIG. 1) forms a rectangle 460 based on the location of the first corner 458, the location of a particular chosen second corner 462, and the aspect ratio of a window 464 that holds the page image 450 (FIG. 29). The aspect ratio is the ratio of height to width. The tablet computer 100 (FIG. 1) calculates a calculated second corner 466 based on the chosen second corner 462 and the aspect ratio. The rectangle 460 is formed with the calculated second corner 466 on a diagonal from the first corner 458. The physician or medical specialist chooses the chosen second corner 462 by dragging the pen 102 (FIG. 1) to a location and then pressing and holding the pen 102 for at least one-half second.

Until the press and hold gesture is performed, the tablet computer 100 (FIG. 1) will display a stretching rectangle (not shown) that moves with the position of the pen 102 (FIG. 1). For purposes of illustration, FIG. 30 contains a series of additional chosen second corners 468 and a corresponding series of calculated second corners 470. The series of calculated second corners 470 and the first corner 458 form a series of rectangles 472.

After the press and hold gesture is performed, the tablet computer 100 (FIG. 1) expands the contents of the rectangle 460 or 472 to fill the window 464. Because the aspect ratio of the rectangle 460 or 472 is the same as the window 464, the magnification is performed without distortion. The tap gesture may be used after the press and drag gesture to reposition the magnified image.

The press and drag gesture allows the physician or medical specialist to choose a small section of the page image for magnification. The smaller the section selected, the greater the magnification required to fill the border of the page image portion of the preview screen display 464. Although the press and drag gesture allows a variety of magnification factors, in the preferred embodiment, there is a minimum size for the displayed rectangle 460 (or 472) to be magnified thus limiting the maximum magnification factor. This limitation prevents annotations of greatly magnified material. Such annotations tend to be illegible when printed at normal magnification.

Turning now to FIG. 31, once the physician or medical specialist has selected and enlarged a portion of the page image, the physician or medical specialist may annotate the page image. The preview annotation step is begun by tapping the pen 102 (FIG. 1) on the ink tool icon 348 on the pen tool icon bar 454.

When the physician or medical specialist adds a preview annotation 480 to the window 464 containing the page image portion of the preview screen display, these annotations are stored in a separate acetate layer memory (not shown).

This annotation acetate layer memory is stored in the processing and memory circuit 142 (FIG. 2) and is distinguishable from the digitizer input storage called the acetate layer memory 140 (FIG. 2). The preview annotations 480 are stored as vectors along with the horizontal and vertical position of the location on the printed page that corresponds to a point of initial contact 482 of the pen 102 (FIG. 1) to the digitizer display screen 104 (FIG. 1) during the annotation of the page image.

The tools available during preview annotation are the ink tool and the eraser tool. An important feature of the preview function is that the eraser tool can only erase annotations created during the preview session. The underlying data, print headers, parameter headers, and annotations that were added before the physician or medical specialist made the print request are all immune from erasure by the eraser tool.

Tapping the unzoom icon 456 allows the physician or medical specialist to view the entire page image 450 along with the new preview annotation 480. (unzoomed annotated image not shown) The physician or medical specialist may select another portion of the page image 450 (FIG. 29) for additional preview annotations.

An undo button 484 is used to delete the preview annotation 480 of the page image 450 (FIG. 29). If the page image 450 (FIG. 29) had received several preview annotations (none shown beyond 480) then all preview annotations would be deleted when the undo button 484 is tapped. Tapping the undo button 484 does not effect annotations created before the original print request or preview annotations (not shown) to other page images for pages within the same multipage report.

The preview screen shown in FIG. 31 has both the page forward button 332 and the page back button 334. These buttons 332 and 334 appear on the preview screen display when previewing a multipage print request. The page forward button 332 and the page back button 334 may be used at any time to move to the adjacent page. For example, the physician or medical specialist wishing to annotate the page image 450 (FIG. 29) of a multipage full report would probably first view the adjacent pages of the report to see the adjacent page images 450 (FIG. 29) including the contents of the footnotes 424 (FIG. 26).

Tapping an end preview button 488 causes the tablet computer 100 (FIG. 1) to return to the display screen containing the overview fiche 444 as shown in FIG. 28. The fiche image 448 of the overview fiche 444 would now include the preview annotation 480 (FIG. 31) (448 not shown in FIG. 28 with the preview annotation). Tapping the end preview button 488 in FIG. 28 saves the preview annotation 480 and all other preview annotations (not shown) then returns the display to the print queue menu shown in FIG. 27. As a shortcut, the end preview button 488 on FIG. 31 can be tapped with the page image 450 in a magnified state, thus avoiding the intermediate step of tapping the un-zoom icon 456.

Continuing with FIG. 27, after previewing the print request, the physician or medical specialist may decide to delete that print request. Alternatively, the physician or medical specialist may have made a second print request for a full report after adding additional annotations and now wishes to delete the first print request.

Tapping a delete button 490 turns the pen 102 (FIG. 1) into a deletion tool. Tapping the pen 102 (FIG. 1) on a print queue line number 492 causes the print queue line number 492 to be replaced with "DEL". Tapping on "DEL" will cause "DEL" to be replaced with the print queue line number 492 thereby canceling the deletion. Tapping a close button 496 closes the print queue menu and deletes any print requests preceded by "DEL" instead of the print queue line number 492. For example, tapping the close button 496 on FIG. 27 would delete the second print request for patient John B. Goode.

In addition to the various print functions, a "save" function creates a copy of all information and annotations for a particular patient. The only exception to the "save all" rule is that the contents of the current buffer (discussed in connection with FIG. 11) are not saved. However, the contents of the current buffer can be copied into the frozen ECG buffer by tapping the freeze button 298 (FIG. 11). The frozen ECG buffer is saved during the execution of a save function.

Returning briefly to FIG. 23, a save button 498 is one of the series of buttons 210 on the top of many screen displays. The save function is useful when the physician or medical specialist does not have time to examine and annotate frozen medical data and wishes to do so later. For example, some medical procedures cause discomfort. The physician or medical specialist may wish to continue the exam rather than continue annotating the results while the patient is uncomfortable. In some situations, the patient's situation may change too quickly to fully annotate the results such as when the tablet computer 100 (FIG. 1) is used in an emergency room or operating theatre. A third possibility is that the physician or medical specialist may want to capture the complete set of data for discussion with peers or students. In all of these situations, the ability to quickly save all medical data, screen settings, and annotations is important.

In the preferred embodiment the physician or medical specialist is not allowed to select which screen displays, frozen data scrolls, or other material is saved. All information that is relevant to the patient is saved. In the preferred embodiment, the physician or medical specialist who requests another save after making just one minor change to one screen display saves an entire set of data, display screens, and related material. Although this may seem inefficient, the advantages of speed, simplicity of commands, and assurance of capturing all necessary information outweigh the disadvantage of storing some unwanted or redundant information.

Turning now to FIG. 32, the save catalog menu lists the sets of saved data. The sets of saved data are identified by a saved set name 500 comprising a model number and a serial number of the implantable medical device coupled with a date and a time when the data was saved. If known to the tablet computer 100 (FIG. 1), a name of the patient is provided as an aid to physician or medical specialist in finding a particular patient's data.

Figure 33:
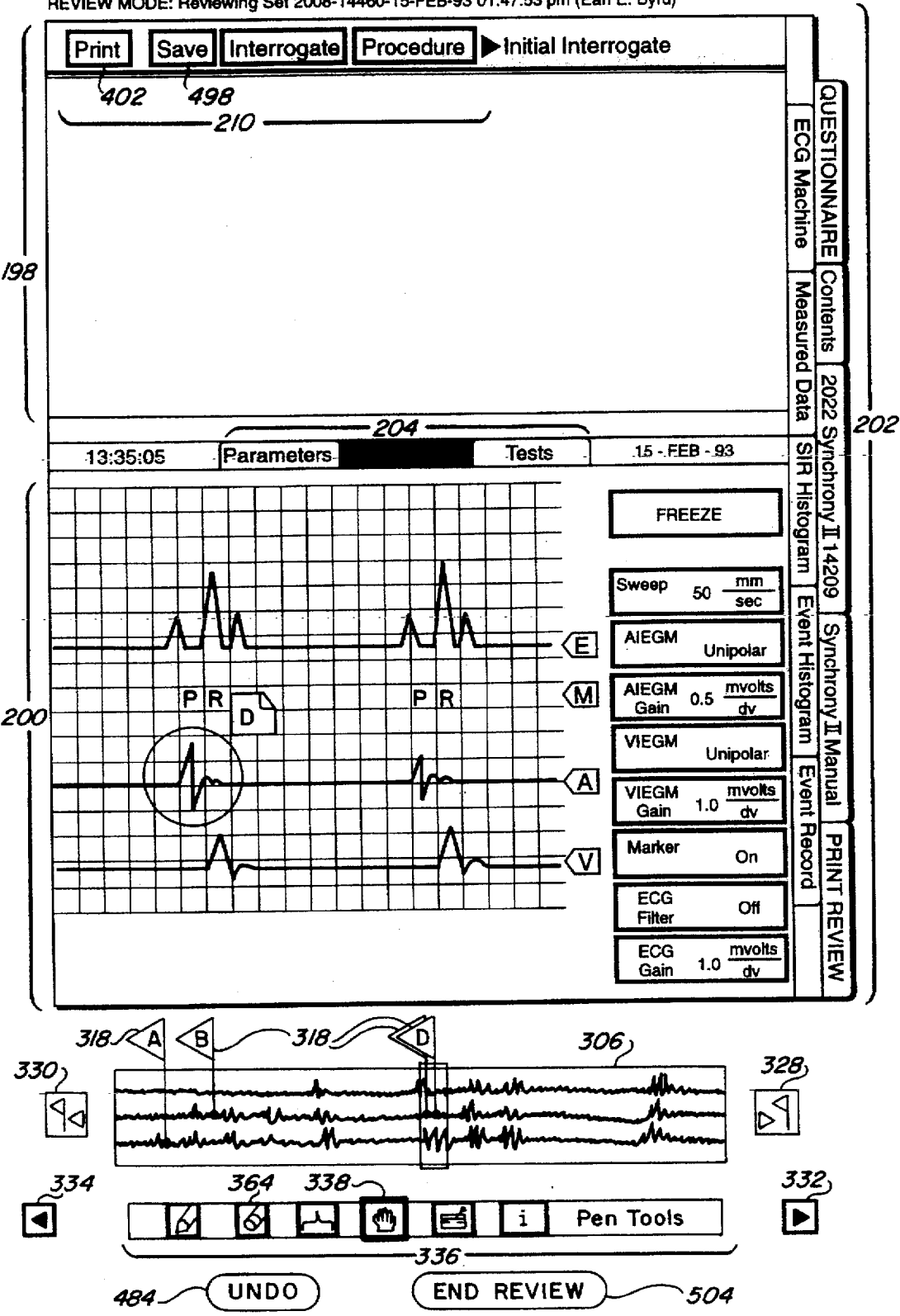
FIG. 33 is a screen display on the digitizer display screen for review of a set of saved data and saved screen displays.

Tapping a review button 502 and then tapping on the saved set name 500 of the desired set of saved data will return the physician or medical specialist to the screen display that was open when the save request was made. Turning now to FIG. 33, the tablet computer 100 (FIG. 1) is now in review mode. The physician or medical specialist does not need to learn a new set of commands to operate review mode. The physician or medical specialist has a familiar screen display with the series of buttons 210 including the save button 498 and the print button 402 so that the changes made during review mode can be saved or printed. The physician or medical specialist can move to other screen displays through the use of the vertical tabs 202, or horizontal tabs 204.

Movement within the frozen data in lower window 200 is done through the physician's or medical specialist's choice of the page forward 332, page back 334, flag jump right 328, flag jump left 330, or through the use of the hand tool icon 338 found on the pen tool icon bar 336.

The physician or medical specialist may add new ink annotations or footnote annotations. The new annotations will be marked by additional flags 318 in the compressed buffer overview 306. The physician or medical specialist may erase existing annotations by using the pen 102 (FIG. 1) as the eraser tool after tapping the eraser tool icon 364.

Because this is stored data, the physician or medical specialist cannot view current data in the upper window 198 or reprogram the implantable medical device 116 (FIG. 2). During the review of saved data, the undo button 484 and an end review button 504 appear on all review screen displays. The undo button 484 deletes all modifications made to that particular review screen display during the review of saved data. Tapping the undo button 484 does not affect changes made to other screen displays during the review session. Tapping the end review button 504 terminates the review session and stores all changes to the existing set of saved data. Tapping the end review button 504 returns the display to the save catalog menu (as shown in FIG. 32). Subsequent review of this same saved data set will start at the screen display that the physician or medical specialist was viewing when the physician or medical specialist tapped the end review button 504. Subsequent reviews will show the annotations as modified during prior reviews of the same saved data.

Returning now to FIG. 32, tapping the delete button 490 and then tapping on a save catalog line number 506 causes the letters "DEL" appear in place of the selected save catalog line number 506. Tapping the letters "DEL" will cause the letters "DEL" to disappear, and the selected save catalog line number 506 to reappear. In this case the save catalog line number 506 that can reappear is "3)".

The physician or medical specialist exits from the save catalog menu by tapping the close button 496. Tapping the close button 496 deletes all sets of saved data currently marked with "DEL".

The preceding discussion has focused on working with sources of recorded and real-time electronic measurements of medical data. Another major source of medical data is questionnaires that collect patient history and other material. Consequently, one important feature of the user interface is the method of entering information from patient questionnaire cards. One way to make efficient use of the physician's or medical specialist's time is to have patients complete medical history questionnaires before meeting with the physician or medical specialist. Alternatively, the medical questionnaire could be filled out by an assistant to the physician or medical specialist based on the responses given by the patient. Another alternative embodiment (not shown) displays the image of the questionnaire card on the digitizer display screen 104 (FIG. 1) for direct entry of the information without use of a separate card.

Traditionally, such questionnaires were reviewed by the physician or medical specialist for unusual responses and then filed with the patient's records. The improved user interface of the present invention allows such information to be entered into the patient's medical history while it is being reviewed by the physician or medical specialist. Once entered, the medical history information can be compared to prior responses by the same patient so that changes can be highlighted. Alternatively, the patient questionnaire can be used as input to diagnostic aid programs.

Returning to FIG. 4, to enter the responses into the tablet computer 100 (FIG. 1), the physician or medical specialist first taps one of the vertical tabs 202, specifically a tab labeled "questionnaire" 508. Tapping the vertical tab labeled "questionnaire" 508 changes the display to a questionnaire selection menu as shown in FIG. 34.

Turning now to FIG. 34, a list of questionnaires 510 used by that medical facility is presented to the physician or medical specialist. New responses from a patient are entered by first tapping on an input button 512 and then selecting a particular questionnaire. Tapping the pen 102 (FIG. 1) on one of the questionnaire names triggers the implicit button underneath the displayed name. The questionnaire selection menu has two other explicit buttons.

One explicit button is a close button 514. Tapping the close button 514 returns the physician or medical specialist back to the screen display where the physician or medical specialist tapped the vertical tab labeled "questionnaire" 508 (FIG. 4).

The first step in entering patient answers to the questionnaires is having the patient fill out a series of questionnaire cards before meeting with the physician or medical specialist. Turning now to FIG. 35, after selecting the particular questionnaire from the questionnaire selection menu in FIG. 34 corresponding to the series of questionnaire cards that the patient has filled out, the physician or medical specialist places a questionnaire card 516 against the left side of the digitizer display screen 104.

The tablet computer 100 (FIG. 1) displays a set of received responses 518 on an uncovered portion 520 of the digitizer display screen 104 not covered by the questionnaire card 516. The default settings have the questionnaire card 516 against the left edge of the digitizer display screen 104 with the uncovered portion 520 of the digitizer display screen 104 on the right side. The default value can be switched as part of the profile for the physician or medical specialist if the physician or medical specialist prefers the uncovered portion 520 on the left. The physician or medical specialist taps on the patient's marked responses with the pen 102 (FIG. 1), thus activating implicit buttons in the digitizer display screen 104. The implicit buttons translate responses for this particular questionnaire card into the set of received responses 518. An audible tone from the speaker 146 (FIG. 2) in the tablet computer 100 (FIG. 1) confirms receipt of each response. Entries can be immediately corrected by re-entering the correct response. For example, the response "always" to question three may be corrected by tapping on the appropriate response in the "sometimes" column.

In the preferred embodiment, the digitizer 108 (FIG. 1) can sense the pen tip 110 (FIG. 1) through the questionnaire card 516 if the pen tip 110 (FIG. 1) is within approximately one-quarter inch of the digitizer display screen 104. Thus, the questionnaire card 516 does not need holes at the responses to allow contact between pen tip 110 (FIG. 1) and the digitizer display screen 104. In an alternative embodiment, the digitizer 108 is a pressure sensitive digitizer and the questionnaire card 516 is comprised of a material sufficiently pliable to allow a pressure sensitive digitizer to receive input through the questionnaire card 516. In yet another embodiment, (not shown) the digitizer and pen are of the type where the pen is connected to the digitizer by a cord containing one or more conductive wires. In this "wired" embodiment the questionnaire card 516 is made of a material that allows the digitizer to receive input from a pen connected to the digitizer by one or more conductive wires (digitizer and pen connected to the digitizer by one or more conductive wires not shown).

Optionally, the questionnaire card 516 could contain a frame (not shown) to contribute stiffness to the questionnaire card 516 to make the questionnaire card 516 easier to handle and place on the digitizer display screen 104. The frame would not have to be made of material that is suitable for passing input to the digitizer from the corresponding input pen for that type of digitizer.

The high resolution of the digitizer 108 (FIG. 1), combined with the ability of the physician or medical specialist to precisely place the pen tip 110 (FIG. 1) permits the implicit buttons to be very small. Implicit buttons can be very small because, unlike the explicit buttons, they are not constrained by the size of the labels for the explicit buttons. These very small implicit buttons allow the questionnaire card to seek responses that include numbers, letters, or choices on a continuum bar 522 in addition to multiple choice question responses. For example, small densely packed buttons allow the numbers and letters in the model and serial number to be entered in a small portion of the questionnaire card 516. Entry of this same information with a touch screen computer would require either a great number of screen displays or a more elaborate increment/decrement method for entry.

Small densely packed buttons positioned underneath the continuum bar 522, can translate the response to question ten into a value without requiring an explicit choice for each possible value for question ten on the questionnaire card 516. Of course, even the very small buttons placed under the continuum bar 522 form a finite number of possible choices and only appear to offer a true continuum of possible responses.

A series of four explicit buttons 524 are provided on the uncovered portion of the digitizer display screen 520. Tapping a next button 526 causes the tablet computer 100 (FIG. 1) to move to the screen display for the next questionnaire card in that series of questionnaire cards. Tapping a back button 528 moves the tablet computer 100 (FIG. 1) back to the screen display for the preceding page of the questionnaire. The back button 528 facilitates corrections to the data when the interview between the physician or medical specialist and the patient discloses that the patient misunderstood a question. Tapping on the back button 528 while on page one of the questionnaire recalls the questionnaire selection menu (shown in FIG. 34). Tapping a clear button 530 erases all entries on the current screen display.

Tapping on a close button 532 saves all responses entered during the input session, ends the questionnaire answer input session and returns the tablet computer 100 (FIG. 1) to the questionnaire selection menu (shown in FIG. 34). The close button 532 can be used from any screen display in the series of screen displays used to input the questionnaire answers. The physician or medical specialist can stop entering answers, use the tablet computer 100 (FIG. 1), and then resume entry of questionnaire answers. To resume, the physician or medical specialist would choose the tab 508 labeled questionnaire (FIG. 4), then tap a review responses button 534 (FIG. 34). Tapping the review responses button 534 (FIG. 34) moves the physician or medical specialist to a screen display (not shown) having a list of all sets of questionnaire responses that are in the tablet computer processing and memory circuit 142 (FIG. 2) or general memory unit 150 (FIG. 2). Retrieval of stored responses is similar to the use of the print queue menu (described in the text associated with FIG. 27) or the save catalog menu (described in the text associated with FIG. 32). To resume entry of answers to a particular questionnaire, the physician or medical specialist would view the list of questionnaires with responses, select the partially filled questionnaire, and tap the next button 526 repeatedly on each successive screen display corresponding to the series of questionnaire cards until the screen display is showing the appropriate screen display for resuming entry of the remaining responses.

Figure 36:
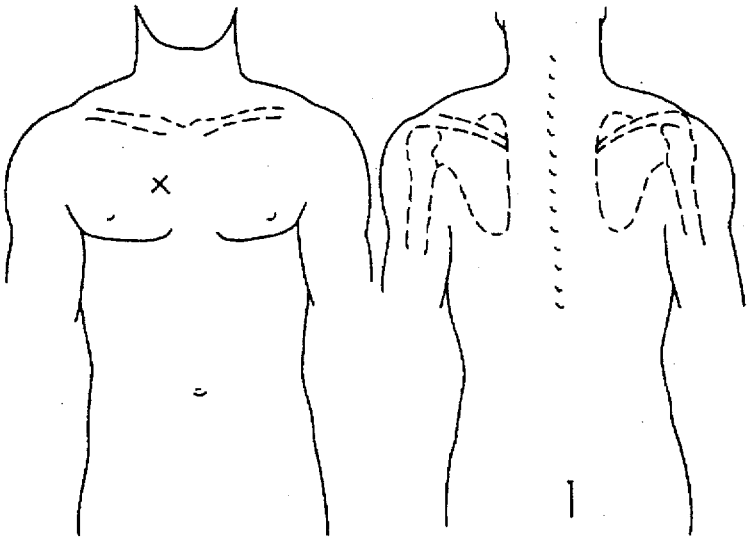
FIG. 36 is a screen display on a digitizer display screen partially covered by another questionnaire card used to input specific torso locations that were sites of discomfort during a cardiac incident.

Turning now to FIG. 36, densely packed implicit buttons make it possible for a patient to designate the specific regions that experienced discomfort during prior cardiac incidents on a questionnaire card. On a preprinted questionnaire card 516, the patient marks the date, year, and time of the cardiac incident. Additionally, the patient can mark the areas that experienced discomfort on preprinted images 536 of the human torso. Through the use of densely packed buttons and the preprinted images 536 on the questionnaire card 516, the patient can convey important information without the confusion induced by attempting to describe the locations with words.

The use of the preprinted images 536 is superior to a system that provides the patient with correct medical terms for each region of the body. Such a system would be prone to error since many patients do not know the correct anatomical names of the parts of the body.

The set of received responses 518 is displayed in the uncovered portion 520 of the digitizer display screen 104. Additionally, a model and serial number 538 of the implantable medical device 116 (FIG. 2), which was entered on the first questionnaire card 516, is displayed to identify the patient. This displayed information ensures questionnaire responses are entered into the correct patient's records.

Underneath the actual questionnaire card 516 on the display 106 (FIG. 1) of the digitizer display screen 104, an image 540 of the questionnaire card 516 is displayed. As responses are entered by tapping on the questionnaire card 516, the response is overlaid on the image 540 of the questionnaire card 516 on the digitizer display screen 104. This serves two purposes. The image 540 of the questionnaire card 516 on the digitizer display screen 104 ensures that the correct questionnaire card 516 is being placed on the corresponding input screen display. The second advantage of displaying the image 540 of the questionnaire card 516 is when the received responses are overlaid on the image 540, the physician or medical specialist can remove the questionnaire card 516 from the digitizer display screen 104 to review the received responses on the image 540. Thus, very small versions of the torso images do not need to be displayed in the uncovered portion 520 of the digitizer display screen 104 along with the set of received responses 518.

A logical extension of the capacity of the user interface to accept free-form annotations and the use of questionnaire cards is to combine the two features. The system could use questionnaire cards that solicited comments from the patient. These comments along with the notes from the physician or medical specialist could be added to the electronic records for the patient. However, the preferred embodiment of the user interface does not do so. The patient input questionnaire is used to quickly provide information that is useful for screening the patient. Thus annotations as appropriate can be included on the card and discussed with the physician or medical specialist. The annotations on the questionnaire will be saved in the patient's file with the entire set of questionnaire cards.

After the entire series of questionnaire cards has been entered into the tablet computer 100 (FIG. 1), a button (not shown) appears. The button (not shown) provides the physician or medical specialist with the ability to print a copy of the received responses 518 to the patient questionnaire. Normally, printing will not be required since the patient's answers are available on the series of questionnaire cards 516. The series of completed questionnaire cards 516 can be filed in the paper copy of the patient records.

Several alternative embodiments of this invention are possible. Many of the teachings of this invention can be applied to a computer that is not a tablet computer 100 (FIG. 1). For example, a desktop computer (not shown) with a display (not shown) and a digitizer (not shown) could allocate a portion of the digitizer to perform the task of the digitizer 108 in FIG. 2. Templates may be used to identify portions of the digitizer that are allocated to various icons, explicit buttons, or tabs.

An advantage of a desktop computer is the keyboard of the desktop computer could be used for the text portions of the annotations. A disadvantage of desktop computer (not shown) with a digitizer (not shown) that is separate from the display (not shown) is the fatigue caused by alternatively looking at the digitizer then at the display. This fatigue can be reduced by providing a visual indication on the display of the position of the pen on the digitizer that corresponds to the display. Thus, allowing the physician or medical specialist to watch the display rather than alternating between the display and the digitizer. For example, a system could make extensive use of rectangles around the sensed location of the pen as was described for implicit buttons (text accompanying FIG. 4). A set of cross hairs 354 (FIG. 14) could be used during operations such as annotation where a rectangle would be inappropriate.

Another variation in the application of this invention involves the type of data that forms the basis of the data scroll. This disclosure focused on a data scroll that stored the digitized values of surface ECG, AIEGM, VIEGM, and the symbols from the marker data channel. These values were stored as a function of time. The graphic presentation was consistently the four channels as dependent variables with time as the independent variable on a cartesian coordinate graph. However, this invention does not require the independent variable to be time. For example, the independent variable could be a function of time such as a logarithmic function of time, or the independent variable could be heart beats with the dependent variable being time between heart beats. Of course, the variables could be unrelated to cardiac monitoring.

The accompanying figures in this application have consistently shown the independent variable on the horizontal axis with the scale ascending from left to right. These conventions are not inherent limitations in the invention, and the invention would work with cultures or disciplines that have other preferences. The invention applies to any graphic method of displaying information including three dimensional graphs, graphs that use radial or cylindrical coordinates, and spreadsheets of medical data.

Thus an improved user interface for an implantable medical device using an integrated digitizer display screen has been provided. One skilled in the art will appreciate that the present invention can be practiced by other than the described embodiments, which are presented for purposes of illustration and not of limitation, and the present invention is limited only by the claims which follow.

What is claimed is:

1. An analyzer-programmer for use with an implantable medical device, said analyzer-programmer comprising:

circuitry for receiving information pertaining to a patient's medical condition and an implantable medical device implanted in said patient, said circuitry for receiving information including a telemetry circuit for enabling transmissions between said analyzer-programmer and said implantable medical device;

a digitizer pen input device;

an integrated digitizer display screen unit for displaying an image representative of said information and for receiving hand-written input through use of said digitizer pen input device by direct placement of a pen tip of said digitizer pen input device on said integrated digitizer display screen unit; and a processor circuit for selectively adjusting said displayed image and said transmissions between said analyzer-programmer and said implantable medical device in accordance with input received by said integrated digitizer display screen unit through use of said digitizer pen input device.

2. The analyzer-programmer of claim 1, wherein said information includes a channel of information selected from the group consisting of a surface ECG, an atrial IEGM, a ventricular IEGM, and marker data.

3. The analyzer-programmer of claim 1, wherein:
   said circuitry for receiving information comprises means for receiving a plurality of channels of information; and
   said processor circuit causes said digitizer display screen unit to concurrently display images representative of at least two of said plurality of channels of information on a common time line.

4. The analyzer-programmer of claim 1, wherein:
   said processor circuit causes said integrated digitizer display screen unit to display a channel position icon in association with said image representative of said information in a first set of locations; and
   said processor circuit causes said integrated digitizer display screen unit to display said channel position icon and said image representative of said information in a second set of locations in accordance with input provided to said integrated digitizer display screen unit through use of said digitizer pen input device.

5. The analyzer-programmer of claim 1, wherein said processor circuit causes said telemetry circuit to transmit commands to said implantable medical device in response to input provided to said integrated digitizer display screen unit through use of said digitizer pen input device, said commands defining operating characteristics of said implantable medical device.

6. The analyzer-programmer of claim 1, wherein said processor circuit:
   causes said integrated digitizer display screen unit to display an image that includes a region defining a button; and
   adjusts said displayed image and said transmissions between said analyzer-programmer and said implantable medical device in response to input provided to said integrated digitizer display screen unit through use of said digitizer pen input device, wherein said digitizer pen input device provides input when said pen tip of said digitizer pen input device is placed on said integrated digitizer display screen unit in a vicinity of said button.

7. The analyzer-programmer of claim 1, wherein said processor circuit:
   responds to a gesture input through use of said digitizer pen input device on said integrated digitizer display screen unit; and
   adjusts said displayed image and said transmissions between said analyzer-programmer and said implantable medical device in response to said gesture input to said integrated digitizer display screen unit.

8. The analyzer-programmer of claim 7, wherein said processor circuit causes said integrated digitizer display screen unit to display a first segment of said information as a graph having a dependent variable axis and an independent variable axis and causes said integrated digitizer display screen unit to display a second segment of said information in place of said first segment in response to said gesture input.

9. The analyzer-programmer of claim 8, wherein said second segment includes a portion of said first segment.

10. The analyzer-programmer of claim 9, wherein said processor circuit in causing said integrated digitizer display screen unit to display a first segment of said information, selects an end of said second segment based on a location of said gesture on said integrated digitizer display screen unit.

11. The analyzer-programmer of claim 1, further comprising a memory circuit for storing data corresponding to said information.

12. The analyzer-programmer of claim 11, wherein said memory circuit comprises a wrap-around buffer for storing a predetermined amount of said data corresponding to said information.

13. The analyzer-programmer of claim 12, wherein:
   said memory circuit further comprises a frozen electronic data scroll; and
   said processor circuit:
   copies said predetermined amount of data stored in said wrap-around buffer to said frozen electronic data scroll in response to input provided to said integrated digitizer display screen unit through use of said digitizer pen input device.

causes said integrated digitizer display screen unit to display an image representative of a first segment of said predetermined amount of data stored in said frozen electronic data scroll, and causes said integrated digitizer display screen unit to display an image representative of a second segment of said predetermined amount of data stored in said frozen electronic data scroll in response to input provided to said integrated digitizer display screen unit through use of said digitizer pen input device.

14. The analyzer-programmer of claim 11, wherein said processor circuit:

causes said integrated digitizer display screen unit to display a graphical representation of said data stored in said memory in a compressed format; and causes said integrated digitizer display screen unit to concurrently display a first selected segment of said data in an expanded format, said first selected segment being selected in response to input provided to said integrated digitizer display screen unit through use of said digitizer pen input device.

15. The analyzer-programmer of claim 14, wherein said processor circuit stores identification markers in said memory circuit which mark selected data of said data stored in said memory circuit, said selected data being selected in response to input provided to said integrated digitizer display screen unit through use of said digitizer pen input device.

16. The analyzer-programmer of claim 15, wherein said processor circuit causes said integrated digitizer display screen unit to display symbols on said compressed graphical representation of said data stored in said memory circuit, said symbols being representative of said identification markers.

17. The analyzer-programmer of claim 16, wherein said processor circuit causes said integrated digitizer display screen unit to display a second selected segment of said data stored in said memory circuit, said second selected segment containing data identified by one of said identification markers.

18. The analyzer-programmer of claim 11, wherein said processor circuit:

causes said integrated digitizer display screen unit to display an image comprising a representation of said data;

receives a hand-written annotation associated with said displayed representation of said data, said annotation received through said integrated digitizer display device by use of said digitizer pen input device;

links said annotation with a selected portion of said data; and stores said linked annotation in said memory circuit.

19. The analyzer-programmer of claim 18, wherein said processor circuit creates one or more page-images to be printed, said page-images containing said linked annotation and said selected portion of said data.

20. The analyzer-programmer of claim 18, wherein said processor circuit causes said integrated digitizer display screen unit to display said linked annotation with said selected portion of said data.

21. The analyzer-programmer of claim 20, wherein said processor circuit selectively deletes portions of said linked annotation in response to input provided to said integrated digitizer display screen unit through use of said digitizer pen input device without deleting any of said data or any of said displayed representation of said data.

22. The analyzer-programmer of claim 18, wherein said processor circuit causes said integrated digitizer display screen unit to display a marker with said selected portion of said data, said marker being representative of said linked annotation.

23. The analyzer-programmer of claim 18, wherein said processor circuit causes said integrated digitizer display screen unit to display the representation of said selected portion of said data, wherein the selection for display of said selected portion of said data is based on the existence of said linked annotation, and the selection of said selected portion of said data is in response to input provided to said integrated digitizer display screen unit through use of said digitizer pen input device.

24. The analyzer-programmer of claim 18, wherein said processor circuit causes said integrated digitizer display screen unit to display a note pad for receiving said annotation of said displayed representation of said data.

25. The analyzer-programmer of claim 11, wherein said processor circuit:

creates a page-image to be printed containing a representation of said data;

causes said integrated digitizer display screen unit to display said page-image to be printed; receives a hand-written annotation corresponding to said displayed page-image, said annotation received through said integrated digitizer display device by use of said digitizer pen input device; and stores in said memory circuit said annotation of said page-image such that said page-image and said annotation are combined when printed.

26. An analyzer for facilitating analysis of information concerning an implantable medical device, said analyzer comprising:

a digitizer pen device;

a memory for storing information pertaining to a patient's medical condition and an implantable medical device implanted in said patient;

an integrated digitizer display screen unit for displaying an image representative of said information and for receiving hand-written input through use of said digitizer pen input device by direct placement of a pen tip of said digitizer pen input device on said integrated digitizer display screen unit; and a processor circuit for selectively adjusting said displayed image and said information stored in said memory in accordance with input received through use of said digitizer pen input device, said processor circuit:

causing said integrated digitizer display screen unit to display a graphical representation of said stored information in a compressed format, and causing said integrated digitizer display screen unit to concurrently display a graphical representation of a first selected segment of said information stored in said memory in an expanded format, said first selected segment being selected in response to input provided to said integrated digitizer display screen unit through use of said digitizer pen input device.

27. The analyzer of claim 26, wherein said processor circuit stores identification markers in said memory which mark selected portions of said information stored in said memory, said selected portions being selected in response to input provided to said integrated digitizer display screen unit through use of said digitizer pen input device.

28. The analyzer of claim 27, wherein said processor circuit causes said integrated digitizer display screen unit to display symbols on said compressed graphical representation of said information stored in said memory, said symbols being representative of said identification markers.

29. The analyzer of claim 28, wherein said processor circuit causes said integrated digitizer display screen unit to display a second selected segment of said information stored in said memory, said second selected segment containing information identified by one of said identification markers.

30. The analyzer of claim 26 further comprising circuitry for receiving said information from a source selected from the group consisting of a wireless communication link, a unit of memory storage media and a modem.

31. The analyzer of claim 26, wherein said processor circuit:

causes said integrated digitizer display screen unit to display an image comprising a representation of said information stored in said memory;

receives a hand-written annotation associated with said displayed representation of said information stored in said memory, said annotation received through said integrated digitizer display device by use of said digitizer pen input device;

links said annotation with a selected portion of said information stored in said memory; and stores said linked annotation in said memory.

32. The analyzer of claim 31, wherein said processor circuit creates one or more page-images to be printed, said page-images containing said linked annotation and said selected portion of said information stored in said memory.

33. The analyzer of claim 31, wherein said processor circuit causes said integrated digitizer display screen unit to display said linked annotation with said selected portion of said information stored in said memory.

34. The analyzer of claim 33, wherein said processor circuit selectively deletes portions of said linked annotation in response to input provided to said integrated digitizer display screen unit through use of said digitizer pen input device without deleting any of said information stored in said memory or any of said displayed graphical representation of said first selected segment of said information stored in said memory.

35. The analyzer of claim 31, wherein said processor circuit causes said integrated digitizer display screen unit to display a marker with said selected portion of said information, said marker being representative of said linked annotation.

36. The analyzer of claim 31, wherein said processor circuit causes said integrated digitizer display screen unit to display the representation of said selected portion of said information, wherein the selection for display of said selected portion of said information is based on the existence of said linked annotation, and the selection of said selected portion of said information is in response to input provided to said integrated digitizer display screen unit through use of said digitizer pen input device.

37. The analyzer of claim 31, wherein said processor circuit causes said integrated digitizer display screen unit to display a note pad for receiving said annotation of said displayed representation of said information stored in said memory.

38. A method of communicating with an implantable medical device implanted in a patient, comprising the steps of:

receiving information pertaining to a patient's medical condition and an implantable medical device implanted in said patient, at least a portion of said received information being received through a telemetry circuit from said implantable medical device;

storing said received information in a memory;

displaying an image representative of said information on an integrated digitizer display screen unit;

receiving hand-written input to said integrated digitizer display screen unit from a digitizer pen input device through use of said digitizer pen input device by direct placement of a pen tip of said digitizer pen input device on said integrated digitizer display screen unit; and modifying said displayed image and said stored information in accordance with input received by said integrated digitizer display screen unit through use of said digitizer pen input device.

39. The method of claim 38 wherein:

said step of receiving information comprises the step of receiving a plurality of channels of information;

said step of displaying an image comprises the step of concurrently displaying images representative of at least two of said plurality of channels of information on a common time line; and said step of modifying comprises the step of repositioning one of said images representative of one of said channels of information relative to another of said images representative of another of said channels of information.

40. The method of claim 38 further comprising the steps of:

selecting commands to be transmitted to said implantable medical device based on input provided to said integrated digitizer display screen unit through use of said digitizer pen input device;

transmitting said selected commands to said implantable medical device using said telemetry circuit, said transmitted commands defining operating characteristics of said implantable medical device.

41. The method of claim 38, wherein said step of modifying comprises the step of modifying said said displayed image and said stored information in response to a gesture input through use of said digitizer pen input device on said integrated digitizer display screen unit.

42. The method of claim 38, wherein said step of displaying an image comprises the steps of:

displaying a graphical representation of said stored information on said integrated digitizer display screen unit in a compressed format; and concurrently displaying a first selected segment of said information in an expanded format, said first selected segment being selected in response to input provided to said integrated digitizer display screen unit through use of said digitizer pen input device.

43. The method of claim 38 wherein:

said step of displaying an image comprises the step of displaying an image that includes a region defining a button; and said step of modifying comprises the step of modifying said said displayed image and said stored information in response to input provided to said integrated digitizer display screen unit through use of said digitizer pen input device, wherein said input device provides input when said pen tip of said digitizer pen input device is placed on said digitizer display screen unit in a vicinity of said button.

44. The method of claim 38 further comprising the step of receiving a hand-written annotation associated with said displayed representation of said stored information, said annotation received through said integrated digitizer display screen unit by use of said digitizer pen input device.

45. The method of claim 44 further comprising the steps of:

linking said annotation with a selected portion of said displayed representation of said stored information, said selected portion being selected by input provided to said integrated digitizer display screen unit through use of said digitizer pen input device; and storing said linked annotation in said memory.

46. An analyzer-programmer for use with an implantable medical device, said analyzer-programmer comprising:

circuitry for receiving information pertaining to a patient's medical condition and an implantable medical device implanted in said patient, said circuitry for receiving information including a telemetry circuit for enabling transmissions between said analyzer-programmer and said implantable medical device;

a digitizer pen input device;

an integrated digitizer display screen unit for displaying an image representative of said information and for receiving hand-written input through use of said digitizer pen input device by direct placement of a pen tip of said digitizer pen input device on said integrated digitizer display screen unit; and a processor circuit for selectively adjusting said displayed image and said transmissions between said analyzer-programmer and said implantable medical device in accordance with input received by said integrated digitizer display screen unit through use of said digitizer pen input device; and wherein said processor circuit responds to a hand-written gesture input through use of said digitizer pen input device on said integrated digitizer display screen unit; and adjusts said displayed image and said transmissions between said analyzer-programmer and said implantable medical device in response to said gesture input to said integrated digitizer display screen unit.

47. The analyzer-programmer of claim 46, wherein said processor circuit:

responds to a gesture input through use of said digitizer pen input device on said integrated digitizer display screen unit; and adjusts said displayed image and said transmissions between said analyzer-programmer and said implantable medical device in response to said gesture input to said integrated digitizer display screen unit.

48. The analyzer-programmer of claim 46, wherein said processor circuit causes said integrated digitizer display screen unit to display a first segment of said information as a graph having a dependent variable axis and an independent variable axis and causes said integrated digitizer display screen unit to display a second segment of said information in place of said first segment in response to said gesture input.

49. The analyzer-programmer of claim 48, wherein said second segment includes a portion of said first segment.

50. The analyzer-programmer of claim 49, wherein said processor circuit in causing said integrated digitizer display screen unit to display a first segment of said information, selects an end of said second segment based on a location of said gesture on said integrated digitizer display screen unit.

* * * * *